(12) United States Patent
Ramanujam et al.

(10) Patent No.: US 11,805,994 B2
(45) Date of Patent: Nov. 7, 2023

(54) COLPOSCOPES, MAMMOSCOPES, AND INSERTERS HAVING CURVED ENDS AND ASSOCIATED METHODS

(71) Applicant: Duke University, Durham, NC (US)

(72) Inventors: Nirmala Ramanujam, Durham, NC (US); Mercy Asiedu, Durham, NC (US); Christopher Lam, Durham, NC (US); Jenna Mueller, Durham, NC (US); Julia Agudogo, Durham, NC (US); Robert Miros, San Rafael, CA (US)

(73) Assignee: Duke University, Durham, NC (US)

( * ) Notice: Subject to any disclaimer, the term of this patent is extended or adjusted under 35 U.S.C. 154(b) by 126 days.

(21) Appl. No.: 16/753,433

(22) PCT Filed: Oct. 4, 2018

(86) PCT No.: PCT/US2018/054397
§ 371 (c)(1),
(2) Date: Apr. 3, 2020

(87) PCT Pub. No.: WO2019/070998
PCT Pub. Date: Apr. 11, 2019

(65) Prior Publication Data
US 2020/0315444 A1    Oct. 8, 2020

Related U.S. Application Data

(60) Provisional application No. 62/568,119, filed on Oct. 4, 2017.

(51) Int. Cl.
*A61B 1/303* (2006.01)
*A61B 1/00* (2006.01)
(Continued)

(52) U.S. Cl.
CPC .......... *A61B 1/303* (2013.01); *A61B 1/00006* (2013.01); *A61B 1/00016* (2013.01);
(Continued)

(58) Field of Classification Search
CPC ..... A61B 1/303; A61B 1/043; A61B 1/00052; A61B 1/00096; A61B 1/00101;
(Continued)

(56) References Cited

U.S. PATENT DOCUMENTS 471,647 A * 3/1892 Magoris ................ A61M 25/04
604/39
4,210,133 A * 7/1980 Castaneda .............. A61B 1/303
600/179
(Continued)

FOREIGN PATENT DOCUMENTS

WO    2009/029254    3/2009
WO    2015/077684    5/2015
(Continued)

OTHER PUBLICATIONS

Subhash, N., et al. "Oral cancer detection using diffuse reflectance spectral ratio R54QIR575 of oxygenated hemoglobin bands." Journal of Biomedical Optics 11(1): 014018-014018 (2006).
(Continued)

*Primary Examiner* — John P Leubecker
(74) *Attorney, Agent, or Firm* — Myers Bigel, P.A.

(57) ABSTRACT

A colposcope includes an inserter including an elongated body defining an interior space and an image capture device configured to be selectively and slidably positioned within the interior space of the elongated body. The elongated body has a distal end portion and a proximal end portion. The distal end portion is substantially funnel shaped and has a distal end that includes first and second portions. The first portion includes a base at a first edge of the distal end, and
(Continued)

the second portion includes a lip at a second edge of the distal end that is diametrically opposed from the first edge. The lip is positioned further from the proximal end portion than the base.

18 Claims, 40 Drawing Sheets

(51) Int. Cl.
A61B 1/06 (2006.01)
A61B 1/307 (2006.01)
A61M 11/00 (2006.01)
A61M 31/00 (2006.01)

(52) U.S. Cl.
CPC ...... *A61B 1/00022* (2013.01); *A61B 1/00039* (2013.01); *A61B 1/00042* (2022.02); *A61B 1/00066* (2013.01); *A61B 1/00089* (2013.01); *A61B 1/00103* (2013.01); *A61B 1/00114* (2013.01); *A61B 1/00135* (2013.01); *A61B 1/0607* (2013.01); *A61B 1/0676* (2013.01); *A61B 1/0684* (2013.01); *A61B 1/307* (2013.01); *A61M 11/00* (2013.01); *A61M 31/005* (2013.01)

(58) Field of Classification Search
CPC ..... A61B 1/00188; A61B 1/012; A61B 1/018; A61B 1/307; A61B 1/00006; A61B 1/00016; A61B 1/00022; A61B 1/00039; A61B 1/00066; A61B 1/00089; A61B 1/00103; A61B 1/00114; A61B 1/00135; A61B 1/04; A61B 1/0607; A61B 1/0676; A61B 1/0684; A61B 1/00045; A61B 1/100052; A61B 1/00108; A61B 1/00087; A61M 11/00; A61M 31/005
See application file for complete search history.

(56) References Cited

U.S. PATENT DOCUMENTS

| | | | |
|---|---|---|---|
| 5,259,836 A | | 11/1993 | Thurmond et al. |
| 5,406,938 A | | 4/1995 | Mersch et al. |
| 6,010,450 A | * | 1/2000 | Perkins ............... A61B 1/0607 600/176 |
| 6,277,067 B1 | | 8/2001 | Blair |
| 6,447,444 B1 | | 9/2002 | Avni et al. |
| 6,496,718 B1 | | 12/2002 | Lonky |
| 6,526,980 B1 | * | 3/2003 | Tracy ...................... A61F 13/26 128/830 |
| 2005/0049509 A1 | | 3/2005 | Mansour et al. |
| 2005/0080318 A1 | | 4/2005 | Squicciarini |
| 2005/0080412 A1 | * | 4/2005 | Ouchi ............... A61B 18/1492 606/45 |
| 2005/0177027 A1 | | 8/2005 | Hirata |
| 2005/0277811 A1 | * | 12/2005 | Richards ............ A61B 1/00105 600/184 |
| 2006/0167340 A1 | | 7/2006 | Pease et al. |
| 2007/0049764 A1 | | 3/2007 | Ko et al. |
| 2007/0135819 A1 | | 6/2007 | Spiritos et al. |
| 2007/0177009 A1 | | 8/2007 | Bayer et al. |
| 2007/0191678 A1 | | 8/2007 | Sekiguchi |
| 2007/0213590 A1 | * | 9/2007 | Squicciarini ....... A61B 1/00101 600/172 |
| 2007/0232913 A1 | * | 10/2007 | Lau ........................ A61N 7/022 601/2 |
| 2008/0045791 A1 | | 2/2008 | Gal et al. |
| 2008/0058586 A1 | * | 3/2008 | Karpiel .............. A61B 1/00089 600/104 |
| 2008/0058590 A1 | * | 3/2008 | Saadat ..................... A61B 1/32 606/198 |
| 2008/0058605 A1 | | 3/2008 | Sorensen |
| 2008/0108869 A1 | | 5/2008 | Sanders et al. |
| 2008/0177142 A1 | | 7/2008 | Roskopf |
| 2009/0062662 A1 | | 3/2009 | Zuluaga |
| 2009/0062691 A1 | | 3/2009 | Kim |
| 2009/0082695 A1 | | 3/2009 | Whitehead |
| 2009/0203962 A1 | * | 8/2009 | Miller ................ A61B 1/00089 600/109 |
| 2010/0030020 A1 | | 2/2010 | Sanders et al. |
| 2010/0033563 A1 | | 2/2010 | Boehnlein et al. |
| 2010/0217084 A1 | | 8/2010 | Ishigami |
| 2010/0024960 A1 | | 9/2010 | Yu et al. |
| 2010/0305503 A1 | | 12/2010 | Fang et al. |
| 2011/0002584 A1 | | 1/2011 | Griffin |
| 2011/0023885 A1 | | 2/2011 | Vazales et al. |
| 2011/0112435 A1 | | 5/2011 | Ramanujam et al. |
| 2011/0184243 A1 | | 7/2011 | Wright et al. |
| 2011/0188716 A1 | * | 8/2011 | Bennett .............. A61B 5/14539 382/128 |
| 2011/0190579 A1 | * | 8/2011 | Ziarno ............... A61B 1/00096 600/109 |
| 2011/0190580 A1 | * | 8/2011 | Bennett ................ A61B 17/425 600/109 |
| 2011/0190581 A1 | * | 8/2011 | Bennett .................... A61B 5/68 600/109 |
| 2011/0190582 A1 | * | 8/2011 | Bennett .............. A61B 1/00096 600/109 |
| 2011/0190595 A1 | * | 8/2011 | Bennett .................... A61B 1/05 600/300 |
| 2011/0190596 A1 | | 8/2011 | Hacker et al. |
| 2011/0190689 A1 | | 8/2011 | Bennett et al. |
| 2012/0172664 A1 | | 7/2012 | Hayman et al. |
| 2012/0253123 A1 | | 10/2012 | Shimizu et al. |
| 2013/0053657 A1 | * | 2/2013 | Ziarno ................... A61B 1/042 600/588 |
| 2013/0066165 A1 | | 3/2013 | Shemer et al. |
| 2013/0137920 A1 | | 5/2013 | Schaeffer et al. |
| 2014/0088364 A1 | * | 3/2014 | Vail, III .................. A61B 1/07 600/135 |
| 2014/0243876 A1 | | 8/2014 | Suehara |
| 2015/0141742 A1 | * | 5/2015 | De Vries ................ A61B 1/303 600/29 |
| 2015/0150441 A1 | | 6/2015 | Ouyang et al. |
| 2016/0183778 A1 | * | 6/2016 | Nadershahi .......... A61B 1/0684 600/222 |
| 2016/0227994 A1 | | 8/2016 | Gotsch et al. |
| 2016/0262604 A1 | | 9/2016 | Greenstein et al. |
| 2016/0287063 A1 | * | 10/2016 | Ramanujam ....... A61B 1/00087 |
| 2017/0049312 A1 | | 2/2017 | Seth et al. |
| 2017/0064162 A1 | | 3/2017 | Haraguchi et al. |
| 2017/0245885 A1 | | 8/2017 | Lenker |
| 2017/0280988 A1 | | 10/2017 | Barbato et al. |
| 2018/0140320 A1 | * | 5/2018 | Aikawa .............. A61B 18/1492 |
| 2018/0317746 A1 | * | 11/2018 | Lalli .................... A61B 1/0014 |
| 2019/0150725 A1 | | 5/2019 | Ramanujam et al. |

FOREIGN PATENT DOCUMENTS

| | | | | |
|---|---|---|---|---|
| WO | WO 2015077684 A1 | * | 5/2015 | ......... A61B 1/00089 |
| WO | 2017/173178 | | 10/2017 | |

OTHER PUBLICATIONS

Van Gemert, M. J. C., et al. "Skin Optics." Biomedical Engineering, IEEE Transactions on 36(12): 1146-1154 (1989).
Vishwanath, Karthik, et al. "Portable, fiber-based, diffuse reflection spectroscopy (DRS) systems for estimating tissue optical properties." Applied Spectroscopy 65(2): 206-215 (2011).
Wagadarikar, Ashwin A., et al. "Video rate spectral imaging using a coded aperture snapshot spectral imager." Optics Express 17(8): 6368-6388 (2009).
Wang, Adrien, et al. "Targeting spectral signatures of progressively dysplastic stratified epithelia using angularly variable fiber geometry in reflectance Monte Carlo simulations." Journal of Biomedical Optics 12(4):044012.1-044012.14(2007).
Warde, Padraig, et al. "T1/T2 glottic cancer managed by external beam radiotherapy: the influence of pretreatment hemoglobin on

(56) References Cited

OTHER PUBLICATIONS local control" International Journal of Radiation Oncology* Biology* Physics 41 (2): 347-353 (1998).
Zeferino, Luiz Carlos, et al., "Cervical cancer in the developing world." Best Practice & Research Clinical Obstetrics& Gynecology 20.3: 339-354 (2006).
International Preliminary Report on Patentability for PCT Application PCT/US/2014067038 dated May 24, 2016.
International Search Report and Written Opinion for PCT Application PCT/US/2014067038 dated Mar. 25, 2015.
Written Opinion of International Searching Authority for PCT Application PCT/US/2014067038 dated Mar. 25, 2015.
Worcester, Sharon, "Novel device aims to make cervical cancer screening more accessible," MDedge:ObGyn, Aug. 2, 2017, 6 pages.
Thekkek, Nadhi, et al., "Optical imaging for cervical cancer detection: solutions for a continuing global problem.", Nature Reviews Cancer 8.9 (2008): 725-731.
Adams, E. Kathleen, et al. "Impact of the National Breast and Cervical Cancer Early Detection Program on mammography and Pap test utilization among white, Hispanic, and African American women: 1996-2000." Cancer 109.S2: 348-358 (2007).
Anderson, R. Rox, and Parrish, John A., "The optics of human skin." Journal of Investigative Dermatology 77(1):13-19 (1981).
Arifler, Dizem, et al. "Reflectance spectroscopy for diagnosis of epithelial precancer: model-based analysis of fiber-optic probe designs to resolve spectral information from epithelium and stroma." Applied Optics 44(20): 4291-4305 (2005).
Arifler, Dizem, et al. "Spatially resolved reflectance spectroscopy for diagnosis of cervical precancer: Monte Carlo modeling and comparison to clinical measurements." Journal of Biomedical Optics 11(6): 064027-064027(2006).
Bender, Janelle E., et al. "A robust Monte Carlo model for the extraction of biological absorption and scattering in vivo." Biomedical Engineering, IEEE Transactions on 56(4): 960-968 (2009).
Beumer, H.W, et al. "Detection of squamous cell carcinoma and corresponding biomarkers using optical spectroscopy." Otolaryngology—Head and Neck Surgery 144(3): 390-394 (2011).
Brizel, David M., et al. "Tumor hypoxia adversely affects the prognosis of carcinoma of the head and neck." International Journal of Radiation Oncology* Biology* Physics 38(2): 285-289 (1997).
Brown, J. Quincy, et al. "Quantitative optical spectroscopy: a robust tool for direct measurement of breast cancer vascular oxygenation and total hemoglobin content in vivo." Cancer Research 69(7): 2919-2926. (2009).
Cardena-Turanzas, Marylou, et al. "The clinical effectiveness of optical spectroscopy for the in vivo diagnosis of cervical intraepithelial neoplasia: where are we?." Gynecologic Oncology 107(1): S138-S146 (2007).
Cervical Cancer Prevention Initiatives at PATH Two decades of progress toward a world free of HPV-related cancers. LinkK http://screening.iarc.fr/doc/PATH_cxca_rep_to_world.pdf (2008).
Chang, Sung K., et al. "Combined reflectance and fluorescence spectroscopy for in vivo detection of cervical pre-cancer." Journal of Biomedical Optics 10(2): 024031.1-0240311.1 (2005).
Chang, Vivide Tuan-Chyan, et al. "Quantitative physiology of the precancerous cervix in vivo through optical spectroscopy." Neoplasia 11(4): 325-332 (2009).
Chang, Vivide Tuan-Chyan, et al. "Visible light optical spectroscopy is sensitive to neovascularization in the dysplastic cervix." Journal of Biomedical Optics 15(5): 057006-057006 (2010).
Cuccia, David J., et al. "Quantitation and mapping of tissue optical properties using modulated imaging." Journal of Biomedical Optics 14(2): 024012-1-024012-133 (2009).
De Veld, Diana CG, et al. "Autofluorescence and diffuse reflectance spectroscopy for oral oncology." Lasers in surgery and medicine 36.5 : 356-364 (2005).
Delong, Elizabeth R., David M. Delong, and Daniel L. Clarke-Pearson. "Comparing the areas under two or more correlated receiver operating characteristic curves: a nonparametric approach " Biometrics vol. 44: 837-845. (1988).
Dhar, Sulochana, et al. "A diffuse reflectance spectral imaging system for tumor margin assessment using custom annular photodiode arrays." Biomedical Optics express 3.12: 3211-3222(2012).
Dubray, Bernard, et al. "Anemia is associated with lower local-regional control and survival after radiation therapy for head and neck cancer: a prospective study" Radiology 201(2) : 553-558 (1996).
Ellsworth, Mary L., et al.. "Measurement of hemoglobin oxygen saturation in capillaries." American Journal of Physiology—Heart and Circulatory Physiology 252(5): H1031-H1040 (1987).
Extended European Search Report for corresponding EP Application No. 17776717.5 dated Jan. 29, 2020, 11 pages.
Follen, Michele, et al. "Optical technologies for cervical neoplasia: update of an NCI program project grant." Clinical Advances in Hematology and Oncology 3(1):41-53 (2005).
Freeberg, J. A, et al. "The performance of fluorescence and reflectance spectroscopy for the in vivo diagnosis of cervical neoplasia; point probe versus multispectral approaches." Gynecologic Oncology 107(1): S248-S255(2007).
Gao, Liang, et al. "Compact Image Slicing Spectrometer (ISS) for hyperspectral fluorescence microscopy." Optics express 17(15): 12293-12308 (2009).
Georgakoudi, Irene, et al. "Trimodal spectroscopy for the detection and characterization of cervical precancers in vivo." American journal of obstetrics and gynecology 186(3): 374-382 (2002).
Goldie, Sue J., et al. "Cost-effectiveness of cervical-cancer screening in five developing countries." New England Journal of Medicine 353(20): 2158-2168 (2005).
Hasina, R., and Mark W. Lingen. "Angiogenesis in oral cancer." Journal of dental education 65(11): 1282-1290 (2001).
International Search Report and Written Opinion for PCT/US18/54397, dated Dec. 7, 2018, 11 pages.
International Search Report and Written Opinion for PCT/US2017/025197 dated Jun. 9, 2017, 8 pages.
Kujan, Omar, et al. "Screening programmes for the early detection and prevention of oral cancer." The Cochrane Library Issue 11(2010).
Lane, Pierre M., et al. "Simple device for the direct visualization of oral-cavity tissue fluorescence." Journal of Biomedical Optics 11 (2): 024006.1-024006.7 (2006).
Lee, W. Robert, et al. "Anemia is associated with decreased survival and increased locoregional failure in patients with locally advanced head and neck carcinoma: a secondary analysis of RTOG 85-27." International Journal of Radiation Oncology* Biology* Physics 42(5 ): 1069-1075 (1998).
Liu, Quan, and Ramanujam, Nirmala "Sequential estimation of optical properties of a two-layered epithelial tissue model from depth-resolved ultraviolet-visible diffuse reflectance spectra." Applied Optics 45(19): 4776-4790 (2006).
Marin, Nena M., et al. "Diffuse reflectance patterns in cervical spectroscopy." Gynecologic Oncology 99(3): S116-S120 (2005).
Marks, James S., et al. "Implementing recommendations for the early detection of breast and cervical cancer among low-income women." Morbidity and Mortality Weekly Report: Recommendations and Reports vol. 4 No. RR-2: 35-55 (2000).
Mirabal, Yvette N., et al. "Reflectance spectroscopy for in vivo detection of cervical precancer." Journal of Biomedical Optics 7(4): 587-594 (2002).
Muller, Markus G., et al. "Spectroscopic detection and evaluation of morphologic and biochemical changes in early human oral carcinoma." Cancer 97(7): 1681-1692 (2003).
Nordsmark, Marianne, et al. "Prognostic value of tumor oxygenation in 397 head and neck tumors after primary radiation therapy. An international multi-center study" Radiotherapy and Oncology 77(1): 18-24 (2005).
Palmer, M.P. et al., "Monte Carlo-based inverse model for calculating tissue optical properties. Part 1: Theory and validation on synthetic phantoms," Appl. Opt. '15; 1062-1071 (2006).
Partial European Search Report for EP application No. 17776717.5 dated Oct. 28, 2019, 13 pages.

(56) References Cited

OTHER PUBLICATIONS

Pavlova, Ina, et al. "Fluorescence spectroscopy of oral tissue: Monte Carlo modeling with site-specific tissue properties." Journal of Biomedical Optics 14(1): 014009-014009 (2009).

Phelps, Janelle E., et al. "Rapid ratiometric determination of hemoglobin concentration using UV-VIS diffuse reflectance at isosbestic wavelengths." Optics Express 18(18): 18779-18792 (2010).

Pittman, Roland N., and Brian R. Duling. "A new method for the measurement of percent oxyhemoglobin." Journal of Applied Physiology 38(2): 315-320 (1975).

Rahman, Mohammed, et al. "Low-cost, multimodal, portable screening system for early detection of oral cancer." Journal of Biomedical Optics 13(3): 030502-030502 (2008).

Sankaranarayanan, Rengaswamy, et al. "Effect of screening on oral cancer mortality in Kerala, India: a cluster-randomised controlled trial." The Lancet 365(9475): 1927-1933 (2005.

Sankaranarayanan, Rengaswamy, et al. "HPV screening for cervical cancer in rural India." New England Journal of Medicine 360(14): 1385-1394 (2009).

Saslow, Debbie, et al. "American Cancer Society guideline for the early detection of cervical neoplasia and cancer." CA: a Cancer Journal for Clinicians 52(6): 342-362.(2002).

Schwarz, Richard A., et al. "Autofluorescence and diffuse reflectance spectroscopy of oral epithelial tissue using a depth-sensitive fiber-optic probe" Applied Optics 47(6): 825-834 (2008).

Sharwani, A., et al. "Assessment of oral premalignancy using elastic scattering spectroscopy." Oral Oncology 42.4: 343-349 (2006).

Sherris, Jacqueline, et al., "Beyond our borders: cervical cancer in the developing world." Western Journal of Medicine 175(4): 231 (2001).

Skala, Melissa C., et al. "Comparison of a physical model and principal component analysis for the diagnosis of epithelial neoplasias in vivo using diffuse reflectance spectroscopy." Optics Express 15(12): 7863-7875 (2007).

\* cited by examiner

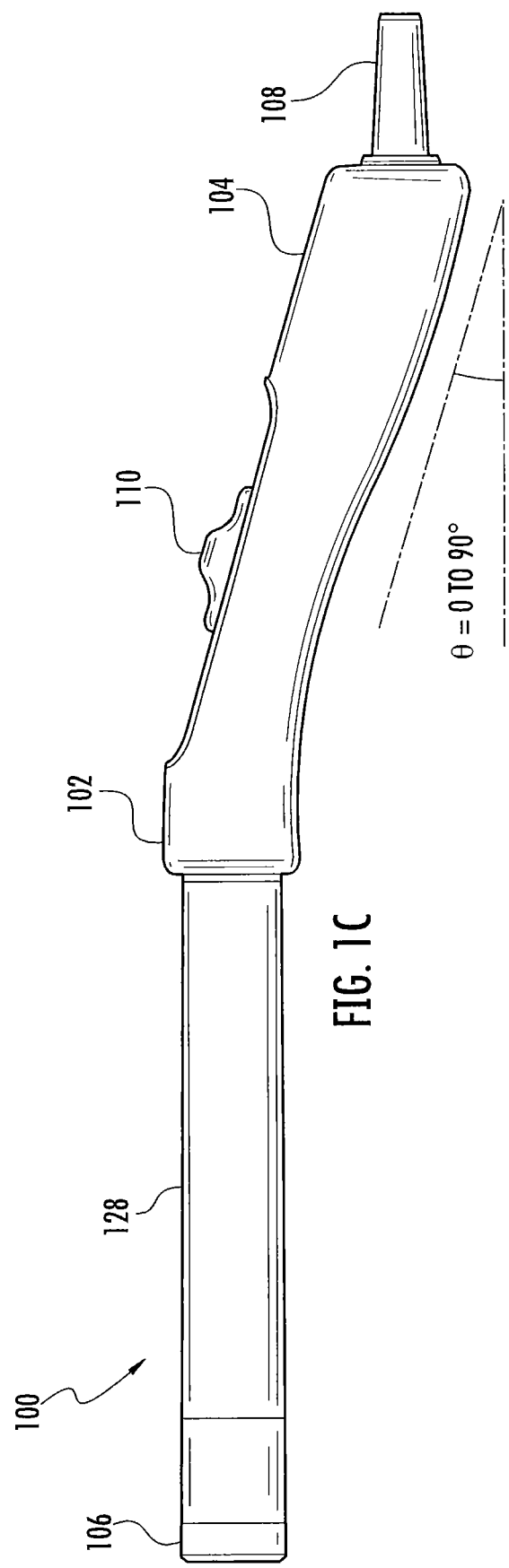

75° REFLECTOR
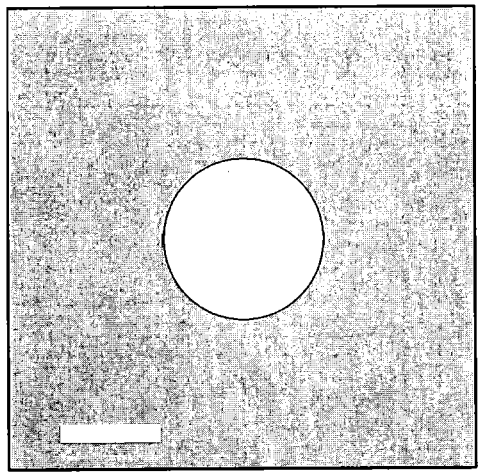
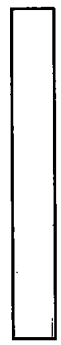
$1.20*10{-3}$ mw/cm$^2$
$6.00*10{-4}$
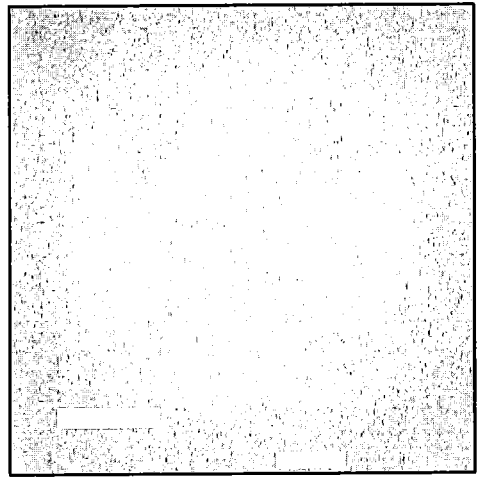
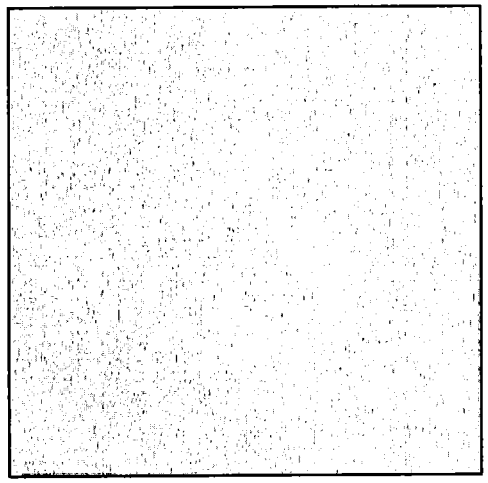
FIG. 5A

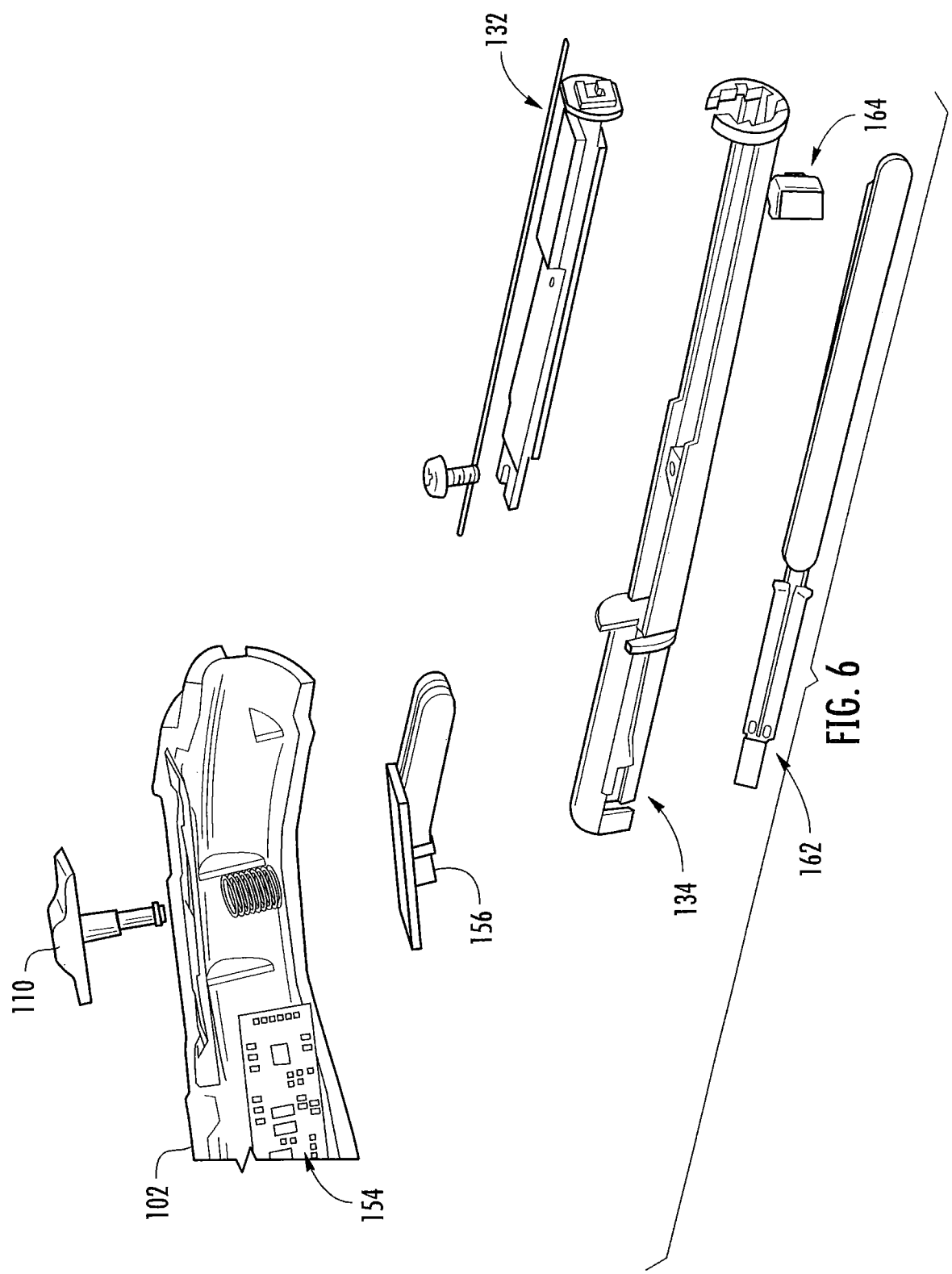

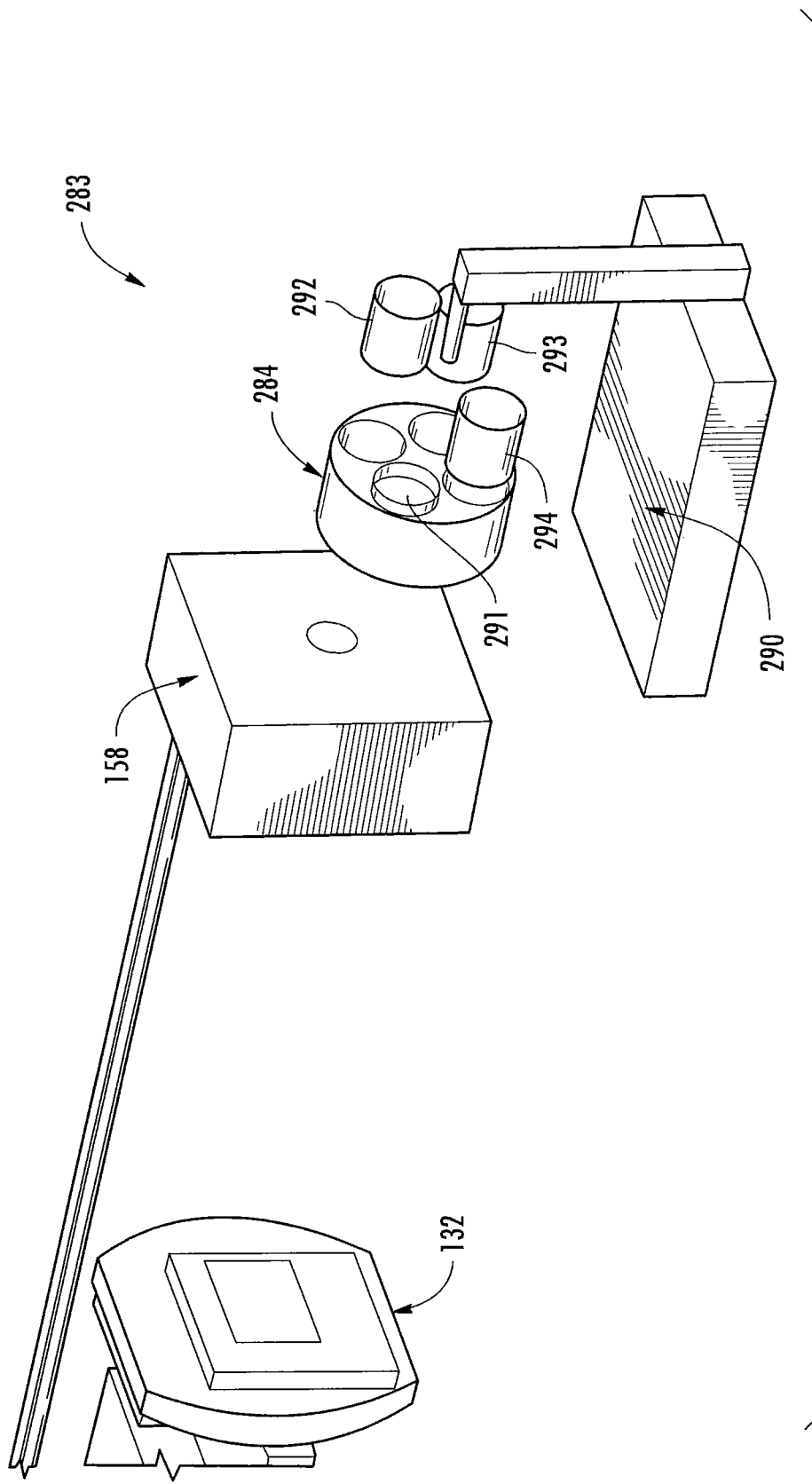

REMOVABLE INSERTER TIP

INSERTER STEM

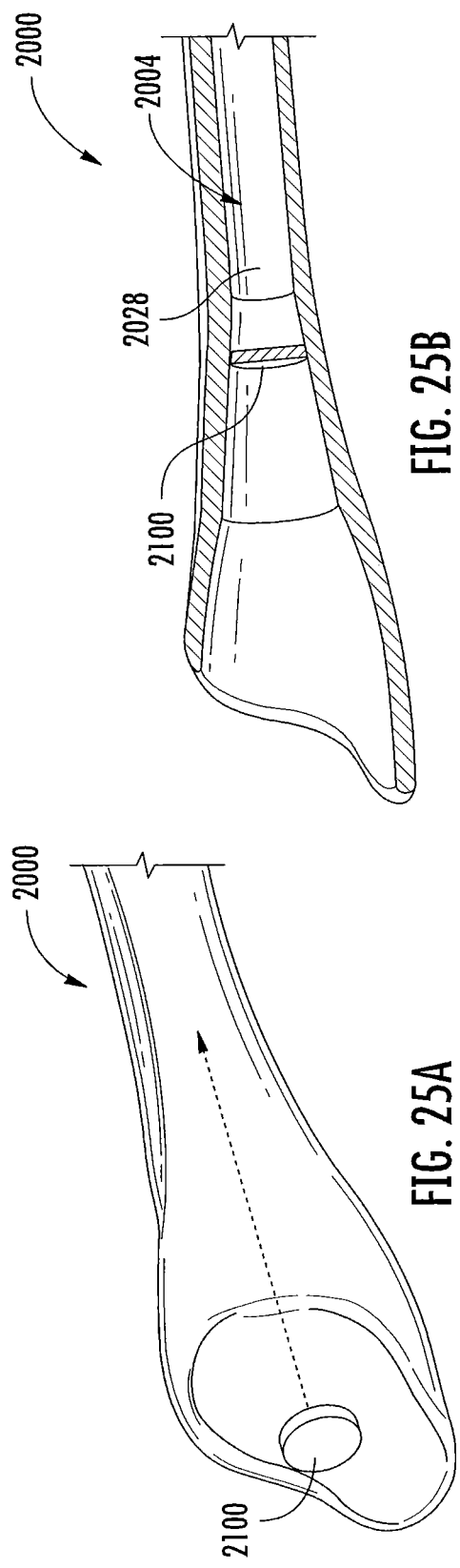
FIG. 25A
FIG. 25B
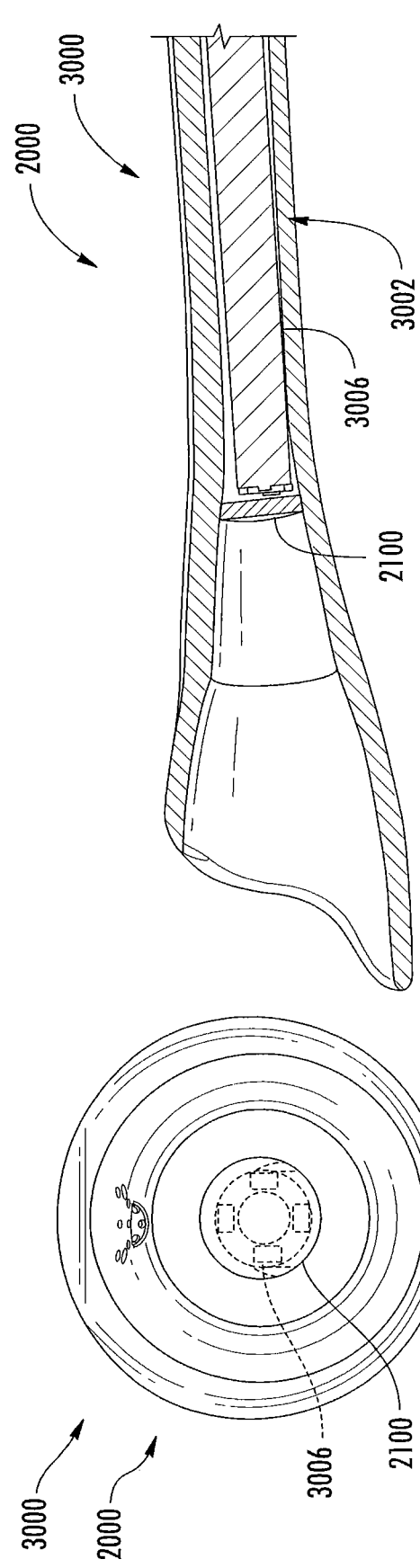
FIG. 25C
FIG. 25D

COLPOSCOPES, MAMMOSCOPES, AND INSERTERS HAVING CURVED ENDS AND ASSOCIATED METHODS

CROSS REFERENCE TO RELATED APPLICATIONS

This application is a 35 U.S.C. § 371 national stage application of PCT International Application No. PCT/US2018/054397, filed Oct. 4, 2018, which application claims the benefit of and priority from U.S. Provisional Patent Application No. 62/568,119, filed Oct. 4, 2017, the disclosure of each of which is incorporated herein by reference in its entirety.

STATEMENT AS TO FEDERALLY SPONSORED RESEARCH

This invention was made with the support of the United States government under Federal Grant Nos. 1 R01 CA193380-01 and 1 R01 CA195500-01 and awarded by the National Institutes of Health (NIH). The Government has certain rights in this invention.

TECHNICAL FIELD

The presently disclosed subject matter relates to colposcopes, inserters, and speculum-free imaging methods.

BACKGROUND

Invasive Cervical Cancer (ICC) is the second most common female cancer in low and middle-income countries (LMICs) and the seventh most common in high-income countries. Annually, over 500,000 women are diagnosed, causing over 270,000 deaths recorded with more than 75% of cases occurring in Africa and India. The World Health Organization (WHO) estimates that currently 88% of worldwide ICC mortalities occur in LMICs, and this rate is expected to increase to 98% by 2030, furthering the disparities as the total number of annual worldwide mortalities increases to nearly 400,000. Though early diagnosis and treatment of cervical pre-cancers have been shown to significantly increase survival rates, diagnostic tools are not widely available in LMICs. Currently, as an alternative to cytology screening, the standard-of-care screening method in most LMICs is visual inspection with acetic acid (VIA), with or without digital image capture. This technique involves the use of a speculum to expand the vaginal canal to enable a clear field-of-view of the cervix, for visualization with a colposcope, camera or directly by the health provider (naked eye). Speculums are needed mainly because of the need to expand the entire vaginal canal.

During the VIA procedure, 3-5% acetic acid is applied to the surface of the cervix. A positive VIA exam shows a sharp, distinct, well-defined, dense aceto-white area, with or without raised margins. If a camera or digital colposcope is available, images of the cervix can be visualized at higher magnification and can also be archived for further analysis and review.

Generally, colposcopes are stereomicroscopes with an extended working distance of between 250-350 mm. Working distance is defined as the length from the last optical element (outermost) to the target object. Colposcopes have 5 glass lens elements: common objective, zoom system (2 elements), erecting beam splitter, and eyepieces. A digital camera can be added with the use of a beam splitter between the right most zoom element and eyepiece. The mechanically compensated zoom lens systems allows for the working distance to remain constant when changing between magnifications, these 2 elements move independently. The colposcope lens elements are comprised of different glass materials of different refractive indices (crown and flint), with antireflective coating, and between 25 to 50 mm in diameter. Due to the complex arrangement and large number of elements of the traditional colposcope, the large device footprint, lack of portability due to weight, an expensive capital purchase, and reliance on walled electricity make wide scale dissemination and uptake difficult.

The speculum has been identified as a significant factor in the resistance of women to undergo cervical cancer screening, largely due to anxiety, fear, discomfort, pain, embarrassment, and/or vulnerability during the procedure. In the U.S., even though there is greater access to health care, compliance rates to cervical cancer screening vary, and embarrassment and fear of pain during examination have been reported as potential barriers to screening.

The speculum has been in existence in various shapes and forms since the tenth century and has evolved with hundreds of modifications in attempts to enhance exposure. The first rudimentary prototype of the modern speculum was developed out of a bent spoon. The semblance to the standard bivalve speculum was put forward by the manufacturer Charriere who introduced the bivalve, tri-blade and four-blade speculum. This inspired the duck bill designs of the familiar Cusco speculum in 1870 and the Graves speculum in 1878. These are cold, hard, metal devices with two bills each that expand the entire vaginal canal. Since the introduction of duck billed speculums, there have been few improvements to make them more comfortable and acceptable for women. Slight changes in design have involved introducing a variety of sizes and making the speculum out of plastic. Current speculums are designed for an external user, which makes it difficult for self-insertion by women. Being able to self-insert is important in being able to re-adjust when there is discomfort. Furthermore, in cases where women have tilted uteri or lax vaginal walls due to having a larger body size or a high parity, increased manipulation or use of an extra device, such as a side wall retractor, is needed to obtain a clear view of the cervix. This further adds to discomfort and pain during vaginal examinations.

The few attempts at major changes in the redesign of the speculum have been somewhat unsuccessful. The FemSpec, a clear plastic cylinder with inflatable air pockets, was developed in 2005 by FemSuite of San Francisco, Calif. The FemSpec has a tampon-sized insertion diameter and, once inserted, can be inflated to expand the vaginal walls. This was taken off the market due to the reluctance of medical professionals to embrace the device. This device has been found to have sharp plastic edges and unable to withstand high vaginal pressures. The Vedascope, designed in Australia, is an encompassing speculum/colposcopic device, which dilates the vagina with air inflow and is attached to a camera and illumination for colposcopy. Though 92% of women have indicated a preference for the Vedascope to the speculum, it is very bulky, expensive and requires physician placement. Additionally, it has a potential risk for air embolism, which can be fatal.

In view of the foregoing, there is a need for improved speculum/colposcopic devices.

SUMMARY

Some embodiments of the present invention are directed to a colposcope including an inserter and an image capture device. The inserter includes an elongated body defining an interior space and having a distal end portion and a proximal end portion. The distal end portion is substantially funnel shaped and having a distal end that includes first and second portions. The first portion includes a base at a first edge of the distal end and the second portion includes a lip at a second edge of the distal end that is diametrically opposed from the first edge. The lip is positioned further from the proximal end portion than the base. The image capture device is configured to be selectively and slidably positioned within the interior space of the elongated body.

In some embodiments, the body includes a transition portion between the proximal end portion and the distal end portion. The proximal end portion of the body may have a constant diameter circular cross section. The distal end portion of the body may have a circular cross section that increases in diameter from the transition portion to the distal end of the body. The distal end of the body may have a diameter of between 20 and 30 mm. The proximal end portion of the body may have a diameter of between 5 and 25 mm.

In some embodiments, the image capture device includes a handle and an elongated probe extending from the handle. The handle may include a collar that surrounds a proximal end portion of the probe. The handle collar may be held in the proximal end portion of the inserter body with the image capture device in an installed position. A distal end of the probe may be in the distal end portion and/or the transition portion of the inserter body with the image capture device in the installed position. The handle collar may be held in the proximal end portion of the inserter body with a friction fit with the image capture device in the installed position.

In some embodiments, a plurality of LEDs surround a lens of the image capture device at a distal end of the probe. The handle may include a body, a first button or dial on the body for adjusting the brightness of the plurality of LEDs, and/or a second button on the body for capturing an image.

In some embodiments, an anti-reflective, hydrophobic window is in the interior space of the elongated body of the inserter and defines a barrier for the image capture device such that any fluid entering the interior space from the distal end does not reach the image capture device. The inserter may be single-use disposable. The hydrophobic window may be in the distal end portion and/or the transition portion of the body. The hydrophobic window may be adhered to the body of the inserter by epoxy. The hydrophobic window may be ultrasonically welded to the body of the inserter.

In some embodiments, at least one channel extends along the body from the proximal end portion to the distal end portion for fluid communication of contrast agent from the proximal end portion to the distal end portion. A spray mechanism may be in fluid communication with the at least one channel at the distal end portion. The spray mechanism may be configured to disperse the contrast agent at the distal end portion. The spray mechanism may include a spray nozzle including a plurality of holes defined in an inner surface of the body and spaced apart from the distal end of the body. A tube and/or connector may be in fluid communication with the at least one channel at a proximal end of the body. The tube and/or connector may be configured to receive a syringe for injection of the contrast agent.

In some embodiments, the body defines a longitudinal axis. An angle between the base and the lip may be between 30 and 50 degrees or between 35 and 45 degrees measured relative to a plane that is orthogonal to the longitudinal axis. A distance between the base and the lip parallel to the longitudinal axis may be between 10 and 30 mm or between 15 and 25 mm. A width of the lip may vary from the diameter or about the diameter of the distal end of the inserter to ⅓ of the diameter or about ⅓ of the diameter of the distal end.

In some embodiments, the body includes a stem defining the proximal end portion and optionally a portion of the distal end portion and optionally at least a portion of the transition portion. The body may include a tip defining at least a portion of the distal end portion. The tip may be attached to the stem. The tip may be releasably attached to the stem. The stem may have increased rigidity relative to the tip. The tip may include a biocompatible material such as a polymer or rubber (e.g., silicone).

In some embodiments, a reflective coating is on an inner surface of the distal end portion of the body.

In some embodiments, the elongated body has a fixed length and the proximal end portion has a fixed diameter for fitting to the image capture device.

In some embodiments, the distal end portion is configured of a size and shape to fit to different cervix sizes.

In some embodiments, the colposcope or colposcope system includes an electronic device. At least one cable may be configured to operatively connect the electronic device and the image capture device. In some embodiments, the electronic device is configured to power and communicate with the image capture device. The electronic device may include a user interface to enable data storage and/or telemedicine. The image capture device may include a microcontroller and a transmitter configured to wirelessly transmit image data to an electronic device.

In some embodiments, the inserter is configured for speculum-free imaging with uniform illumination of the cervix.

Some other embodiments of the present invention are directed to a method including: providing a colposcope as described herein; sterilizing the inserter; connecting the image capture device to an electronic device; slidably receiving the image capture device in the inserter; adjusting the brightness, resolution, and/or focus of the image capture device; applying lubrication on the funnel shaped distal end of the inserter; placing the inserter into a vagina with the lip first; navigating the inserter through the vaginal canal until the cervix is reached; rotating the inserter until cervical os is centered and cervix is fully in view; capturing an image or video of the cervix; and optionally viewing the image or video on an electronic device that is communicatively coupled to the image capture device.

Some other embodiments of the present invention are directed to a colposcope including an elongated body including a handle and a probe, an image capture device within an interior space of the probe, a prime lens system within the interior space of the probe and positioned between the image capture device and a distal end of the body, a light baffle within the interior space of the probe and positioned between the prime lens system and the distal end of the body, an LED ring within the interior space of the probe and positioned between the light baffle and the distal end of the body, a light diffuser and/or light guide within the interior space of the probe and positioned between the LED ring and the distal end of the body, and anti-reflection coated, hydrophobic window positioned at the distal end of the body and positioned within a field of view of the image capture device. The probe extends from the distal end of the body to the handle. The LED ring includes a plurality of LEDs arranged concentrically around a lens of the image capture device. The plurality of LEDs are positioned to generate and direct light toward an area outside of the elongated body.

In some embodiments, a control panel is on the handle and associated electronics are held in an interior space of the handle. The control panel and associated electronics may be configured to select from among a plurality of modes of illumination for an object in the field of view of the image capture device. The control panel may include: a slider configured to be actuated to control the working distance, the field of view, and/or the resolution of the image capture device; a first button configured to be actuated to select from among the plurality of modes of illumination for an object in a field of view of the image capture device; and/or a second button configured to be actuated to capture and save an image. The plurality of modes of illumination may include low white for an acetic acid image, bright white for a Lugol's iodine image, and green for enhanced vascular visualization. The illuminance for the low white mode may be between 100 and 650 lux. The illuminance for the bright white mode may be between 1000 and 5000 lux. The illuminance for the green mode may be between 250 and 1250 lux. The the first button may be positioned between the slider and the distal end of the body. The second button may be positioned between the slider and a proximal end of the body.

In some embodiments, a camera sled is held within the interior space of the probe. The image capture device may be held in the camera sled. The slider may be operatively connected to the camera sled such that translation of the slider causes translation of the camera sled and the camera relative to the prime lens system to facilitate coarse focus adjustment. A magnet may be held by the camera sled. A linear digital potentiometer may be held within the interior space of the probe and may be configured to measure displacement of the magnet responsive to translation of the slider.

In some embodiments, a rotatable filter wheel is in the interior space of the probe between the prime lens system and the light baffle. The rotatable filter wheel may hold a plurality of fluorescent bandpass filters. The plurality of LEDs may include an alternating sequence of white, blue, and green for FITC excitation. The plurality of LEDs may include an alternating sequence of white, blue, cyan, green, amber, and orange for multi-fluorophore excitation.

In some embodiments, the colposcope or colposcope system includes an electronic device and/or at least one cable configured to operatively connect the electronic device and the image capture device. The electronic device may be configured to power and communicate with the image capture device. The cable may have a length of between 1 and 3 meters.

In some embodiments, the colposcope or colposcope system includes an electronic device optionally with a rechargeable battery. A wireless transmitter may be in an interior space of the handle. The wireless transmitter may be configured to wirelessly communicate with the electronic device and send captured images and/or captured image data to the electronic device. A rechargeable battery may be in the interior space of the handle.

In some embodiments, the probe has a fixed diameter between 5 and 25 mm. The probe may have a fixed length of between 100 and 250 mm, between 150 and 225 mm, or between 175 and 200 mm. The handle may have a fixed length of between 115 and 125 mm. The handle may have a fixed diameter of between 20 and 25 mm. The handle may be angled relative to the probe at an angle of between 0 and 90 degrees, between 5 and 45 degrees, or between 5 and 25 degrees. The colposcope may have a weight of less than 1 pound or less than 0.5 pounds.

In some embodiments, the body is rigid.

In some embodiments, the light diffuser and/or light guide comprises an annular body that resides in front of the plurality of LEDs and an aperture defined in the body and aligned with an image axis of the image capture device. The hydrophobic window may be received in the aperture and reinforced by medical grade epoxy to prevent liquid and particle infiltration.

In some embodiments, the handle includes first and second portions that are ultrasonically welded to one another such that the handle is water resistant. The probe and the handle may be ultrasonically welded to one another such that an interface between the probe and the handle is water resistant. An end cap may be at the distal end of the body. The end cap may be ultrasonically welded to the probe such that the distal end of the body is water resistant. In this regard, the entire body of the colposcope may be water resistant.

Further features, advantages and details of the present invention will be appreciated by those of ordinary skill in the art from a reading of the figures and the detailed description of the preferred embodiments that follow, such description being merely illustrative of the present invention.

BRIEF DESCRIPTION OF THE DRAWINGS

The foregoing aspects and other features of the present subject matter are explained in the following description, taken in connection with the accompanying drawings, wherein:

FIGS. 1A-1F are different views of an example colposcope for imaging precancerous cervical lesions in accordance with embodiments of the present disclosure;

FIGS. 5A-5E are various images showing experimental results conducted with example end caps in accordance with embodiments of the present disclosure;

FIG. 6 is an exploded view of a slider zoom mechanism in accordance with embodiments of the present disclosure;

FIGS. 8A, 8D, and 8E are exploded views of another implementation of the device for imaging breast tumor margins topically stained with fluorescent contrast agents, which is referred to as the mammoscope in accordance with embodiments of the present disclosure;

FIGS. 25A-25D illustrate a hydrophobic window integrated with the inserter of FIGS. 17-20.

DETAILED DESCRIPTION

For the purposes of promoting an understanding of the principles of the present disclosure, reference will now be made to various embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

Unless otherwise defined, all technical terms used herein have the same meaning as commonly understood by one of ordinary skill in the art to which this disclosure belongs.

As used herein, the term "and/or" includes any and all possible combinations or one or more of the associated listed items, as well as the lack of combinations when interpreted in the alternative ("or").

Articles "a" and "an" are used herein to refer to one or to more than one (i.e. at least one) of the grammatical object of the article. By way of example, "an element" means at least one element and can include more than one element.

Figure 2:
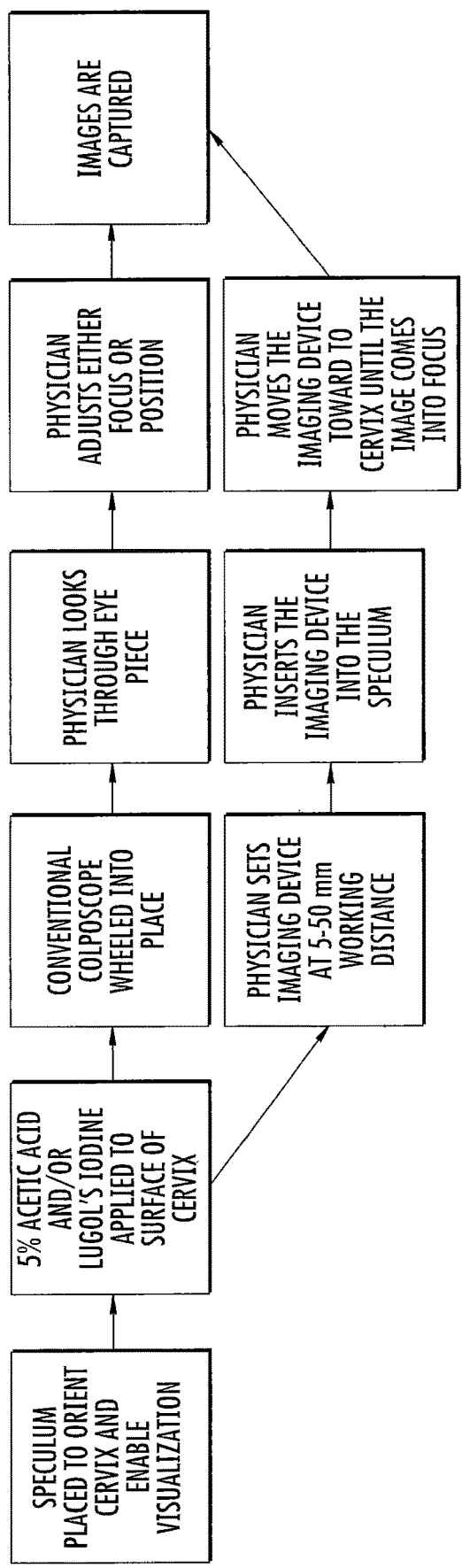
FIG. 2 is a flow chart for illustrating the use of the colposcope of FIGS. 1A-1F and its integration in clinical workflow in accordance with embodiments of the present disclosure.

Conventional colposcopes are stereomicroscopes with an extended working distance of between 250-350 mm while the image devices described herein are transvaginal and have a working distance between 5-50 mm. Thus, the methods for use (which are summarized in FIG. 2) are different. For both devices, a speculum is placed in the vagina, and 5% acetic acid and/or Lugol's iodine is applied to the cervix of each patient. The speculum is used to manipulate the orientation of the cervix for better visualization and is required for both devices. Next, a physician wheels the conventional colposcope into place, looks through the eye piece, adjusts either the focus or the position of the colposcope (by wheeling it closer or further away from the patient), and captures an image. Conversely, the physician can set the image device described herein at the 5-50 mm working distance by adjusting the focus slider all the way back, can place the device in the speculum, can move the device toward the cervix until the image comes into focus, and can capture an image. Captured images may be suitably stored and processed. In an example, the images may be communicated or downloaded to a server for remote expert diagnosis. The colposcope may be suitably sterilized and subsequently re-used.

Figure 1A:
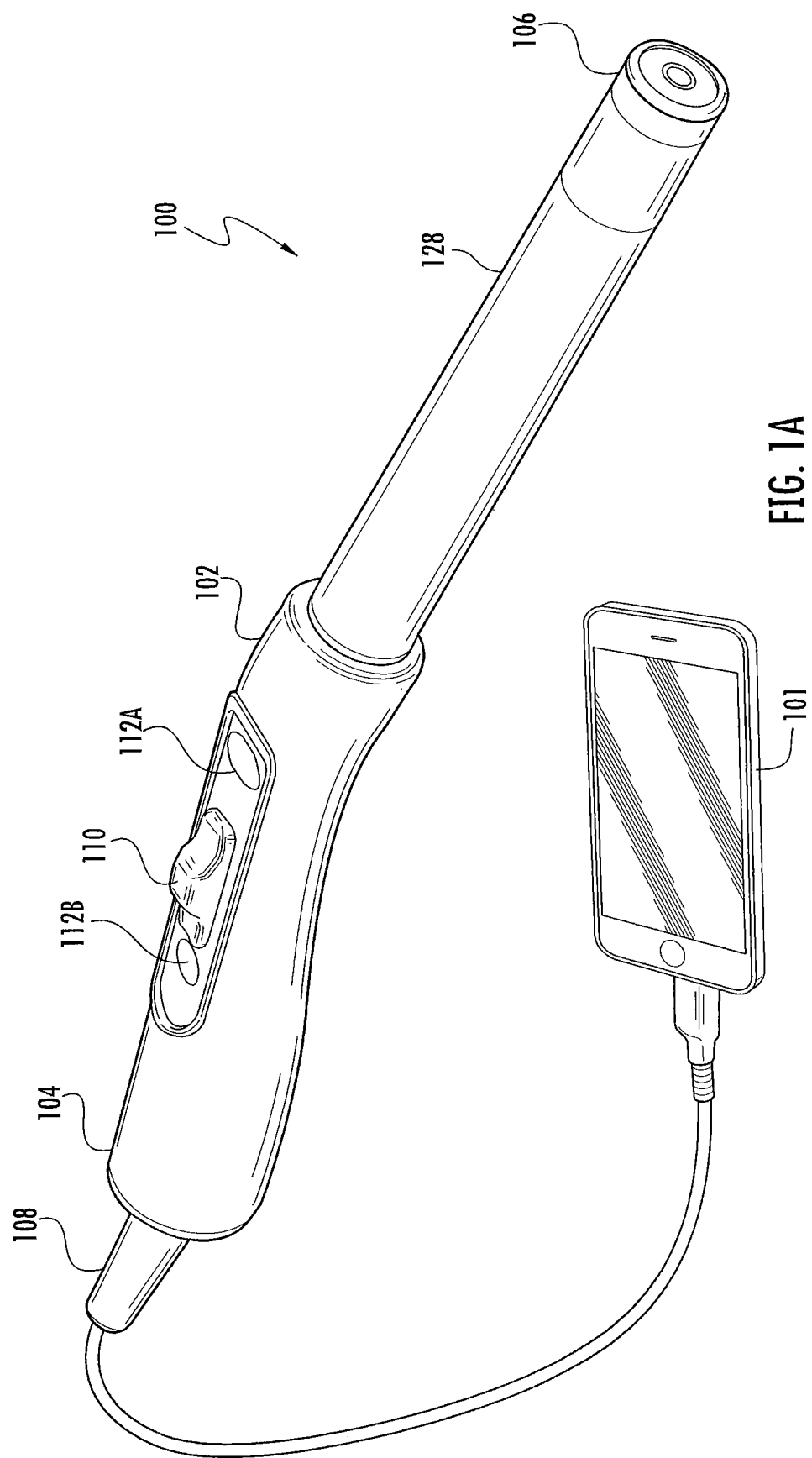
Figure 1B:
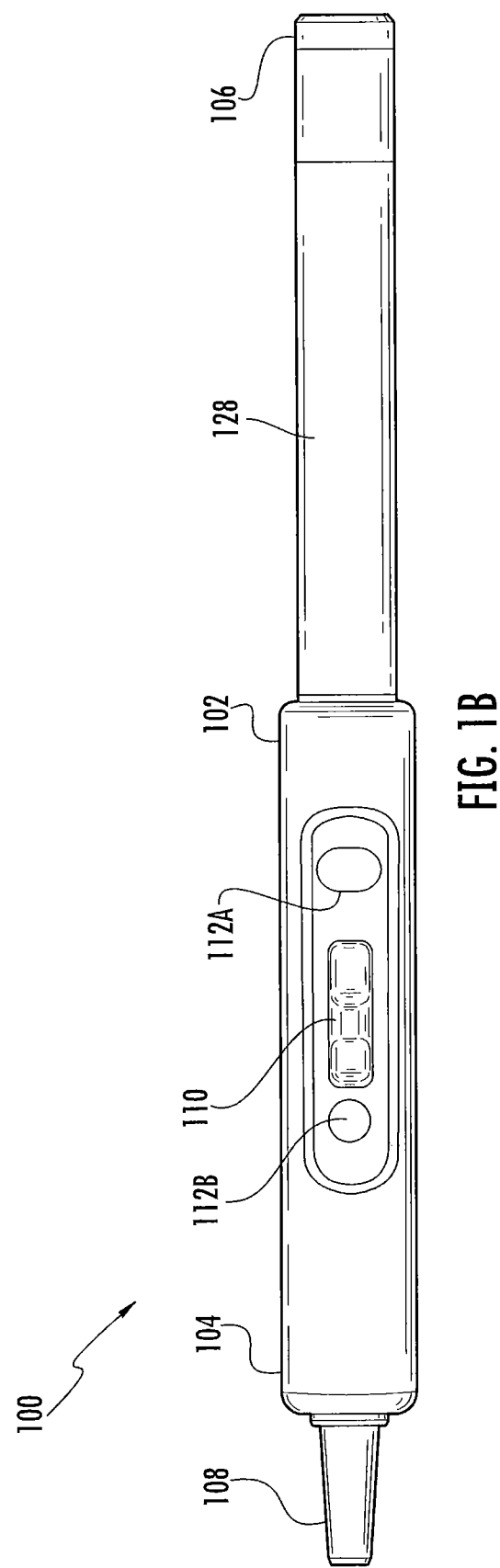
Figure 1D:
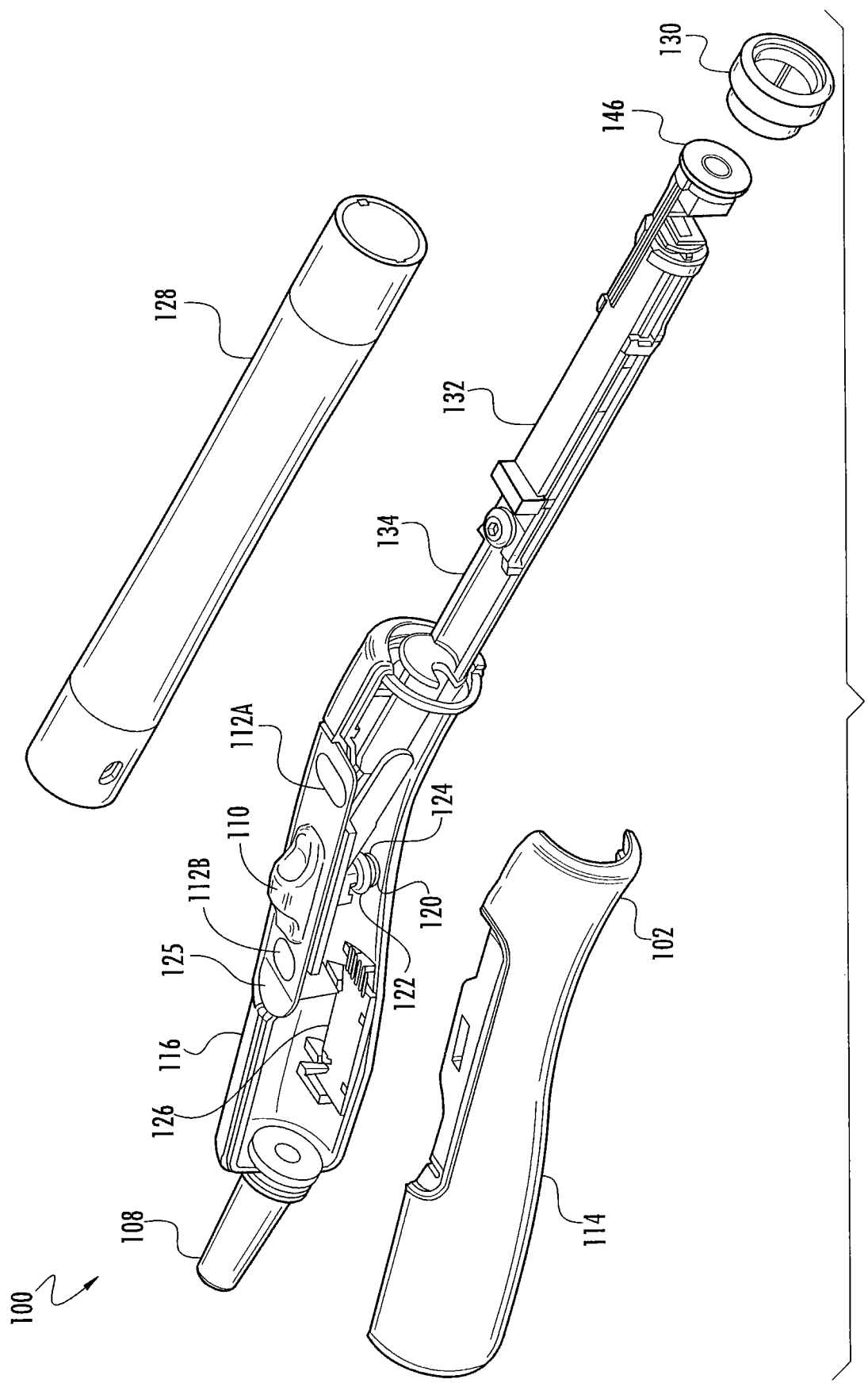
Figure 1E:
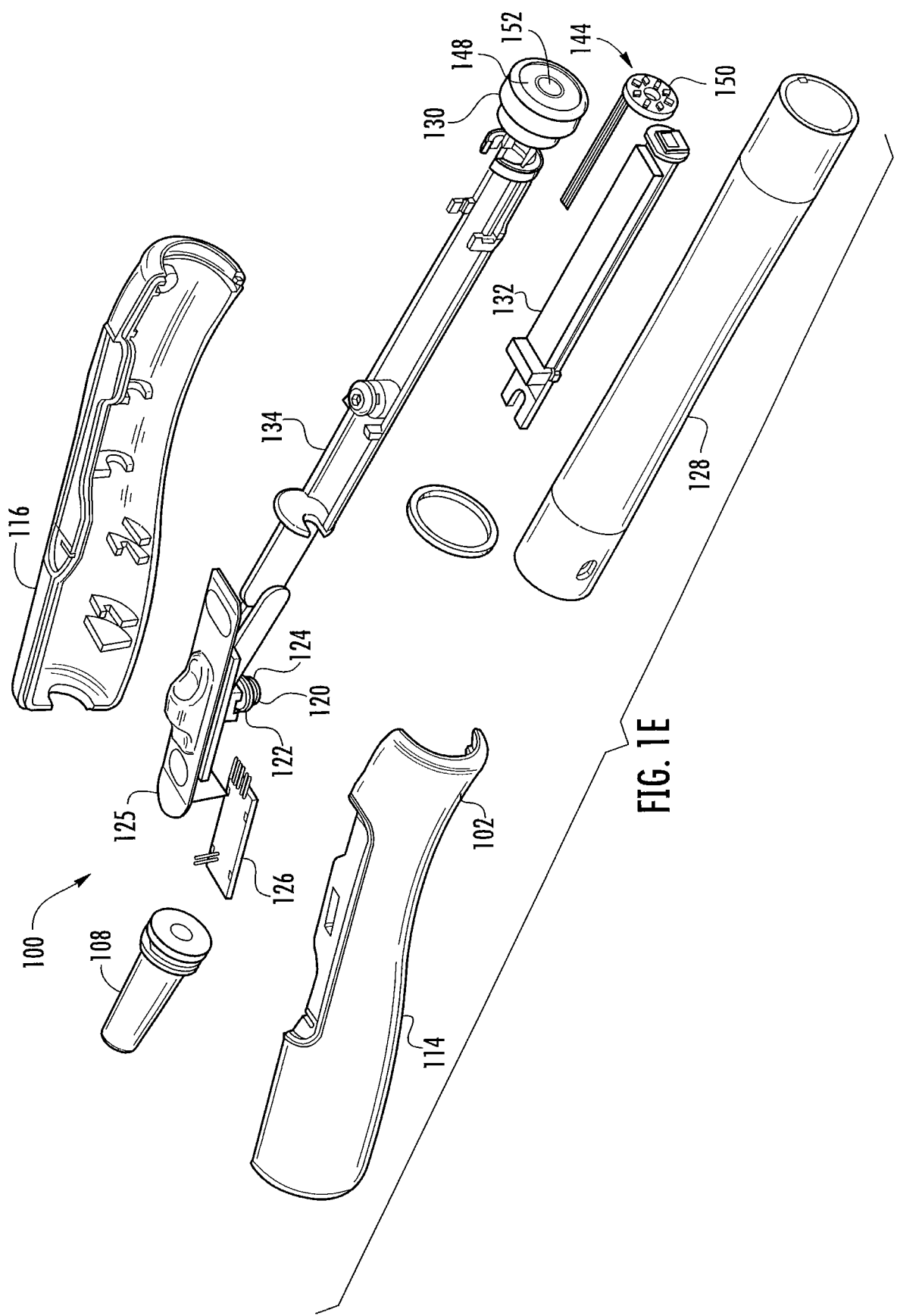

FIGS. 1A-1E illustrate different views of an example colposcope 100 for imaging precancerous cervical lesions in accordance with embodiments of the present disclosure. Referring to FIG. 1A, the figure shows a perspective view of the colposcope 100 including a handle 102 at a proximate end 104 and a probe 128 at a distal end 106. Referring to FIG. 1C, in some embodiments, the handle can be at an angle Θ of 0 to 90 degrees relative to the probe. In other embodiments, the handle can be at an angle of 5 to 45 degrees relative to the probe. In some other embodiments, the handle can be at an angle of 5 to 25 degrees relative to the probe. The diameter of the probe can range from 20-25 mm and the length of the probe can range from 115 to 125 mm. The angle, diameter, and length of the probe were selected to enable physicians to easily hold the probe while simultaneously being able to visualize the cervix while inserting the imaging device into the speculum. Referring to FIGS. 1D and 1E, the colposcope includes a camera (e.g., a 5 MP camera) 132 and white, green, and/or blue light emitting diodes LEDs 144 functionally integrated into the distal end 106. A glass optical long pass filter 505 nm (housed in 146) may be used to remove the excitation light (blue LEDs) for the fluorescent compound and only allow higher fluorescent light to return to the camera, but not interfere with white and green illumination modes. In an example, the colposcope 100 weighs less than 0.5 pounds, which enables the physician to easily hold the imaging device with one hand thus ensuring compatibility with current clinical workflow. The colposcope 100 also includes an electronic cord 108 for connection and interface to an electronic device 101 (FIG. 1A), such as various electronic devices for control and presentation as described herein (e.g., laptop, smartphone, tablet, etc.). The electronic cord 108 may also provide power to the device for enabling imaging and other functions. The cord 108 may be Universal Serial Bus (USB) cable of length between 1 to 3 meters to allow for variations in hospital room and/or clinic room set up. The USB cord is a light and nonintrusive way to power the camera and illumination components of the device.

In some embodiments, the device has the capability for cordless operation, which entail the incorporation of a rechargeable lithium polymer or similar battery with protective circuitry to prevent over-discharge and report on status of the battery, into the probe handle and wireless transmitter (that could include any or all of the following: near field communication (NFC), Bluetooth, wireless local area network (Wi-Fi), cellular (3G, 4GLTE), among others). A nearby smartphone, tablet, or portable laptop computer could receive images and video in real time to display and store the data. A docking station that enables wireless rapid charging could be provided using electromagnetic induction. Another embodiment of the device could also store the images securely on non-volatile flash memory and send images on demand.

The handle 102 includes a control panel having a slider 110 and buttons 112A and 112B for control of operation of the colposcope 100. Particularly, the slider 110 can be moved by a user to control the working distance, field of view (FOV) and resolution. The diagonal FOV and resolution at a 35 mm working distance is 34 mm and 22 µm, and at a 10 mm working distance is 5 mm and 3 micrometers. A slider was chosen to enable fine adjustments with a single hand, which is compatible with current clinical workflow. The button 112A can be pushed to enable switching between illumination with either white or green LEDs. The button 112B can be pushed to capture and save an image. The placement of buttons 112A and 112B were selected so that physicians can easily change the light source and capture an image with one thumb, which is compatible with current clinical workflow. Additionally, the buttons can be built on a membrane keypad 125 (FIG. 1D) that is adhered to the ABS plastic handle of the image device. The membrane keypad was selected because it is water-resistant, which enables the physician to wipe down the handle of the probe between patient uses.

FIGS. 1D and 1E illustrate different exploded views of the colposcope 100. Referring to FIGS. 1D and 1E, the handle 102 of the colposcope 100 is formed at least partially by a housing that is put together by housing parts or portions 114 and 116. The housing parts 114 and 116 can be ultrasonically welded together to form the handle 102 and house the electronic and mechanical components for operation of the slider 110 and the buttons 112A and 112B. Parts 114 and 116 were designed to be ultrasonically welded so that the handle 102 is water-resistant, which enables the physician to wipe down the handle of the probe between patient uses. The slider's 110 movement is operable by use of the retainer assembly, which is comprised of pin 120, washer 122 and spring 124. The compression forces produced by this assembly provide a liquid and dust tight seal without inhibiting the freedom of movement. Specifically, the retainer assembly enables the easy sliding motion of slider 110 and enables connection to sled 134, which allows the user to zoom in on different features of the cervix, while also providing a tight seal preventing liquid and particle infiltration into the handle. The housing may also be formed by an interface panel including the membrane keypad 125 that is operatively connected to the slider 110 and the buttons 112A and 112B. The housing clamshell housing is ultrasonically welded to ensure liquid and dust tight protection and doesn't depend on medical superglue or epoxy.

The housing may also contain a printed circuit board (PCB) and LED driver board 126 for implementing functionality as described herein. Specifically, the LED driver board 126 allows the manufacturer to program the lux levels of the three LED settings, low white, high white, green, blue light. The LED driver board can allow the user to switch between the three LED settings, low white, high white, blue, and green light to image acetic acid staining, Lugol's iodine staining, and vascular patterns in the organ tissue bed of interest (e.g. cervix or breast). With continuing reference to FIGS. 1D and 1E, the distal end of the colposcope 100 may be formed of the probe 128 and an end cap 130. The probe 128 and the end cap 130 may be fitted together. A PCB and camera 132 may be held inside the probe 128. A holder 146 may also be fitted inside the probe 128 for carrying various components, including the PCB and camera 132. The distal end may also include a light guide and diffuser 148 located within the end cap 130. The geometry of the light guide is significant in that the 3D design prevent image vignetting and eliminate environmental or stray light eliminating baffle and structurally supports the concentric LED PCB ring 150. A hydrophobic window 152 is mated to center of the light guide and diffuser 148 by a press fit and reinforced by a silicone O-ring and medical grade epoxy to prevent liquid and particle infiltration. Imaging quality is not compromised with the addition of these structural components validated by computational ray tracing and empirical validation testing.

The colposcope 100 features a waterproof design that enables the user to submerge the probe in chemical agents for high level disinfection between patient uses. Specifically, the LEDs and image sensor are housed in acrylonitrile butadiene styrene (ABS) plastic casing and small amounts of medical grade epoxy are applied between individual ABS parts. These materials were selected because they are compatible with submersion in chemical disinfection agents such as hydrogen peroxide, bleach, and Cidex, which enables rapid disinfection of the imaging device between patient uses. The handle 102 and/or the probe 128 may be formed of ABS and may be rigid.

Figure 3:
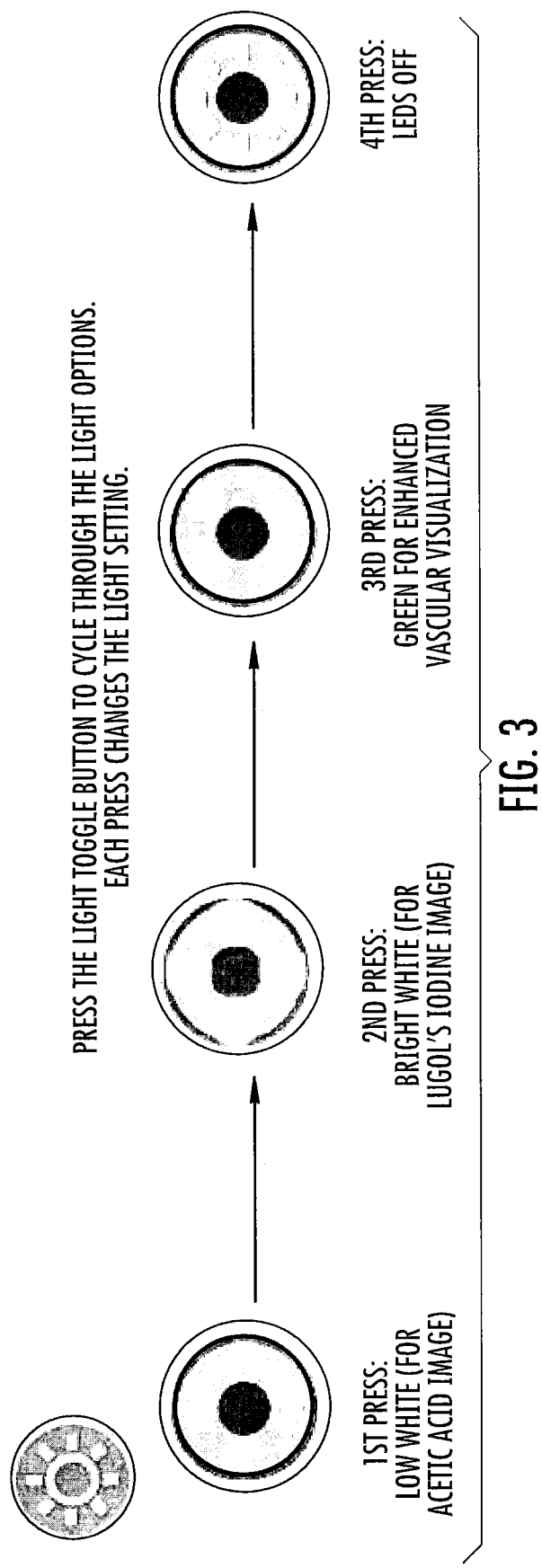
FIG. 3 illustrates the illumination sequence of the colposcope of FIGS. 1A-1F integrated into clinical workflow in accordance with embodiments of the present disclosure.

The ranges of illumination should be between 100 to 650 lux for acetowhitening imaging, 1000 to 5000 lux for Lugol's Iodine imaging, and 250 to 1250 lux for enhanced vascular visualization (green mode). These ranges are based on empirical validation in the pilot clinical studies conducted with the device and from computational modeling. In one embodiment the illumination sequence is shown in FIG. 3. If more rejection of specular reflection (unwanted glare from the cervix) is desired, another embodiment of the device would include a pair of orthogonally oriented linear polarizers made from thin plastic film and/or laminated glass, forming a cross polarized illumination and collection pathways. Further, filters (e.g., polarizers) may be used as disclosed herein for reducing specular reflection due to the moist nature of the cervix.

Figure 4:
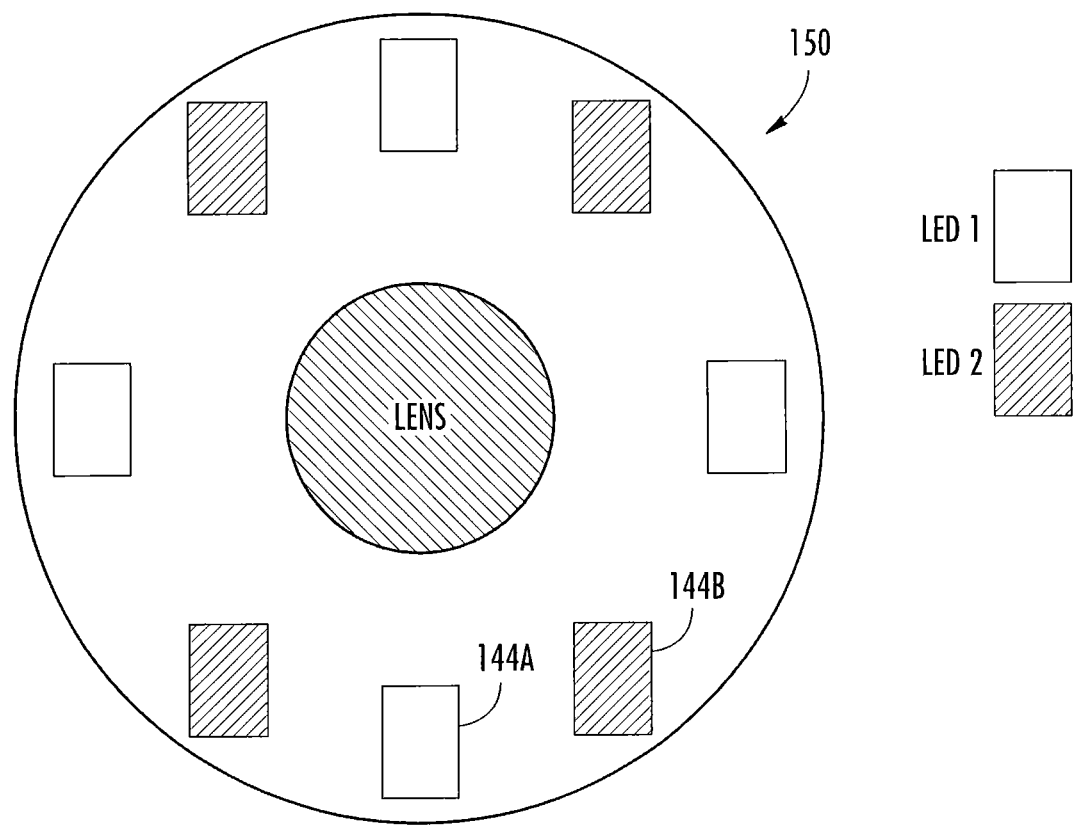
FIG. 4 illustrates a concentric ring LED illumination scheme for the colposcope of FIGS. 1A-1F in accordance with embodiments of the present disclosure.
Figure 5B:
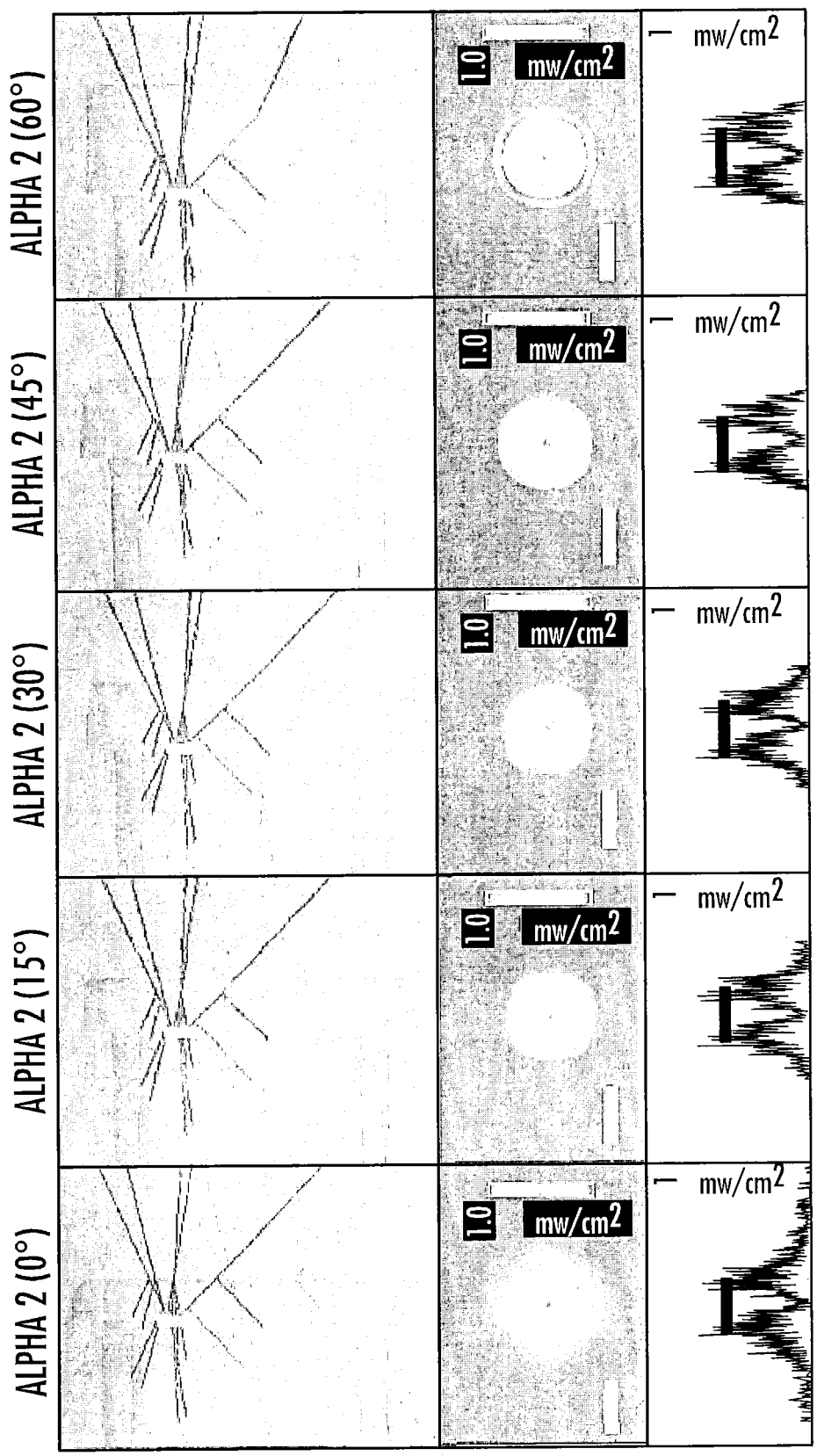
Figure 5C:
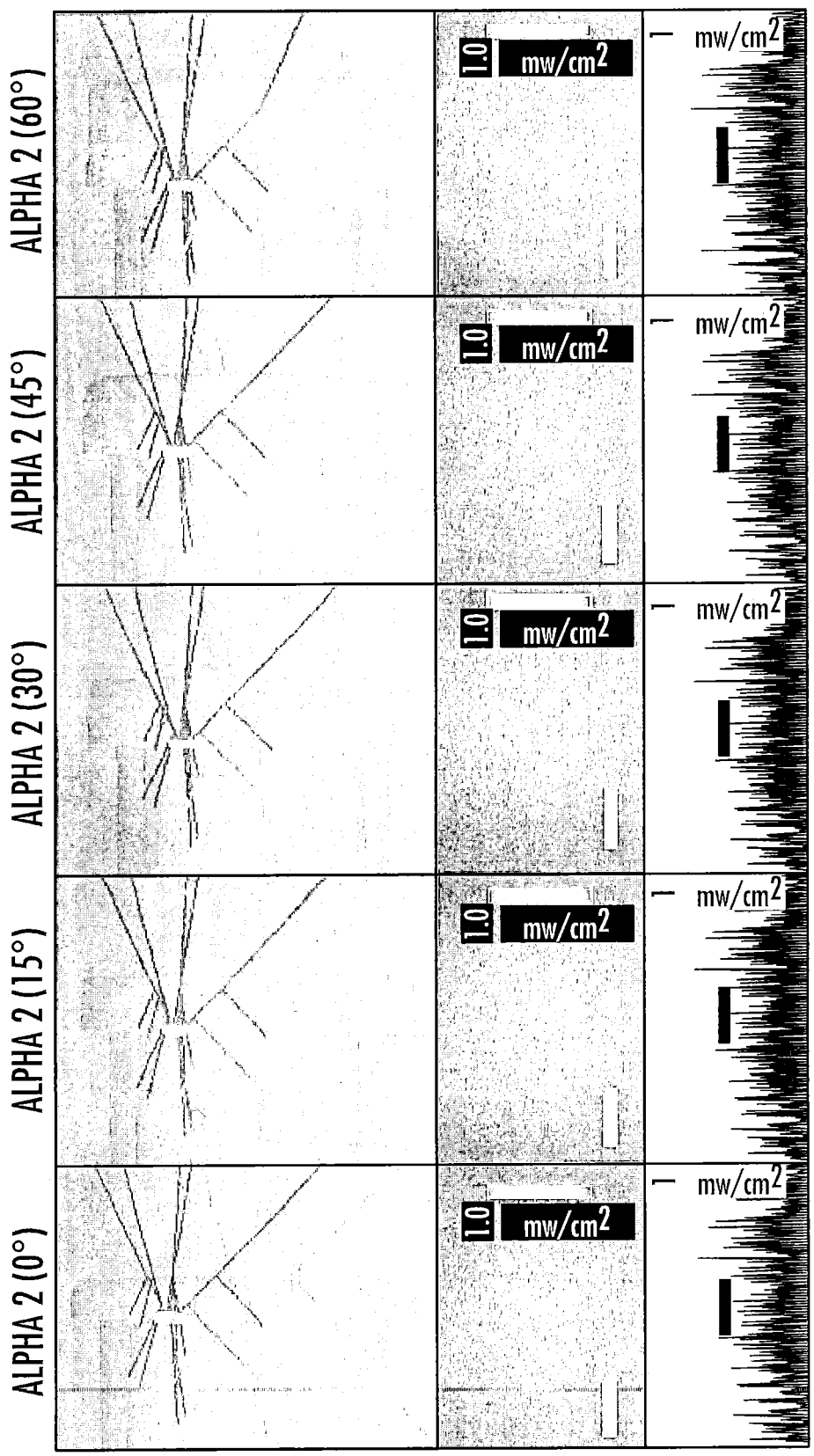
Figure 5D:
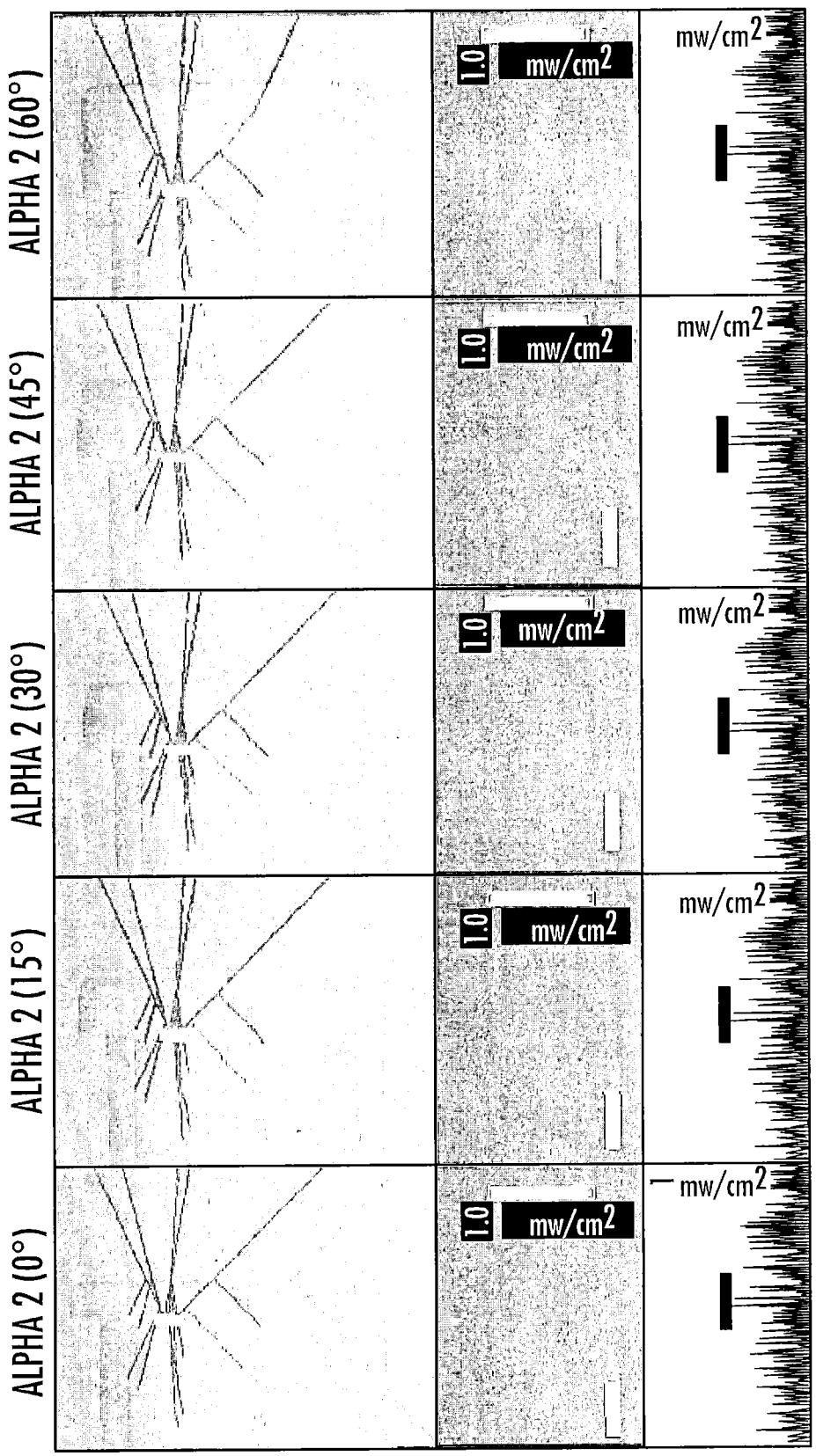
Figure 5E:
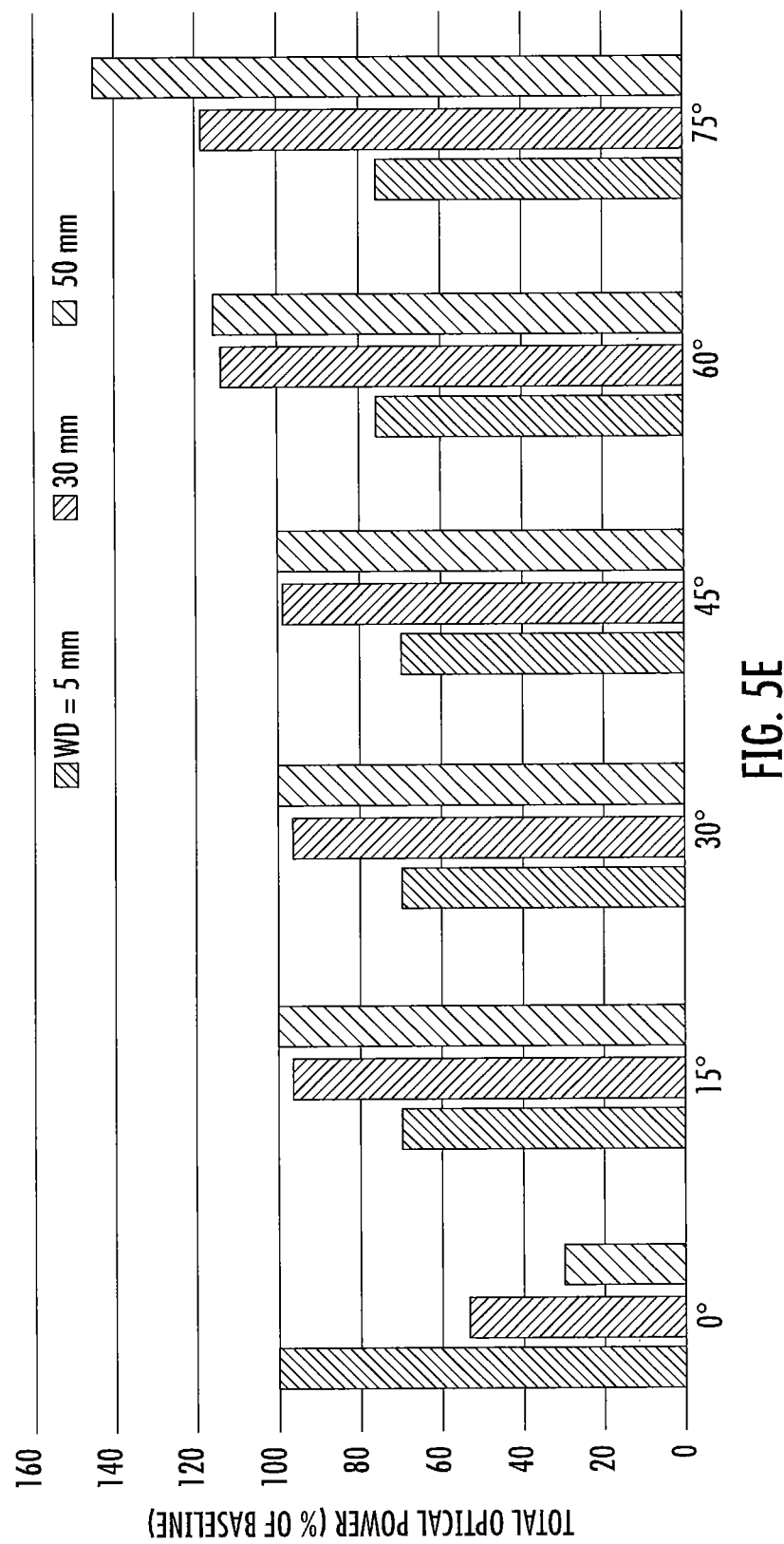

FIG. 4 illustrates the concentric ring 150 illumination scheme with an alternating sequence of white 144A and lime-green 144B according to some embodiments of the colposcope 100. The LEDs 144A, 144B have a divergent angle of 120-140 degrees and are radially spaced at approximately four congruent quadrants for even illumination. The LEDs 144A, 144B are evenly spaced apart circumferentially also for even illumination.

The color CMOS (complementary metal-oxide-semiconductor) or color CCD (charged couple device) is paired with a 4 to 5 element prime lens configuration, and a back focal length of between 2 to 5 mm. The prime element lens system allows for a wide range of magnifications through simply changing the position of the lenses with respect to the detector. The systems f/# is between 2 and 3, with emphasis for wide angle imaging. The detector will have a pixel pitch of between 1 and 3 microns. In some embodiments the prime lens can include automatic focus using a voice coil module (VCM) or Micro-Electro-Mechanical-System (MEMS) to provide final focal control.

Referring to FIG. 1C, the colposcope 100 can range in length from 100 mm to about 250 mm in length to accommodate potential variations in female anatomy. In other embodiments, the device is about 150 mm to about 225 mm in length. In yet another embodiment, the device is about 175 mm to about 200 mm in length. The colposcope 100 has a fixed length. The diameter of the probe 128 can range from 5 mm to 25 mm to fit within a broad range of speculums.

Figure 1F:
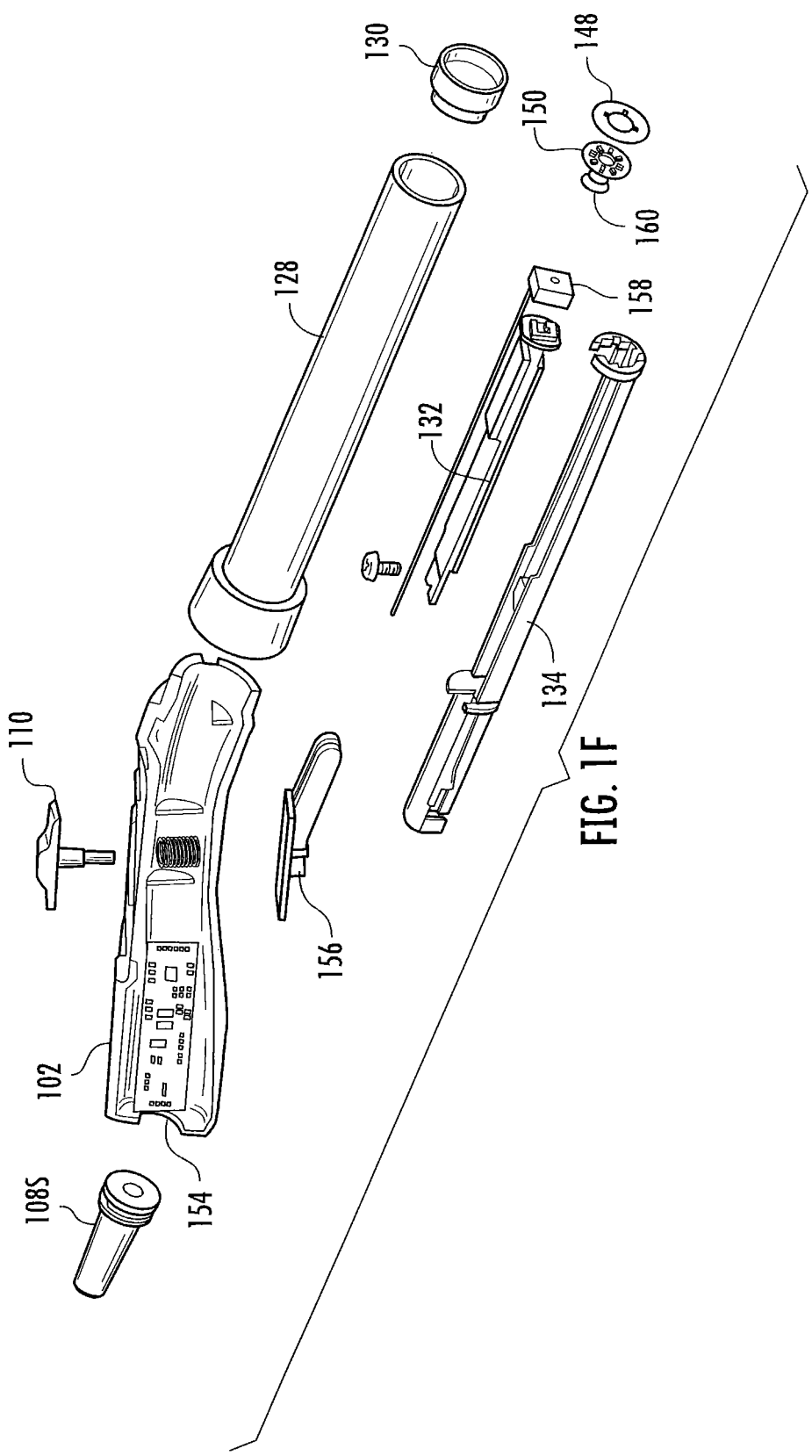

Features of the colposcope 100 according to some embodiments are further illustrated in FIG. 1F. A strain relief member 108S is coupled to the handle 102 and provides strain relief to the cable 108 that provides power for the LEDs and interfaces the camera to the electronic device (e.g., laptop or tablet). A microcontroller 154 is in an interior space of the handle 102 and includes or is operatively associated with the LED driver 126 (FIGS. 1D and 1E). The slider 110 interfaces with a slider connector 156 and the camera sled 134 to allow coarse magnification selection as described in more detail below. The color CMOS camera 132 is held in the camera sled 134 in an interior space of the probe 128. A five-element prime lens system 158 is adjacent the camera 132. A light baffle 160, the LED ring 150, and the LED light guide and diffuser 148 may be held within the end cap 130.

Figure 1G:
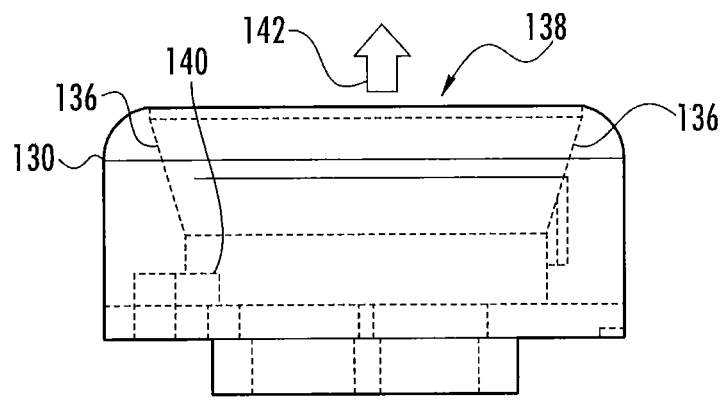
FIG. 1G is a side cross-sectional view of an end cap for use with a colposcope in accordance with embodiments of the present disclosure.
Figure 1H:
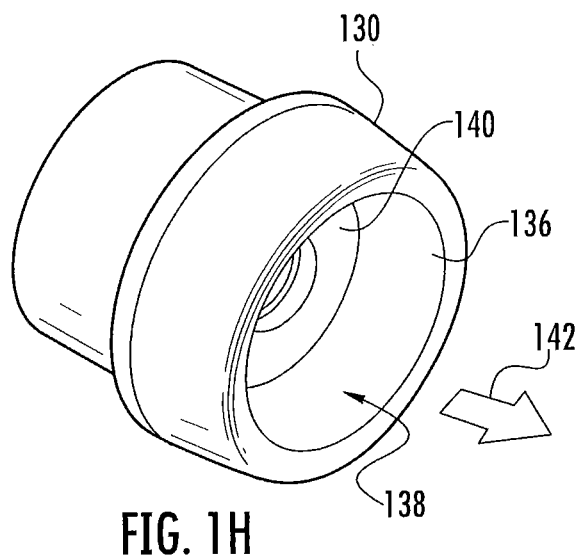
FIGS. 1H-1N are perspective views of example end caps in accordance with embodiments of the present disclosure.

The end cap 130 may be suitably configured for illuminating an object to be imaged. For example, FIG. 1G illustrates a side cross-sectional view of an end cap 130 for use with a colposcope, such as colposcope 100 show in FIGS. 1A-1F, in accordance with embodiments of the present disclosure. FIG. 1H illustrates a perspective view of the end cap 130 shown in FIG. 1G. Referring to FIGS. 1G and 1H, the end cap 130 may include a reflective surface 136 that extends around edges of a recess 138 within the end cap 130. The reflective surface 136 may be made of any suitable reflective material, such as a metal. The reflective surface 136 may be positioned and configured to receive light emitted by light emitters situated within the end cap 130. For example, the light emitters may be one or more LEDs positioned along a surface 140 for emitting light in a direction generally indicated by arrow 142. It is noted that the direction indicated by arrow 142 is also the general direction of a field of view of the image capture device (e.g., camera) of the colposcope. Thus, the light emitters are positioned to illuminate objects within the field of view of the light capture device.

In the example of FIGS. 1G and 1H, an end cap is shown having a reflective surface 136 angled at 75 degrees with respect to an axis of the body of the colposcope. Further, the length of the reflective surface is 4.5 millimeters. The reflective surface 136 can refocus light normally lost outside the region of interest in a uniform matter.

Figure 1I:
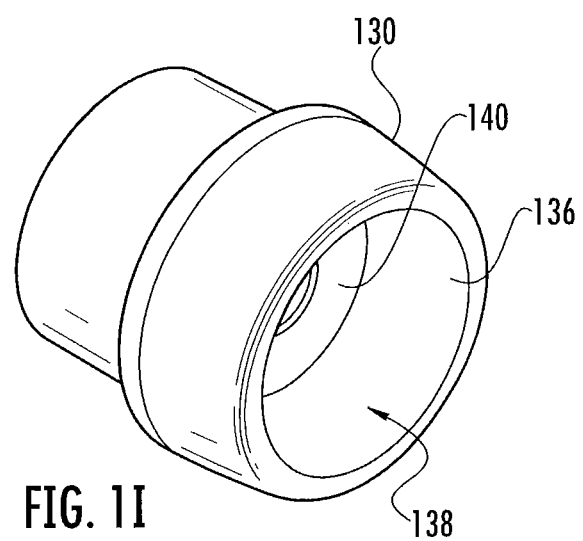
Figure 1J:
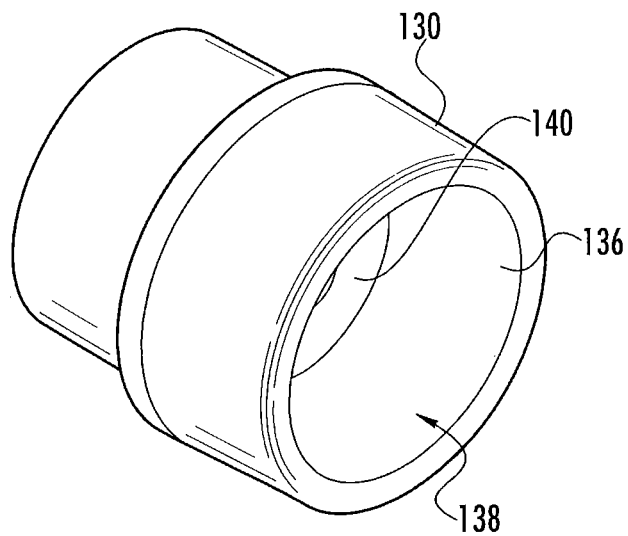
Figure 1K:
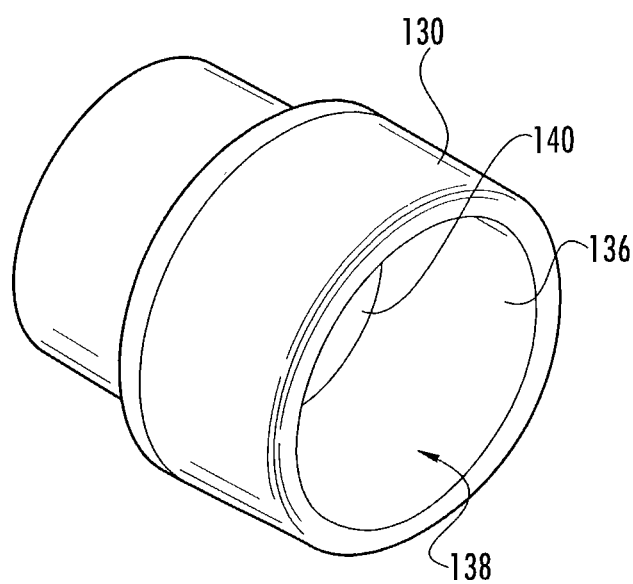
Figure 1L:
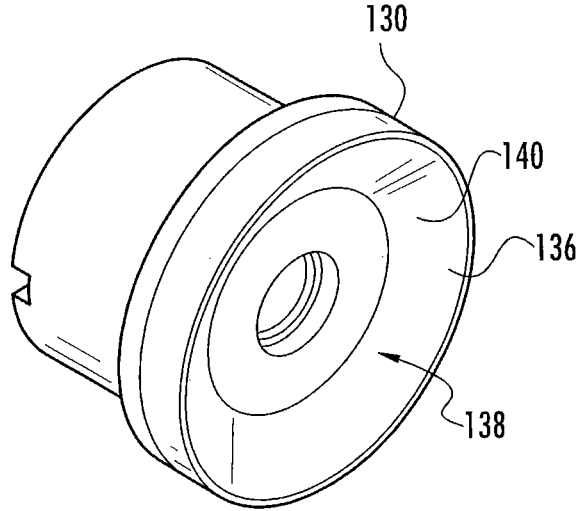
Figure 1M:
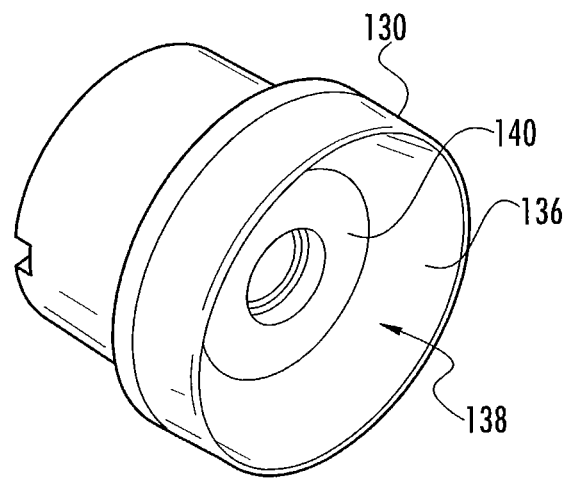
Figure 1N:
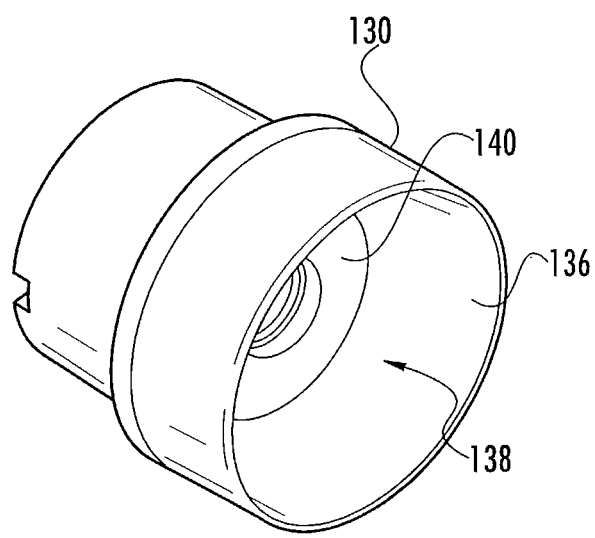

In alternative embodiments of the end cap, the reflective surface of an end cap may be configured differently than the reflective surface 136 shown in FIGS. 1G and 1H. For example, FIGS. 1I-1N illustrate perspective views of other example end caps 130 in accordance with embodiments of the present disclosure. Particularly, FIG. 1I shows an end cap 130 with a reflective surface 136 angled at 75 degrees and a length of 5.5 millimeters. FIG. 1J shows an end cap 130 with a reflective surface 136 angled at 75 degrees and a length of 6.5 millimeters. FIG. 1K shows an end cap 130 with a reflective surface 136 angled at 75 degrees and a length of 7.5 millimeters. FIG. 1L shows an end cap 130 with a reflective surface 136 angled at 30 degrees and a length of 1.8 millimeters. FIG. 1M shows an end cap 130 with a reflective surface 136 angled at 45 degrees and a length of 3.0 millimeters. FIG. 1N shows an end cap 130 with a reflective surface 136 angled at 60 degrees and a length of 5.5 mm.

Experiments were conducted with end caps as shown in FIGS. 1G-1N. FIGS. 5A-5E are various images showing results of such experiments, where the reflector improves the beam uniformity across working distances when compared to the bare and lower angle reflectors.

A magnification adjustable continuous zoom mechanism according to some embodiments is illustrated in FIG. 6. The continuous magnification control that is provided by a user controlled camera sled mechanism, where optical zoom can be achieved by linear translation of the camera or detector with respect to the fixed prime lens system. This allows the colposcope 100 to provide a broad range of field of views of 6-54 mm and a resolution of 4-40 µm, and at working distances of 5-50 mm, respectively, without the need for multiple expensive objective lenses. The user can control magnification by sliding a toggle that is connected to the camera sled mechanism, and optical zoom can be achieved by linear translation of the detector with respect to the fixed prime lens system for continuous magnification between 3 and 52×. The slider mechanism is watertight with low actuation force achieved by ultralow friction PTFE films compressing a rubber gasket held under compression with a constant force wave spring. The position or magnification selected is monitored with a noncontact magnetic digital linear potentiometer, where displacement of the camera sled moves an embedded miniature magnet across the potentiometer causing a linear change in voltage, which is read by a microcontroller in the probe handle. An autofocus mechanism for fine adjustment is made by a VCM (voice coil module) and controlled by the microcontroller.

The coarse focus adjustment mechanism allows the user to select from 3 to 52× magnification by linear translation of the slider 110. The slider 110 is connected to the slider connector 156 which is connected to the camera sled 134 that holds the CMOS color camera detector 132. Therefore, the linear translation of the slider causes linear translation of the camera 132 and the camera sled 134 with respect to the fixed prime lens module, system, or unit 158 (FIG. 1F). The magnification read by a linear digital potentiometer 162 translates the displacement of the embedded magnet 164 in the sled 134 as a change in voltage. An autofocus mechanism for fine adjustment is made by a VCM (voice coil module) (FIG. 7) and controlled by the on-board microcontroller 154.

Figure 7:
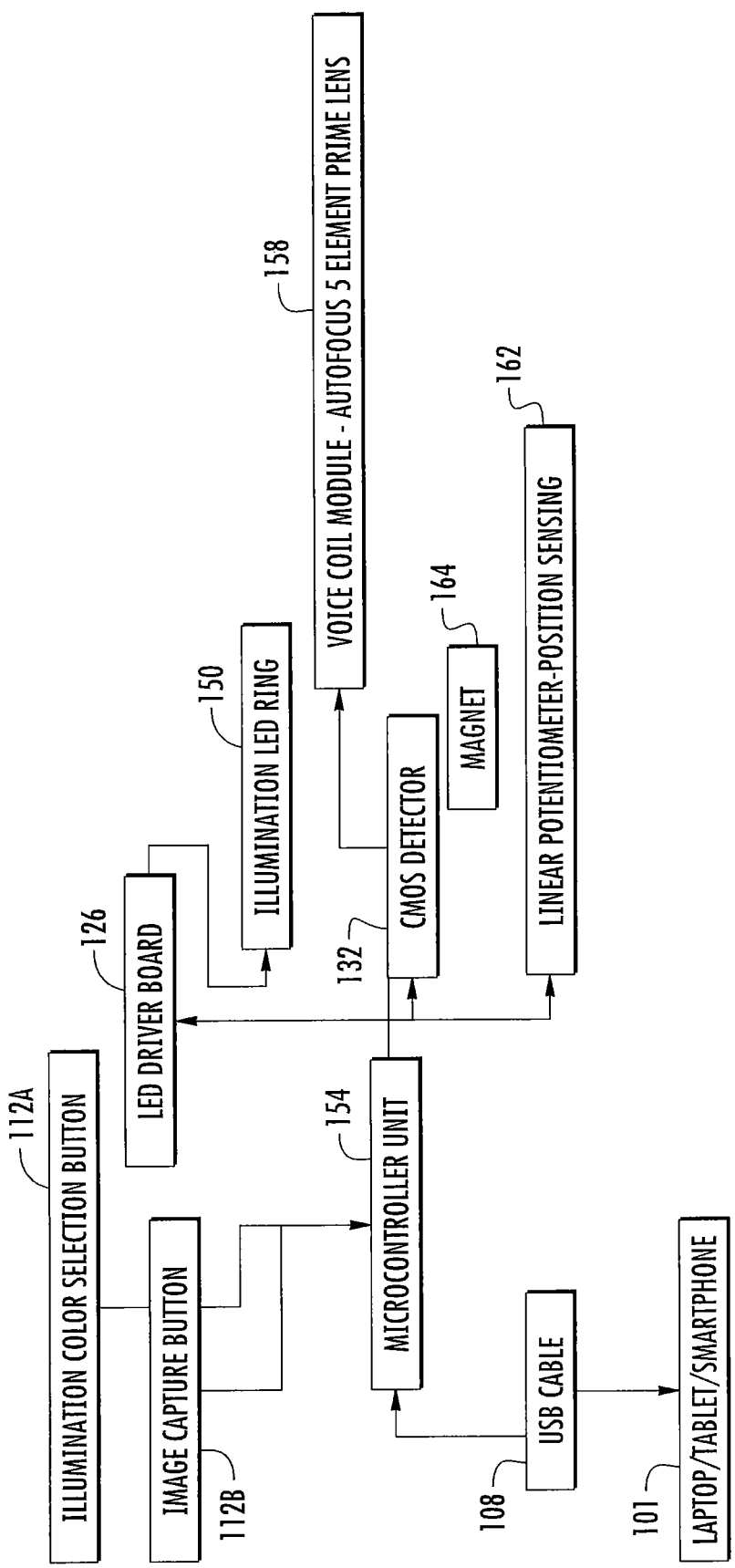
FIG. 7 is a block diagram illustrating features of the colposcope of FIGS. 1A-1F, 6, and 7.

FIG. 7 is a block diagram that illustrates some of the components of the colposcope 100 described herein.

In accordance with embodiments, a colposcope as disclosed herein can be modified for use as a mammoscope. In an example, the white LEDs at the distal end of the probe can be replaced with blue LEDs and a bandpass filter can be placed in front of the camera lens for fluorescence imaging.

Figure 8A:
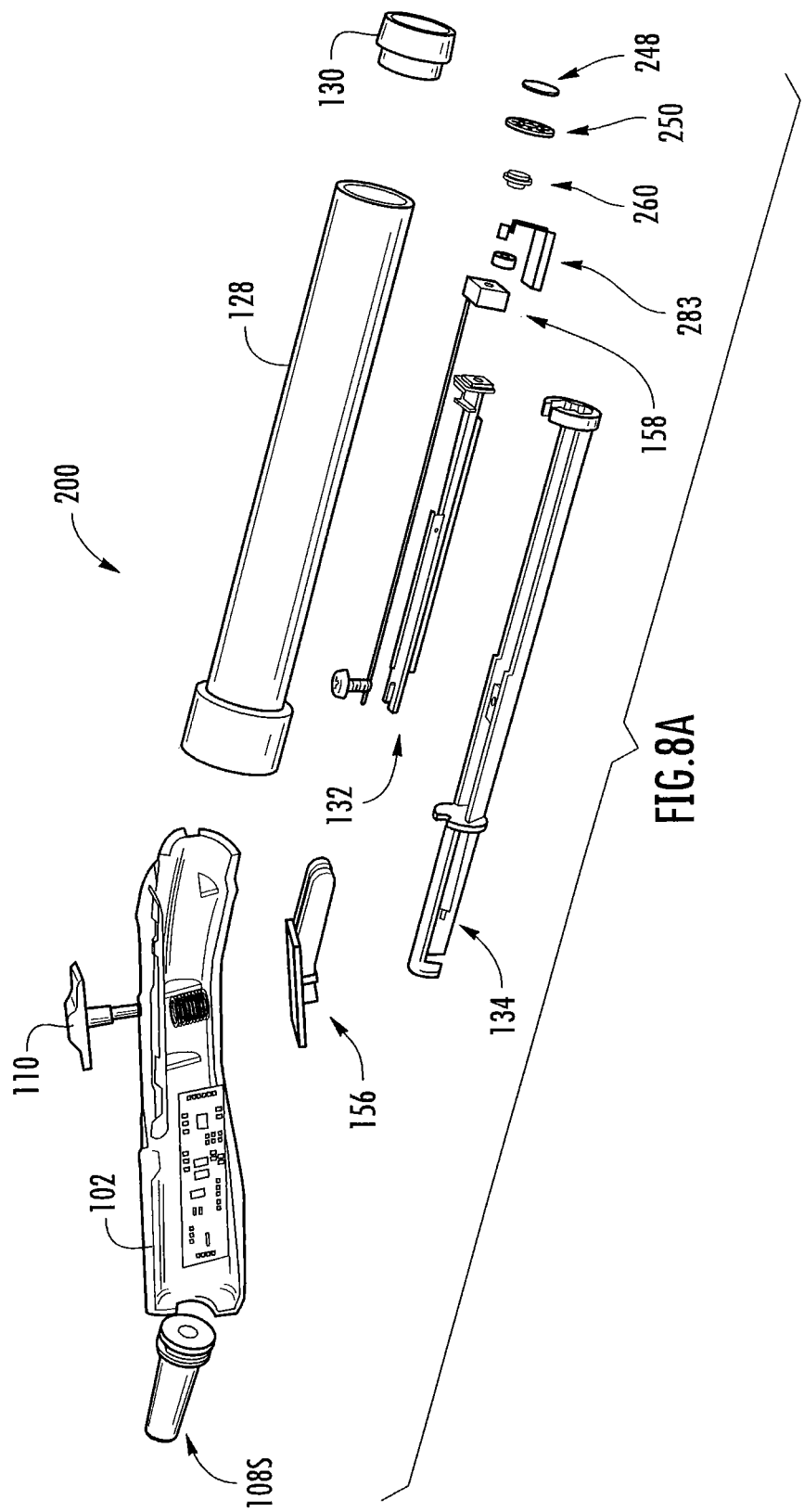
Figure 8B:
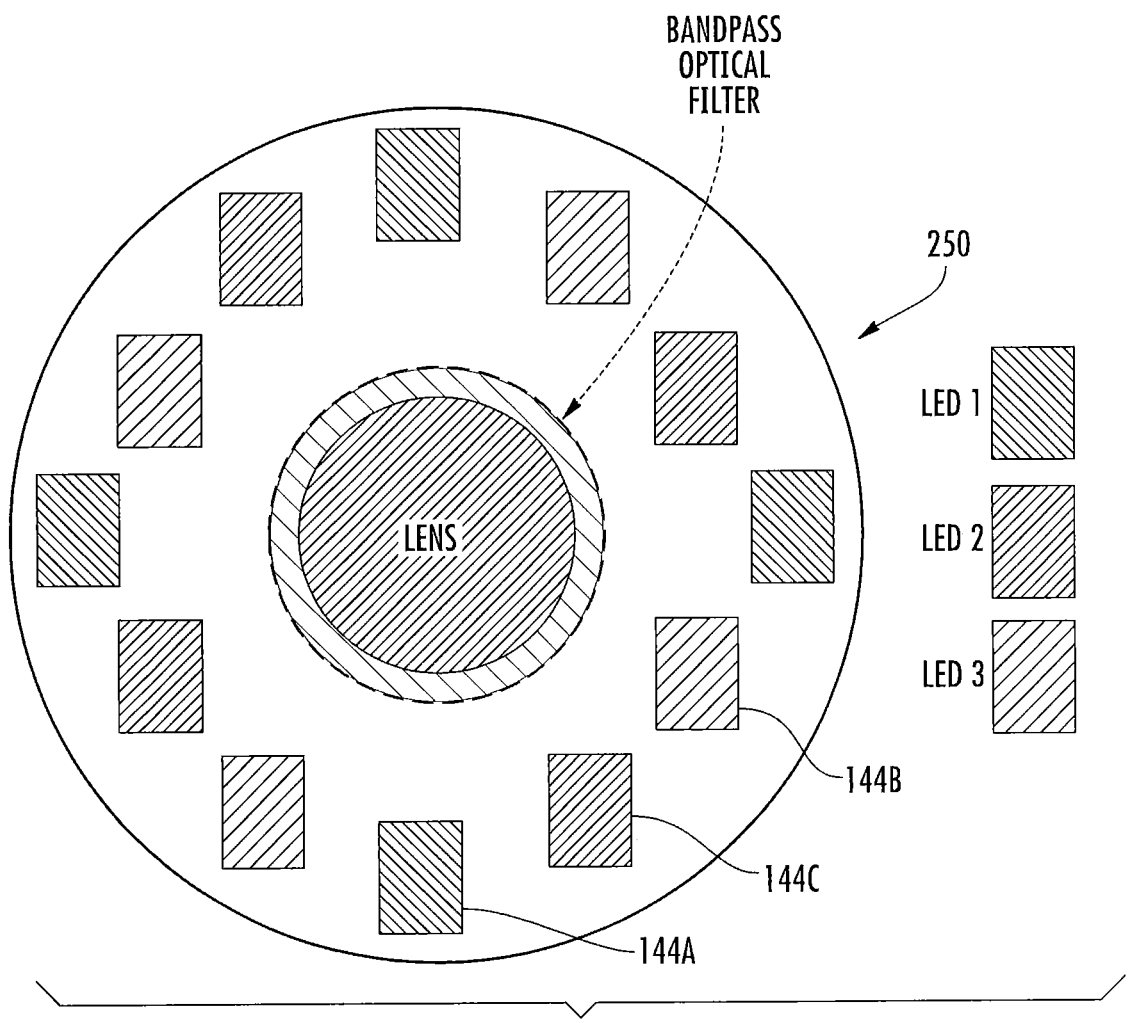
FIGS. 8B and 8C illustrate fluorescent concentric ring LED illumination schemes in accordance with embodiments of the present disclosure.
Figure 8C:
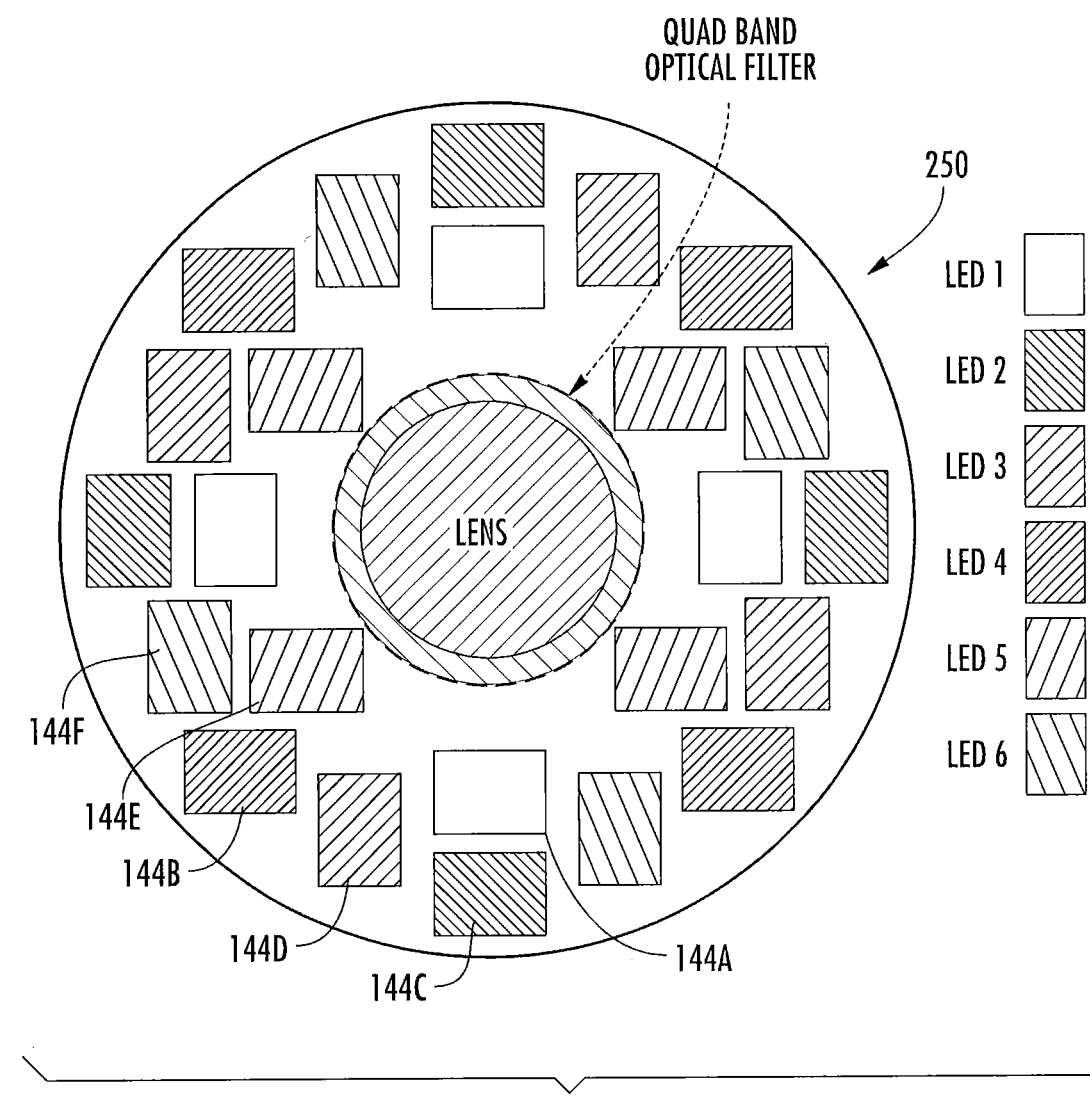
Figure 8E:
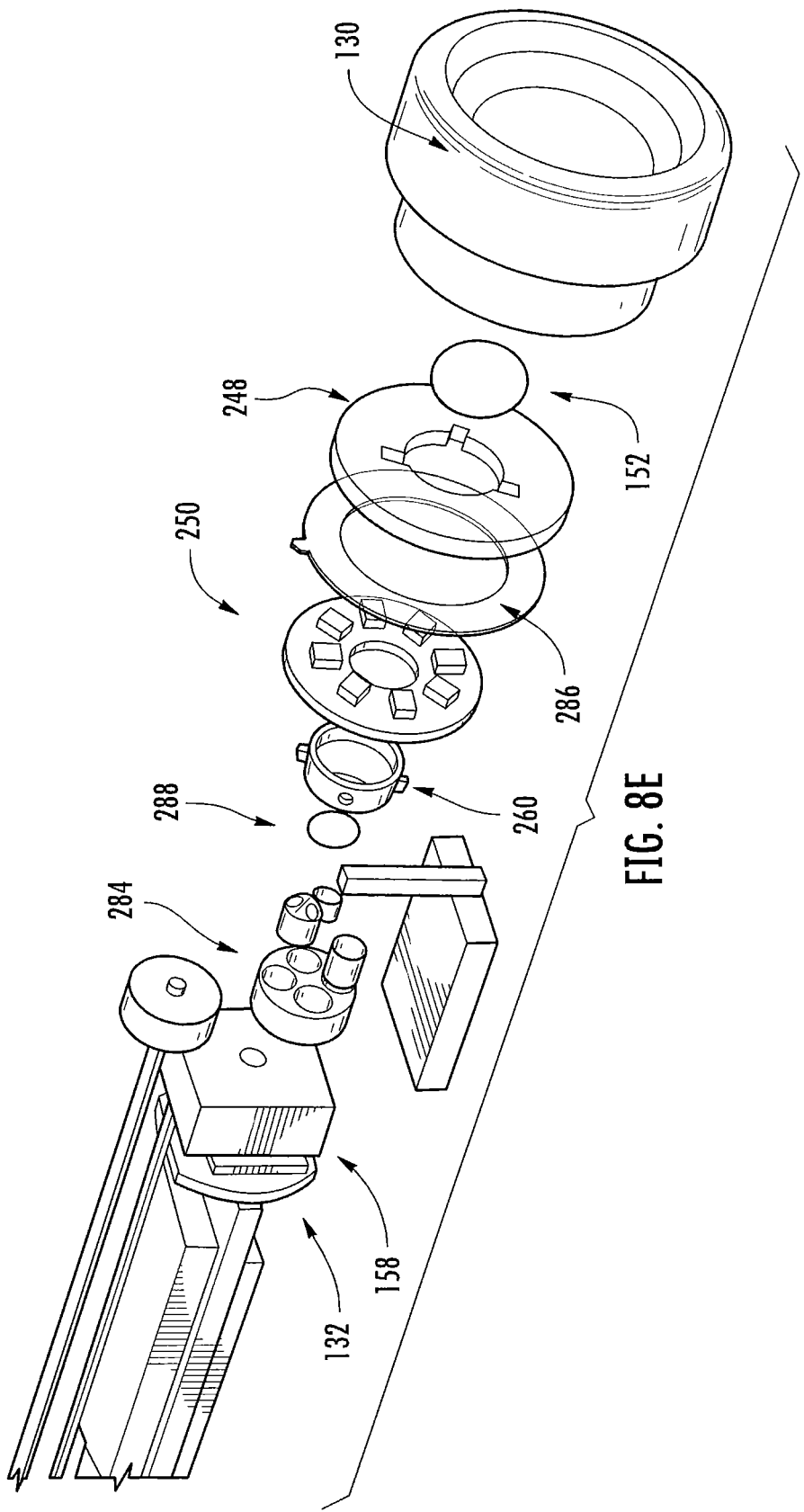

FIGS. 8A, 8D, and 8E are exploded views of an example mammoscope 200 in accordance with embodiments of the present disclosure. The mammoscope 200 can be used for both vascular (reflectance) and metabolic (fluorescence) imaging. The mammoscope 200 can image vascular features at wide field and capillary level resolution and fluorescent beads (10-µm) with a CNR greater than 200:1.

The mammoscope 200 includes several components that are common to the colposcope 100 as designated by the reference numbers. For example, the mammoscope 200 includes the handle 102, probe 128, camera 132 (e.g., a 5-megapixel color CMOS camera with 1.4 µm pixel pitch), sled 134, and the 5-element prime, aspheric, injection molded lens system 158 with an integrated voice coil module (VCM) that allows for fine autofocus. The mammoscope 200 may also employ the coarse magnification control that is provided by the user controlled camera sled mechanism, where optical zoom can be achieved by linear translation of the camera or detector with respect to the fixed prime lens system. This allows the mammoscope 200 to provide a broad range of FOVs of 6-54 mm and a resolution of 4-40 µm, and at working distances of 5-50 mm, respectively, without the need for multiple expensive bulky objective lenses typically required for multiple magnifications.

Furthermore, recent advances in LED technology enables our design to use efficient, compact (2.2 mm² surface area), high powered LEDs in a concentric ring design that enables for uniform reflectance and excitation illumination through an alternating sequence of single color LEDs radially spaced at even intervals around the perimeter of the entrance aperture, without the need for a cumbersome and slow excitation filter wheel or expensive electronic liquid crystal tunable filter. Referring to FIG. 8B, the concentric ring LED 250 illumination scheme includes an alternating sequence of white, green, and blue LEDs 144A, 144B, 144C for FITC excitation. Selective illumination can be achieved without the need of physically filtering a broadband source by individual constant current drivers for each individual LED multiplex to a microcontroller to handle selective control for intensity and selection of the desired illumination. A single bandpass optical emission filter allows for discrete fluorescent imaging of a single target fluorophore. The LEDs have a divergent angle of 120-140° and are radially spaced at approximately 4 congruent quadrants for even illumination. The LEDs 144A, 144B, 144C may be evenly spaced apart circumferentially also for even illumination.

In another embodiment, as shown in FIG. 8C, the concentric ring LED illumination scheme includes an alternating sequence of white, blue, cyan, green, amber, and orange LEDs 144A, 144C, 144D, 144B, 144E, 144F for multi-fluorophore excitation. Selective illumination can be achieved without the need of physically filtering a broadband source by individual constant current drivers for each individual LED multiplex to a microcontroller to handle selective control for intensity and selection of the desired illumination. A quad band emission filter allows for discrete fluorescent imaging of multiple fluorophores. The LEDs have a divergent angle of 120-140° and are radially spaced at approximately 4 congruent quadrants for even illumination.

Referring to FIGS. 8A, 8D, and 8E, the imaging pathway starts with the CMOS camera 132 followed by the autofocus lens module 158. Band pass filters matched to the emission peaks of, for example, 2-NBDG (540 nm) and TMRE (580 nm) are used for fluorescence detection with a motorized micro filter wheel 284 which are rotated into the imaging axis pathway by a micro-stepper motor in the handle 102 which changes the filter wheel circular orientation to the desired filter as controlled by the microcontroller. A clear or open filter slot is allocated for filter-free reflectance imaging. We also propose a design on the geometry of the light baffle 260 which acts as a physical entrance aperture with an opaque light absorbing coating to prevent image vignetting and eliminate environmental or stray illumination light from the concentric LED ring 250. Specular reflection (glare) rejection will be addressed using cross-polarization which is achieved by placing a thin film linear polarizer 286 over the excitation LEDs that is orthogonally oriented to a high-contrast glass linear polarizer 288 placed in front of the lens module 158. A hydrophobic window 152, to reduce fogging and protect the optical components, is mated to center of the polycarbonate LED light guide 248 via a press fit locking mechanism and reinforced by medical grade epoxy to prevent liquid and particle infiltration. The light guide 248 acts as a light pipe conduit for the LEDs to a reflector tip 130 and protects the LEDs from environmental exposure. The reflector tip 130 is designed to structurally support the concentric LED PCB ring 250 and maximize uniform illumination onto the tissue or sample surface. When compared to our initial fluorescent imaging prototype, the proposed mammoscope 200 is self-contained and more resilient to environmental conditions with the protected internal filter wheel and expanded capability of multiple fluorophore imaging and multicolor reflectance imaging not previously achievable.

Referring to FIG. 8A, in more detail, the mammoscope 200 includes the strain relief member 108S that provides strain relief to the cable 108 that can provide power to the LEDs and interfaces the camera 132 to an electronic device such as the electronic device 101 shown in FIG. 1A (e.g., laptop, smartphone, tablet). The microcontroller unit 154 is held in the handle 102 and may include or control the LED constant current drivers. The slider 110 is connected to the slider connector 156 which is connected to the camera sled 134 to allow for coarse magnification selection as described above. The camera 132 is held in the sled 134 and held in the probe shaft 128. The five-element prime lens system with autofocus 158 and/or the filter wheel assembly 283 may be held in the probe 128. The light baffle 260, the LED ring 250, and/or the light guide 248 may be held in the end cap or reflector tip 130.

The filter wheel assembly 283 is illustrated in greater detail in FIG. 8D. The filter wheel assembly 283 includes a filter wheel mount with spindle 290, the custom filter wheel 284 coupled to the filter wheel mount 290, and a plurality of custom optical filters held in the filter wheel 284. The filters may include a TRITC filter 291, a DAPI/Hoescht filter 292, and a FITC bandpass filter 293. A clear bright field optical window 294 may also be held in the filter wheel 284.

In accordance with embodiments, the disclosed subject matter may be used to establish wide-field, high-resolution, visualization strategies, automated segmentation algorithms, and a fluorescently antibiotics to enhance specificity of the system. In an example, a colposcope having features disclosed herein may be adapted to function as a mammoscope. The mammoscope may be a portable wide-field, high-resolution imaging system utilizing a fluorophore for visualization and treatment of residual disease during BCS. The sensitivity and specificity of the mammoscope to detect fluorescence may be established as a function of progressively decreasing tumor cell density in a pre-clinical model of breast cancer.

In accordance with embodiments, the present subject matter relates to colposcopy. For example, inserters are described herein that utilize the principle of a mechanical delivery method for insertion and stabilization into the vagina for imaging of the external cervix. The imaging may produce digital, color, high-resolution images at both full field and at high magnification of areas of interest. Inserters described herein may include an image capture device for capture and storage of high-resolution, multimodal images of the external cervix for post-hoc analysis by medical personnel at a centralized location. In accordance with embodiments of the present disclosure, an inserter, a colposcope and electronic device may be a part of a kit provided for use by medical personnel to allow for screening of patients.

Figure 9A:
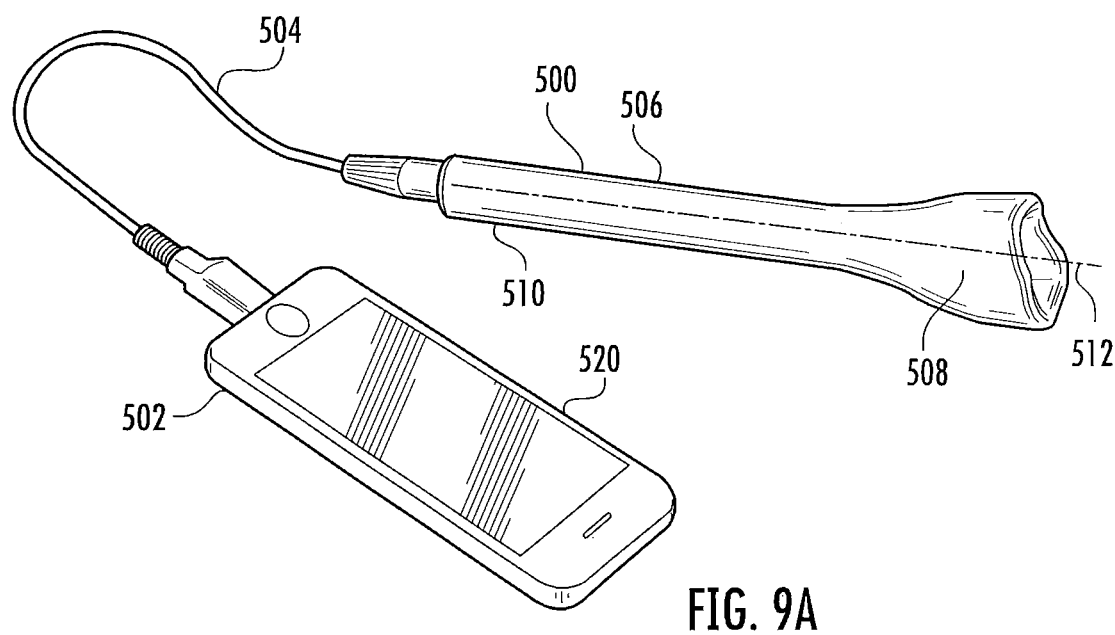
FIG. 9A is a perspective view of a colposcope with speculum-free imaging device (inserter) and an electronic device in accordance with embodiments of the present disclosure.

FIG. 9A illustrates a perspective view of a speculum-free imaging device (inserter with colposcope) 500 and an electronic device 502 in accordance with embodiments of the present disclosure. Referring to FIG. 9A, the colposcope within the inserter 500 and electronic device 502 are communicatively connected by a cable 504. In this example, the colposcope 500 and electronic device 502 communicate in accordance with the universal serial bus (USB) standard. Alternatively, the inserter 500 and electronic device 502 may communicate by another suitable communications standard.

The inserter 500 includes an elongate body 506 having a distal end 508, a proximate end 510, and an axis indicated by broken line 512. The body 506 is generally tubular and rounded in shape. Alternatively, the body 506 may be of any suitable shape and size.

Referring to the distal end 508, this end has a curved funnel-like tip. The curved tip enables easy manipulation of the cervix, especially in cases where the patient has a tilted uterus. In this example, the device has a slim tubular body that can range between 1 centimeter to 1.5 centimeters to enable accommodation of the camera through the channel while still preserving patient comfort. The tubular body opens up to a curved funnel-like tip which can range between about 2.5 centimeters and about 3.5 centimeters in diameter (range of anatomical cervix diameter). The tip may be curved (a variable s-curve) and funnel like for enabling a fit with the curvature of the cervix and protrudes on one end to scoop the cervix in place can function the same way.

The body 506 can define an internal space or channel through which a camera (not shown) with LED illumination (e.g., a 2MP mini USB camera) to enable cervix image capture. The light and camera feature allows for an image of the cervix to be lit and captured. Further, the internal space of the body 506 or channel may also enable acetic acid/Lugol's iodine application and insertion of swabs for Pap smear sample collection. The camera can be connected to the electronic device 502 for image capture. The colposcope including the inserter 500 can provide for patient-centered colposcopy and can also be used to center and identify the cervix for physician-based or self-Pap/HPV testing.

Figure 9B:
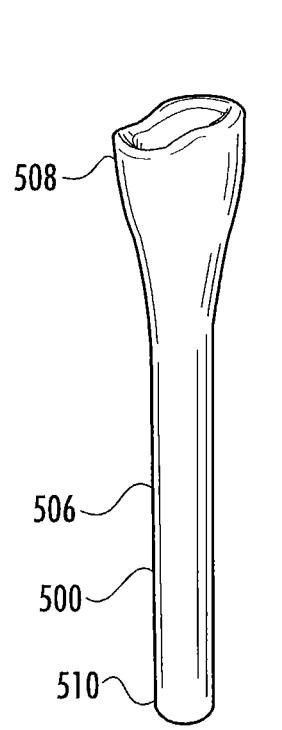
FIG. 9B is a perspective view of the inserter shown in FIG. 9A.
Figure 9C:
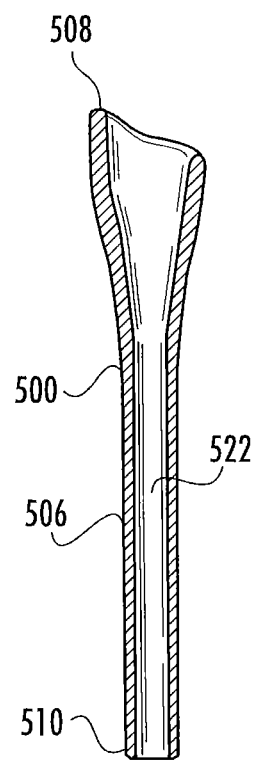
FIG. 9C is a cross-sectional side view of the inserter shown in FIG. 9B.

FIGS. 9B and 9C illustrate a perspective view and a cross-sectional side view, respectively, of a body of the colposcope 500 shown in FIG. 9A. The proximate cylindrical end 510 has a length ranging from 5 cm to 25 cm, with a diameter ranging from 0.5 cm to 3 cm. The distal end 508 extends in a funnel-like shape with a diameter ranging from 0.5 cm to 5 cm and a length ranging from 2 cm to 10 cm. The distal end has a lip in an s-shaped curve that extends from the main body within a range of 0.1 cm to 5 cm; the width of this lip ranges from 0.1 cm to 5 cm. The addition of a lip to the inserter enables the manipulation of the cervix to properly position the cervix to visualize the cervix in women with varying cervical tilts. Additionally, the ranges in the length of the device is necessary for applicability to different patient populations; women with varying vaginal canal and cervix lengths.

Referring particularly to FIG. 9C, the body may form an interior channel 522 or other interior space. An image capture device, such as a waterproof, 2 megapixel, may be suitably positioned and attached inside the channel 522. In an example, the camera may have four white LEDs for illumination and a lens covered by an anti-reflection coated hydrophobic window. The associated colposcope may be configured to have adjustable brightness and a manual focus. Electronics for image capture and lighting may be housed in a metallic body of the image capture device (e.g., camera). The electronics may interface via a USB cable to a phone, tablet, or computer, all of which provide power to the camera and enable image capture. Thus, the camera may only require a charged phone, tablet, or computer to operate, but does not require AC power or a separate battery source. The cable may have a length of between 1 to 3 meters to allow for variations in hospital room and/or clinic room set up. The USB cord is a light and nonintrusive way to power the camera and illumination components of the device. The cross-sectional view of the inserter shows an increasing thickness from the bottom to the tip. This enables preservation of the slim body while enabling a blunt, comfortable tip for introduction into the patient. The slanted curve of the tip also enables a gradual and hence more comfortable introduction as compared to a flat tip.

Figures 10A, 10B, 10C:
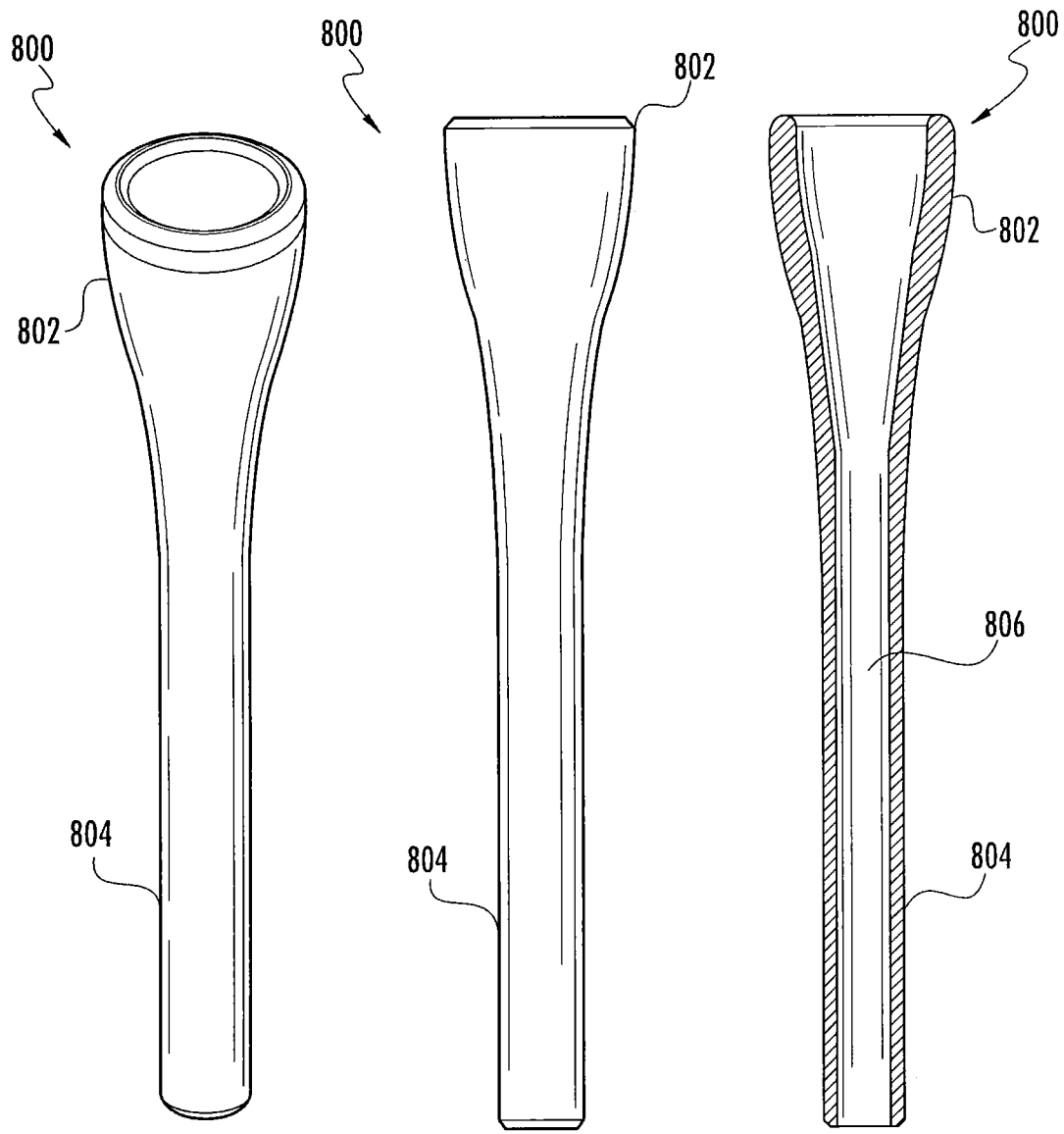
FIGS. 10A-10C are different views of a flat-tip inserter in accordance with embodiments of the present disclosure.
Figure 11A:
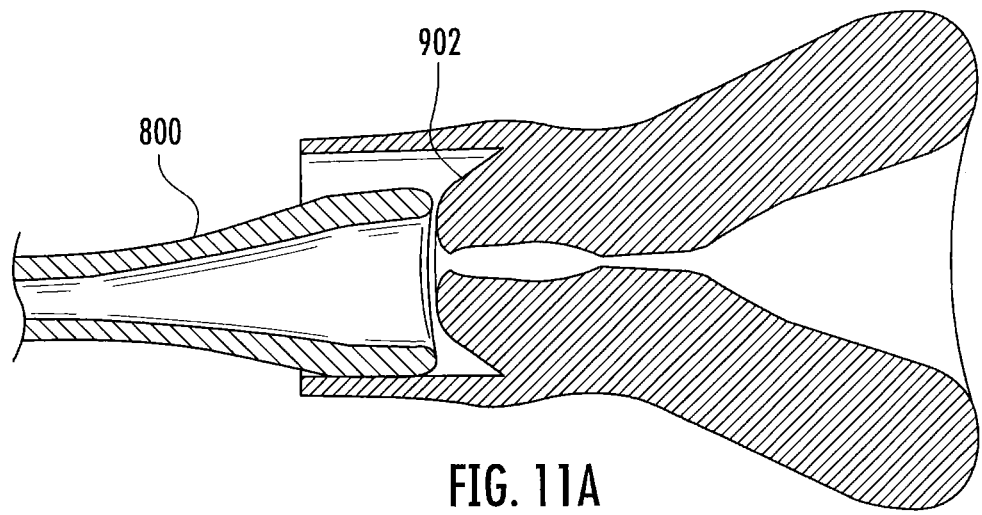
FIGS. 11A and 11B are cross-sectional side views showing using of a flat and curved end inserters, respectively, for manipulation of the cervix.
Figure 11B:
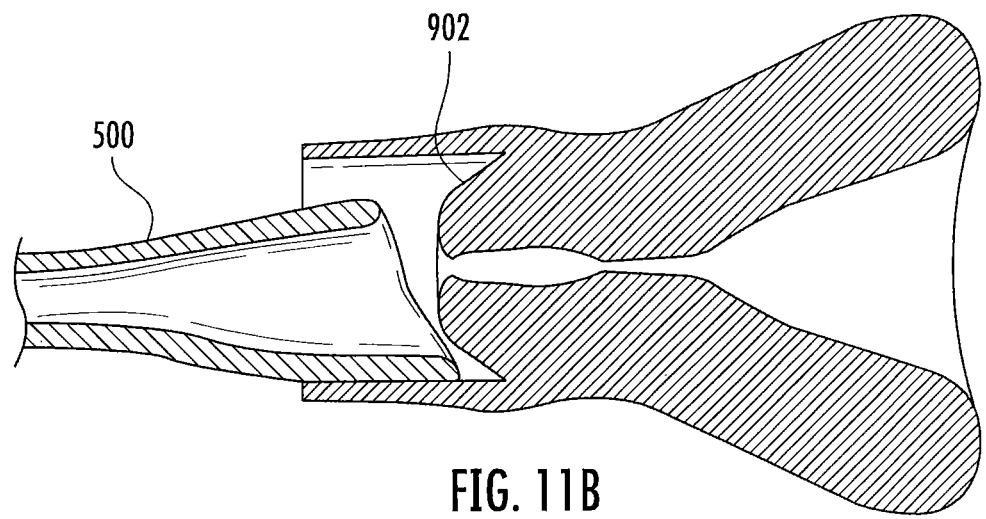

In another example, FIGS. 10A-10C illustrate different views of a flat-tip inserter 800 for use with a colposcope in accordance with embodiments of the present disclosure. Referring to FIG. 10, the inserter 800 includes a distal end 802 having a flat tip. The inserter 800 also includes a handle 804. The inserter 800 may be similar to the body shown in FIGS. 9A, 9B, and 9C except that the tip is flat rather than curved. An image capture device, such as a waterproof, 2 megapixel, CMOS color camera, may be positioned and fitted in an interior channel 806 of the inserter. In an example, the image capture device may have four white LEDs for illumination and a lens covered by a plane hydrophobic window. The LEDs may have adjustable brightness and a manual focus. Electronics for image capture and lighting may be housed in a metallic body of the camera. The electronics may interface via a USB cable to a phone, tablet, or computer, all of which provide power to the camera and enable image capture. Thus, the camera only requires a charged phone, tablet, or computer to operate, but does not require AC power or a separate battery source.

It is noted that in the embodiments of the inserter disclosed herein, the inserter may define an interior space that can serve as a working channel for camera placement, acetic acid application, and other features.

Referring to FIG. 9A, the electronic device 502 may be configured to control the operation of the colposcope 500, to process captured images, and to interface with a user, such as medical personnel. In this example, the electronic device 502 is a smartphone, although it should be understood that the electronic device 502 may alternatively be any other type of computing device. It is noted that the term "electronic device" should be broadly construed. It can include any type of device capable of presenting electronic text to a user. For example, the electronic device may be a mobile device such as, for example, but not limited to, a smart phone, a cell phone, a pager, a personal digital assistant (PDA, e.g., with GPRS NIC), a mobile computer with a smart phone client, or the like. An electronic device can also include any type of conventional computer, for example, a desktop computer or a laptop computer. A typical mobile device is a wireless data access-enabled device (e.g., an iPHONE® smart phone, a BLACKBERRY® smart phone, a NEXUS ONE™ smart phone, an iPAD® device, or the like) that is capable of sending and receiving data in a wireless manner using protocols like the Internet Protocol, or IP, and the wireless application protocol, or WAP. This allows users to access information via wireless devices, such as smart phones, mobile phones, pagers, two-way radios, communicators, and the like. Wireless data access is supported by many wireless networks, including, but not limited to, CDPD, CDMA, GSM, PDC, PHS, TDMA, FLEX, ReFLEX, iDEN, TETRA, DECT, DataTAC, Mobitex, EDGE and other 2G, 3G, 4G and LTE technologies, and it operates with many handheld device operating systems, such as PalmOS, EPOC, Windows CE, FLEXOS, OS/9, JavaOS, iOS and Android. Typically, these devices use graphical displays and can access the Internet (or other communications network) on so-called mini- or micro-browsers, which are web browsers with small file sizes that can accommodate the reduced memory constraints of wireless networks. In a representative embodiment, the mobile device is a cellular telephone or smart phone that operates over GPRS (General Packet Radio Services), which is a data technology for GSM networks. In addition to a conventional voice communication, a given mobile device can communicate with another such device via many different types of message transfer techniques, including SMS (short message service), enhanced SMS (EMS), multi-media message (MMS), email WAP, paging, or other known or later-developed wireless data formats. Example functions described herein may be implemented on any suitable electronic device, such as a computer or smartphone.

The electronic device 502 may include a touchscreen display 520 and/or other user interface for interacting with a user and for present information and images. As referred to herein, a "user interface" (UI) is generally a system by which users interact with an electronic device. An interface can include an input for allowing users to manipulate an electronic device, and can include an output for allowing the system to present information (e.g., e-book content) and/or data, indicate the effects of the user's manipulation, etc. An example of an interface on an electronic device includes a graphical user interface (GUI) that allows users to interact with programs in more ways than typing. A GUI typically can offer display objects, and visual indicators, as opposed to text-based interfaces, typed command labels or text navigation to represent information and actions available to a user. For example, an interface can be a display window or display object, which is selectable by a user of a mobile device for interaction. The display object can be displayed on a display screen of an electronic device and can be selected by and interacted with by a user using the interface. In an example, the display of the electronic device can be a touch screen, which can display the display icon. The user can depress the area of the display screen at which the display icon is displayed for selecting the display icon. In another example, the user can use any other suitable interface of a mobile device, such as a keypad, to select the display icon or display object. For example, the user can use a track ball or arrow keys for moving a cursor to highlight and select the display object.

Operating environments in which embodiments of the present disclosure may be implemented are also well-known. The electronic device 502 may be communicatively connected to a remote server for communication of data and captured images for processing in accordance with embodiments of the present disclosure. Further, the electronic device 502 may suitably power the light emitters and the image capture device via the cable 504. In a representative embodiment, an electronic device, such as an e-book reader, is connectable (for example, via WAP) to a transmission functionality that varies depending on implementation. Thus, for example, where the operating environment is a wide area wireless network (e.g., a 2.5G network, a 3G network, or a 4G network), the transmission functionality comprises one or more components such as a mobile switching center (MSC) (an enhanced ISDN switch that is responsible for call handling of mobile subscribers), a visitor location register (VLR) (an intelligent database that stores on a temporary basis data required to handle calls set up or received by mobile devices registered with the VLR), a home location register (HLR) (an intelligent database responsible for management of each subscriber's records), one or more base stations (which provide radio coverage with a cell), a base station controller (BSC) (a switch that acts as a local concentrator of traffic and provides local switching to effect handover between base stations), and a packet control unit (PCU) (a device that separates data traffic coming from a mobile device). The HLR also controls certain services associated with incoming calls. Of course, embodiments in accordance with the present disclosure may be implemented in other and next-generation mobile networks and devices as well. The mobile device is the physical equipment used by the end user, typically a subscriber to the wireless network. Typically, a mobile device is a 2.5G-compliant device, 3G-compliant device, or 4G-compliant device that includes a subscriber identity module (SIM), which is a smart card that carries subscriber-specific information, mobile equipment (e.g., radio and associated signal processing devices), a user interface (or a man-machine interface (MMI)), and one or more interfaces to external devices (e.g., computers, PDAs, and the like). The electronic device may also include a memory or data store.

Based on initial favorable testing with the flat tip inserter, an iteration of the inserter with integrated 2MP camera was made for further testing to enable manipulation of the cervix for effective use with women (see Results, Phantom Testing). The probe inserter was further iterated on to enable manipulation of the cervix for effective use in women with severely tilted uteri, namely retroverted (tilted posteriorly), anteverted (tilted anteriorly) and side-deviated uteri (tilted to the side) which condition affects about 20% of women. FIGS. 9A and 9B are cross-sectional side views showing using of a flat 800 and curved end 500 inserters with integrated 2 MP camera 900, respectively, for manipulation of the cervix 902. These figures show how the curved end of the colposcope 500 enables advantageous manipulation of the cervix 902. Since the cervix is shaped like a semi-sphere with the curved portion interfacing with the inserter, protrusion of the tip of the inserter is required to easily manipulate it. Further discussion of such advantages may be found in PCT Application Publication No. PCT/US2017/025197, also published as U.S. Patent Application Publication No. 2019/0150725, the disclosure of each of which is incorporated by reference in its entirety.

Inserters according to some embodiments include a spray mechanism integrated into a working channel of the device. Instead of using a cotton swab, a spray mechanism embedded within the inserter may also be utilized for the application of the contrast agent. The spray mechanism comprises of a customized nozzle including multiple holes with diameters ranging from 0.0001 cm to 0.5 cm at circumferential angles ranging from 0 to 360 degrees. The nozzle is connected to a channel with diameter from 0.001 cm to 0.5 cm from the distal to proximal end of the device. The contrast fluid may be injected in the proximal end with a syringe with a Luer lock and a volume capacity from 0.5 mL to 20 mL through a rubber tube into the spray channel embedded within the device. Using a spray instead of a cotton swab helps to minimize abrasion due to direct contact between the contrast delivery tool and the cervix.

Figure 12A:
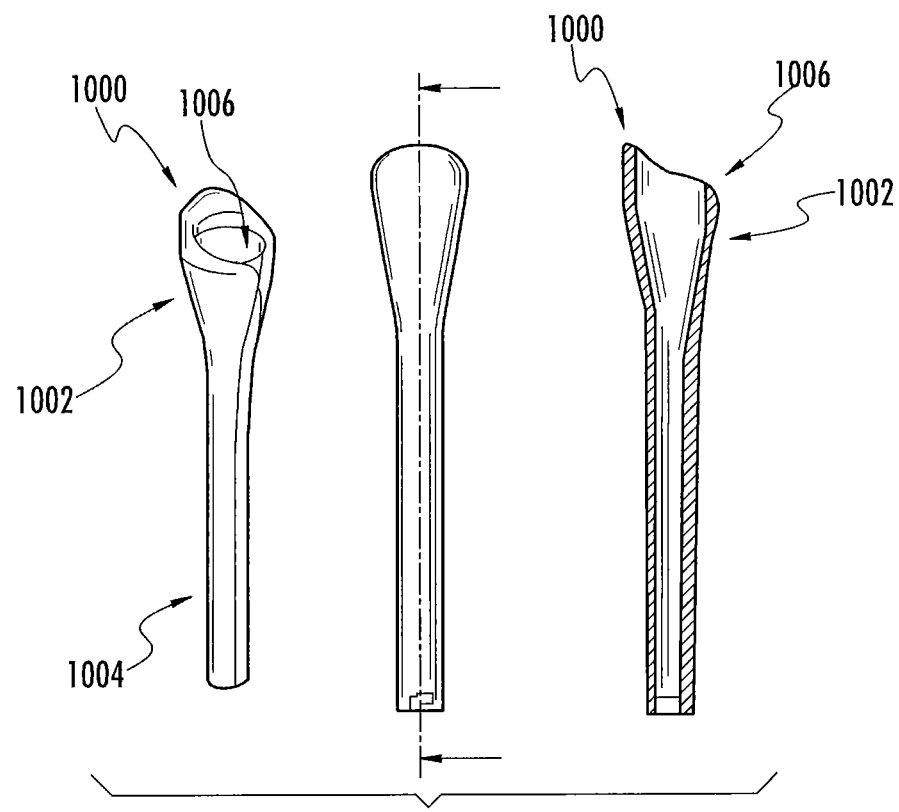
FIG. 12A illustrates various views of an inserter including a spray channel at the proximal tip of the inserter in accordance with embodiments of the present disclosure.
Figure 12B:
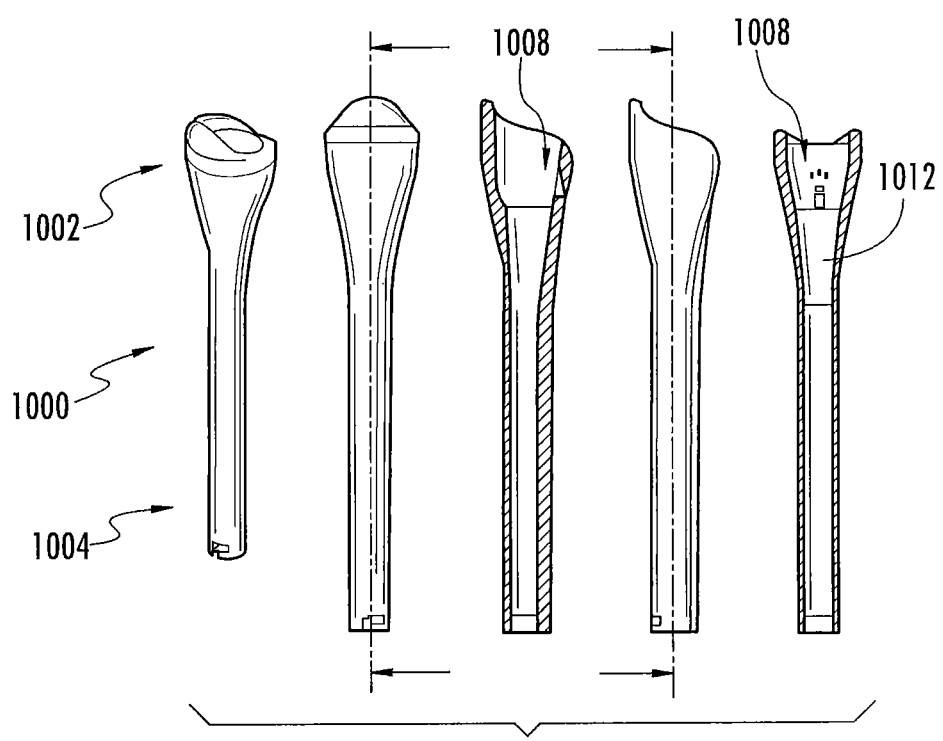
FIG. 12B illustrates various views of an inserter with a spray channel embedded in the inner wall of the inserter in accordance with embodiments of the present disclosure.
Figure 12C:
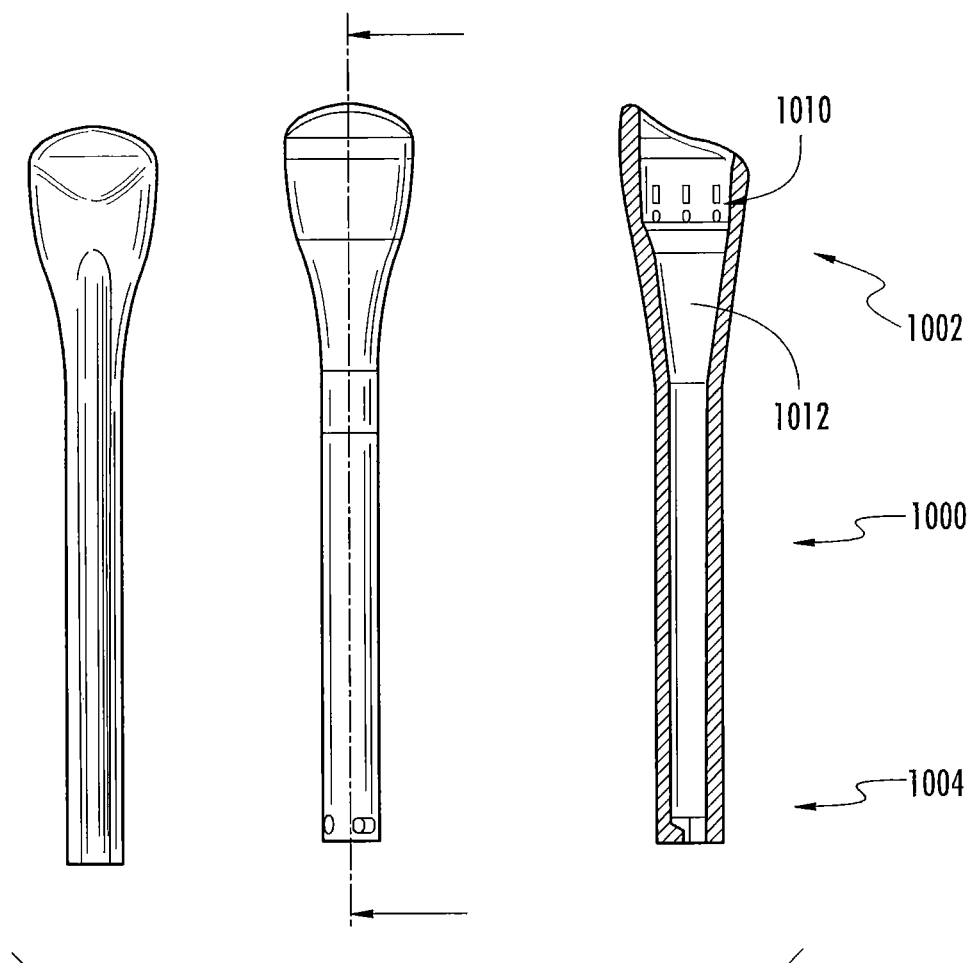
FIG. 12C illustrates various views of an inserter with a spray and/or working channel with protruding nozzle in accordance with embodiments of the present disclosure.

FIG. 12A shows one model of the nozzle 1006 at the tip of the inserter lip. The inserter 1000 includes proximal 1004 and distal 1002 ends and may include the features of the inserters described above. FIG. 12B shows a second model of the nozzle 1008 that protrudes from an inner wall 1012 of the funnel-like distal end 1002 of the inserter 1000. FIG. 12C shows a third model of the spray mechanism 1010 protruding from the inner wall 1012 of the distal end 1002 of the inserter 1000. The spray mechanism 1010 includes a circular loop through which circular nozzles, at angles ranging from −180 to 180 degrees relative to the inner wall of the inserter, emerge. The nozzles may be spaced apart and disposed along the entire circumference of the inner wall of the inserter 1000.

Figure 13A:
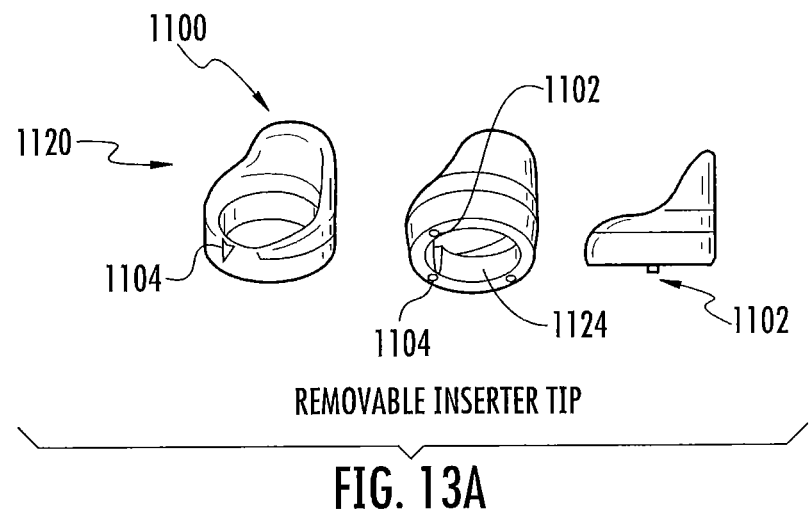
FIG. 13A illustrates various views of a silicone pliable s-curve inserter tip with female alignment hole in accordance with embodiments of the present disclosure.
Figure 13B:
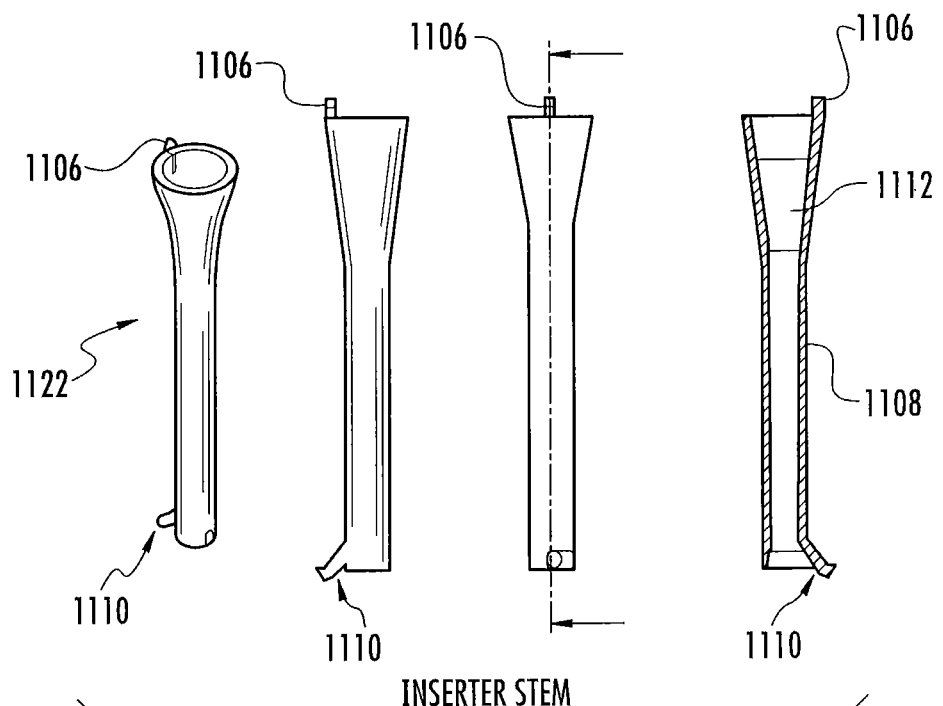
FIG. 13B illustrates various views of an inserter stem with male Luer spray channel connector, male press fit alignment peg for silicone tip, and spray channel in accordance with embodiments of the present disclosure.
Figure 16B:
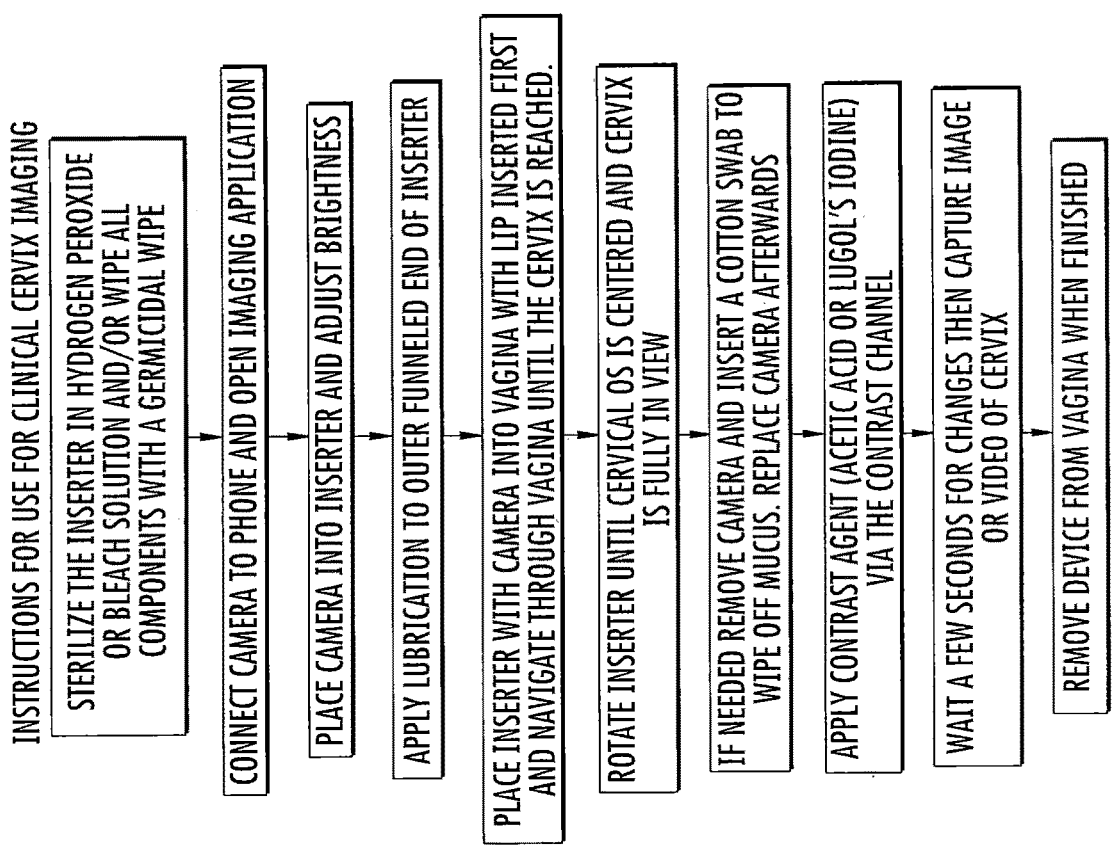
FIGS. 16A and 16B are flowcharts describing the use of inserters described herein to visualize the cervix in accordance with embodiments of the present disclosure.

Inserters according to some embodiments include a distal end that is removable to attach different shaped tips to the same inserter stem with the distal end personalized to the user. In FIG. 13A, 1100 is the lip on the removable tip 1120, 1102 is the lock or locking mechanism that is used to fasten the tip 1120 to the inserter stem 1122 (FIG. 13B), and 1104 is the spray mechanism or spray nozzle through which the contrast agent is sprayed. In FIG. 16B, 1106 is the tube or projection on which the nozzle 1104 fits and it feeds the nozzle the contrast agent, 1108 is the tube or channel that runs along the inserter stem carrying the contrast agent, and 1110 is a tube or receptacle in which a syringe is attached to spray contrast agent. The different s-shaped curves of the tip 1120 enable multi-axis viewing of female anatomy, such as vaginal walls, due to variable curvature of the inserter opening. It is noted that the inserter may include a working channel with diameter between 0.1 cm to 1 cm that enable collection of HPV, cervical cells, and/or biopsy with specialized tools. The addition of this channel enables compatibility with other clinical procedures.

The tip 1120 may be formed of a relatively soft material for comfort and increased manipulation capability. For example, the tip 1120 may be a polymer such as silicone (or have a silicone over-mold) such that the stem 1122 has increased rigidity relative to the tip 1120. The stem 1122 may also be a polymer such as ABS.

Instead of the locking mechanism described above, the stem and the tip may be permanently joined (e.g., by ultrasonic welding or adhered using epoxy). The entire inserter may include a polymer such as silicone or have a silicone over-mold. Alternatively, only the tip 1120 may be formed of silicone or have a silicone over-mold such that the stem 1122 has increased rigidity relative to the tip 1120.

Further, the nozzle 1104 may be defined in an inner wall 1112 of the stem 1122 and/or in an inner wall 1124 of the tip 1120 (i.e., rather than on the lip of the tip). The nozzle 1104 may be in fluid communication with the channel 1108 that extends from the proximal end of the stem 1122 to the nozzle 1104.

Figure 14A:
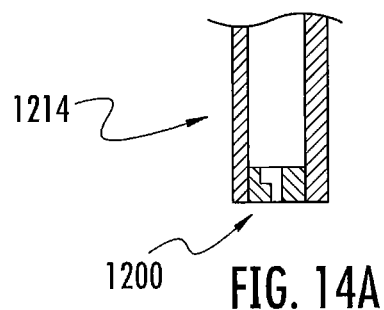
FIG. 14A illustrates a distal end of an introducer with camera bayonet lock in accordance with embodiments of the present disclosure.
Figure 14B:
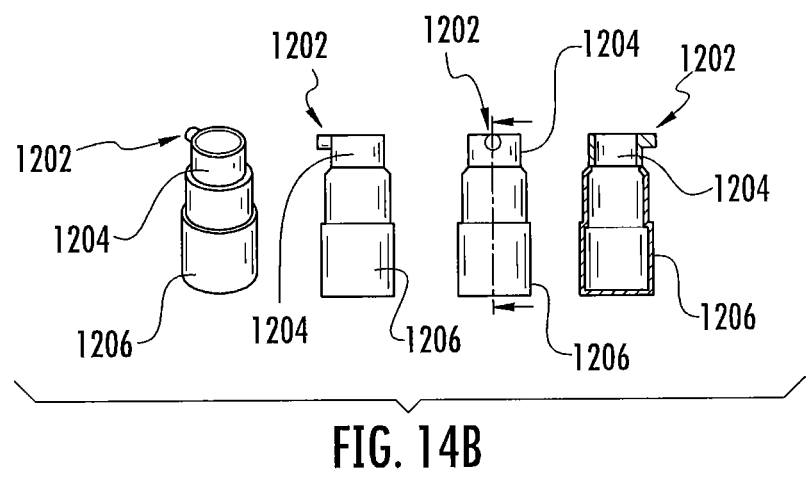
FIG. 14B illustrates various views of a camera side bayonet lock in accordance with embodiments of the present disclosure.

In some embodiments, the camera that is placed inside the inserter is locked into place using a bayonet lock mechanism. The lock mechanism enables the camera to be held in place with the proper upright orientation for image capture and facilitates one handed operation. FIG. 14A shows a bayonet groove or socket 1200 with a height between 0.01 mm to 5 cm and width between 0.01 mm and 1 cm, in the proximal end 1214 of the inserter into which the bayonet lock is slid. FIG. 14B illustrates the bayonet lock 1202, a cylindrical shaped knob, with a diameter between 0.1 mm and 5 mm and a height between 0.1 mm and 10 mm. In FIG. 14B, 1204 is a cylindrical tube on the bayonet lock that holds the camera in place, with a diameter between 2 mm and 50 mm, 1206 is an extension that partly covers the camera focus. The bayonet lock is engaged by pushing the knob 1202 into the groove 1200 and twisting to lock in place.

In some other embodiments, and as described in more detail below, the camera is held inside the inserter by a friction fit.

Figure 15:
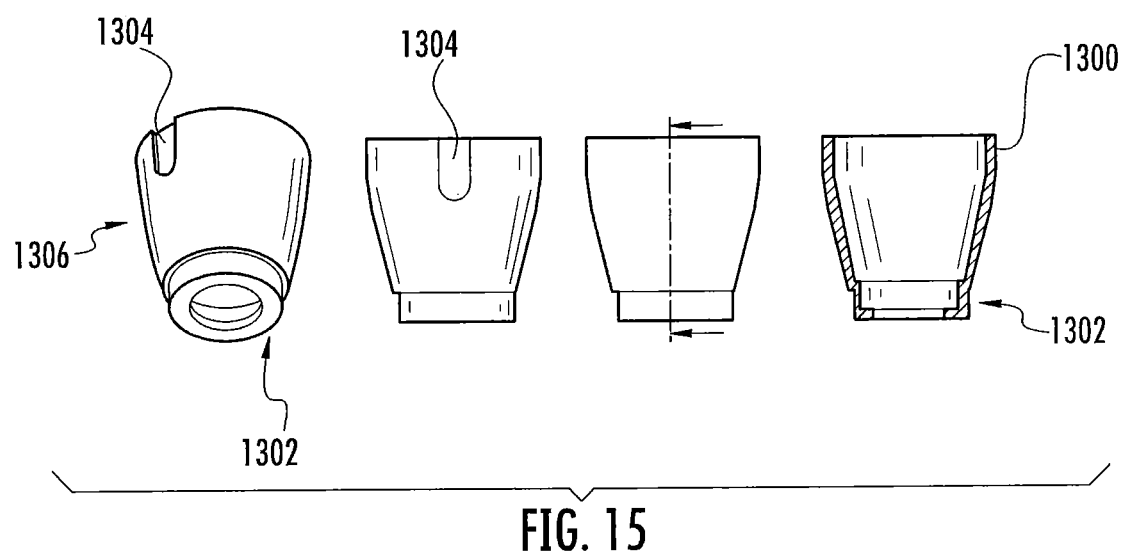
FIG. 15 illustrates various views of an integrated reflector an inserter in accordance with embodiments of the present disclosure.

An independently manufactured reflector or reflective silver coating may be applied inside the funnel-shaped end of the inserter to direct light onto the cervix and thus enable high image quality. The inserter body (or stem) and bayonet lock mechanism may be made of ABS plastic. The reflector may be made of a highly reflective polished surface that could include vapor deposition, metallic film, or machine from raw metal such as aluminum or steel that fit in the distal end just above the camera after it has been inserted into the inserter. An example of the reflector 1306 is shown in FIG. 15 with 1300 being the edge that is closest to the lip of the inserter and having a diameter range between 0.5 cm and 4 cm. A base or side 1302 is right on top of the camera and has a diameter range between 0.5 cm and 2 cm. A groove 1304 fits on top of the spray nozzle. An alternative to the reflector 1306 is a reflective coat that is spray painted or electroplated to an inner surface of the inserter (e.g., at the distal end or distal end portion thereof) and a medical grade epoxy is applied on the top layer for biocompatibility. The angle and height of the sidewall of the reflector is of great importance and should range between 45 and 85 degrees and height of 2 to 12.7 mm from the imaging axis.

Figure 16A:
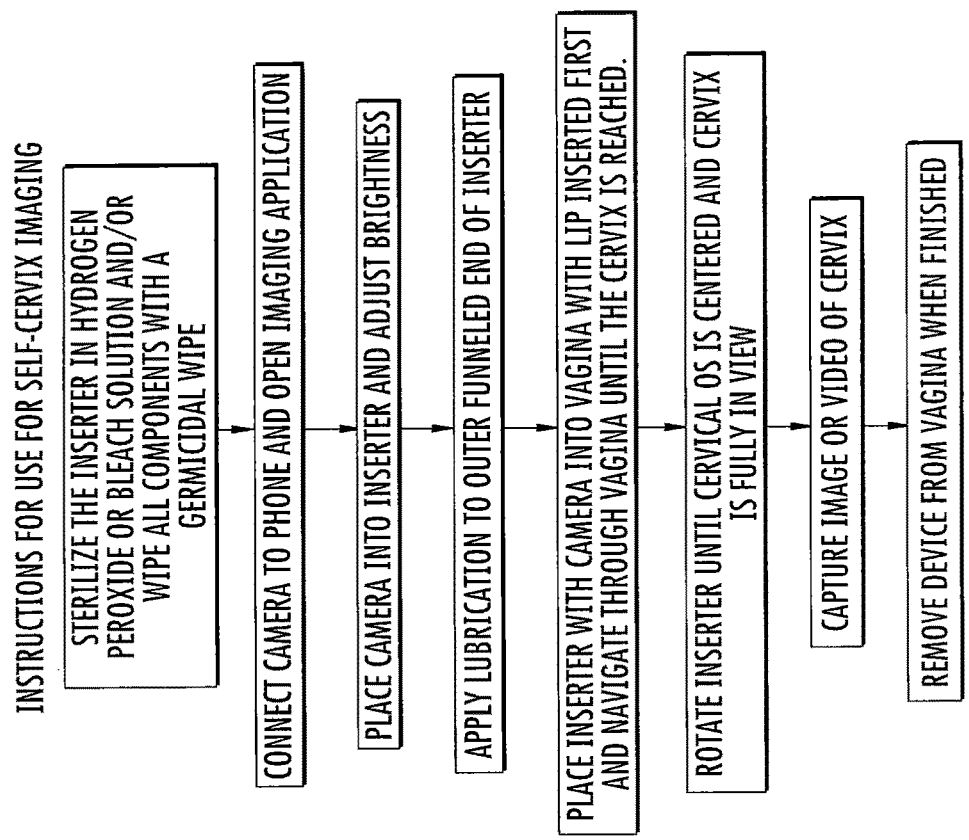
Figure 17:
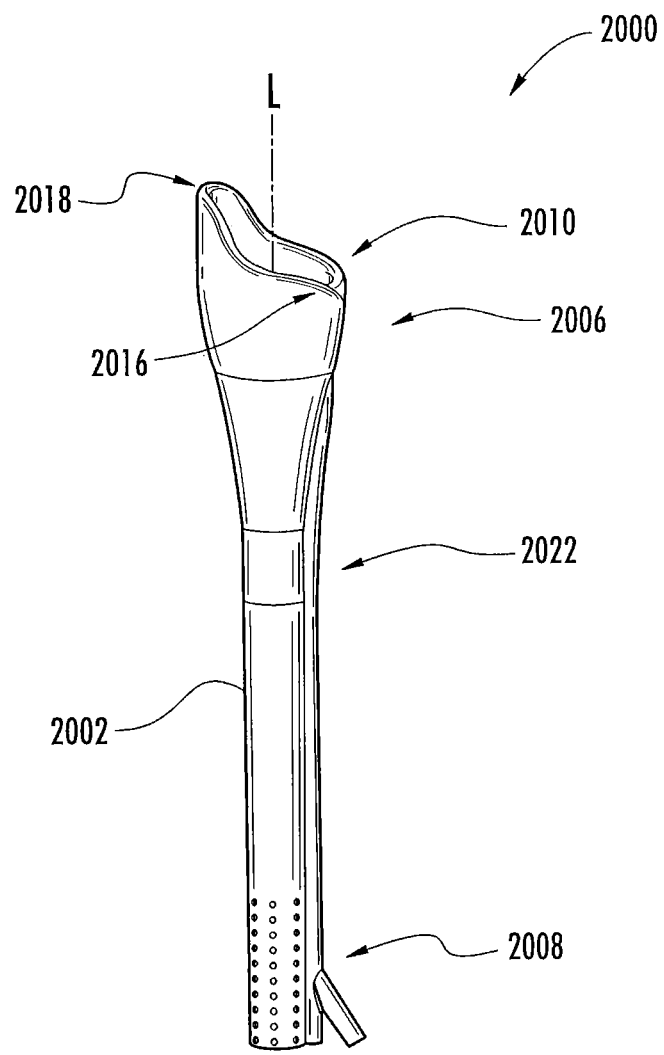
FIGS. 17-20 illustrate various views of an inserter in accordance with embodiments of the present disclosure.
Figure 18:
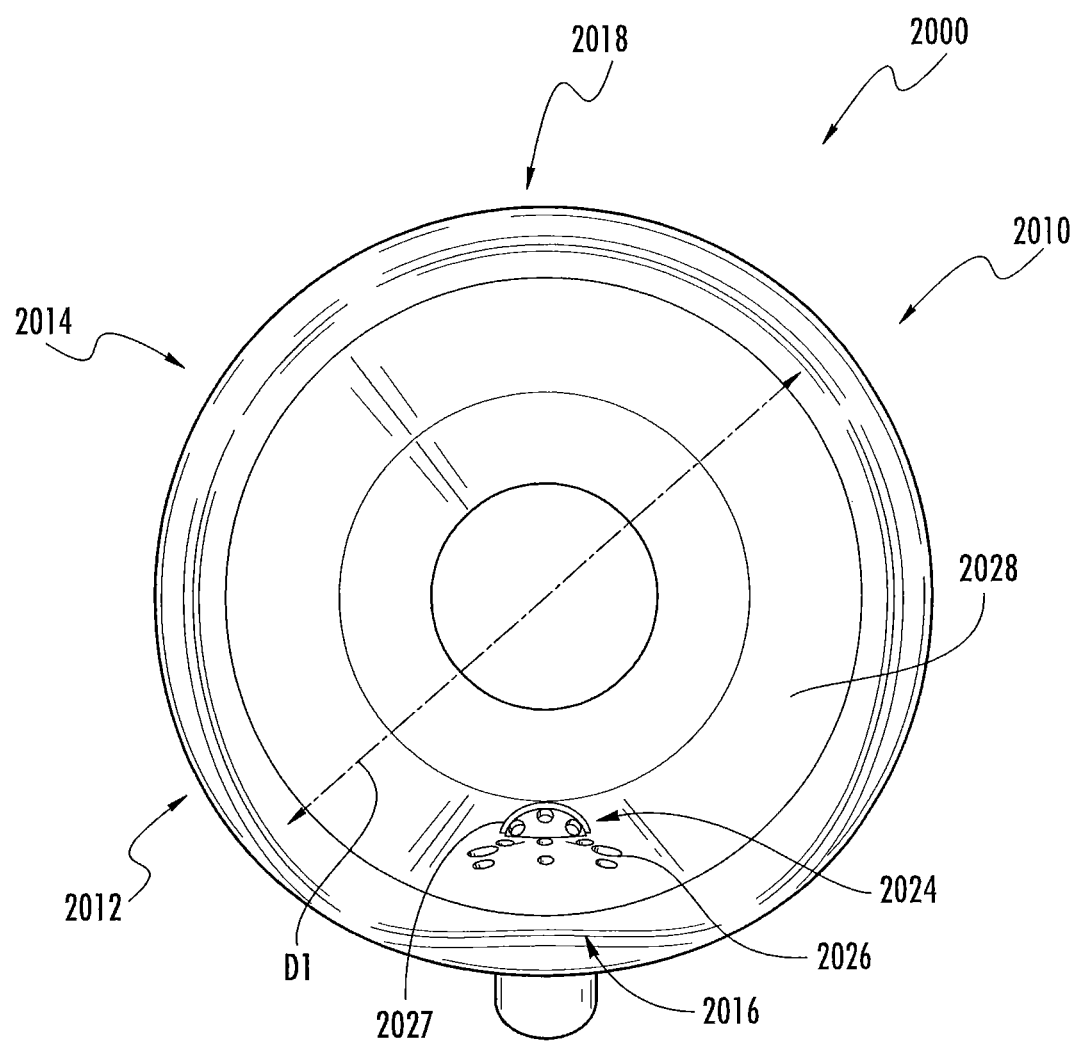
Figure 19:
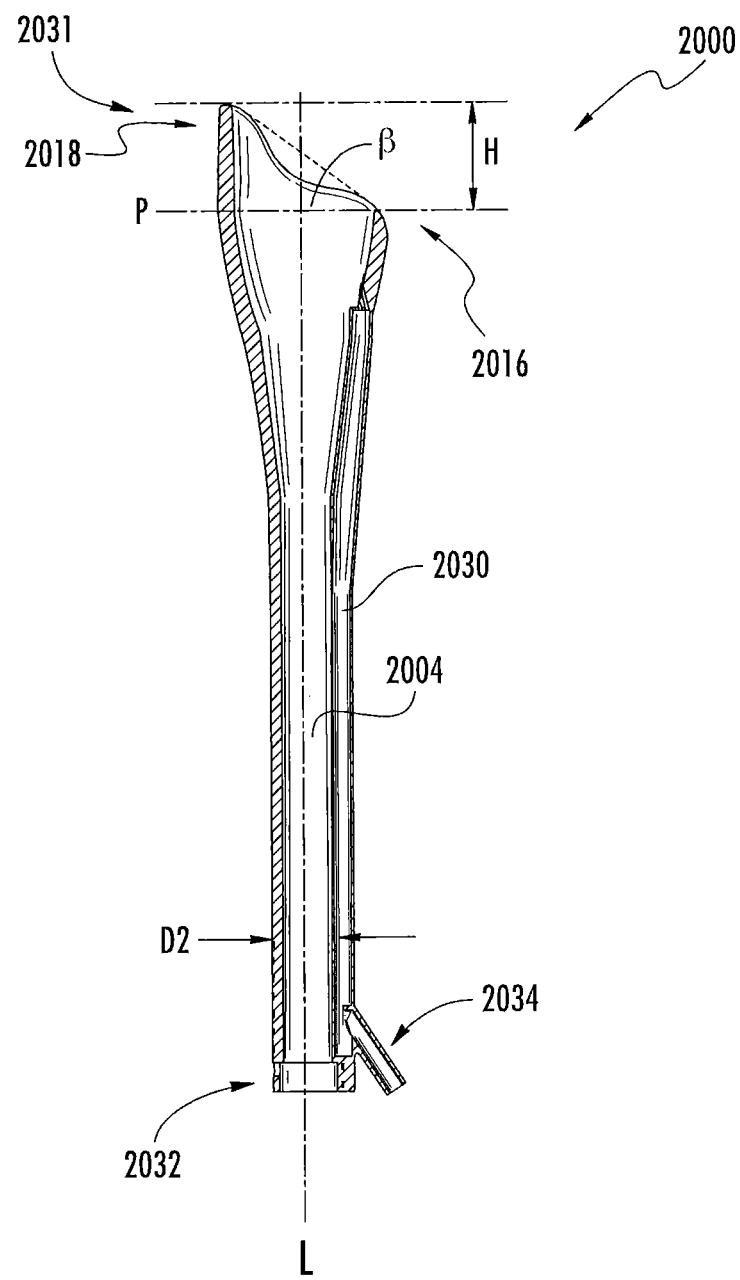
Figure 20:
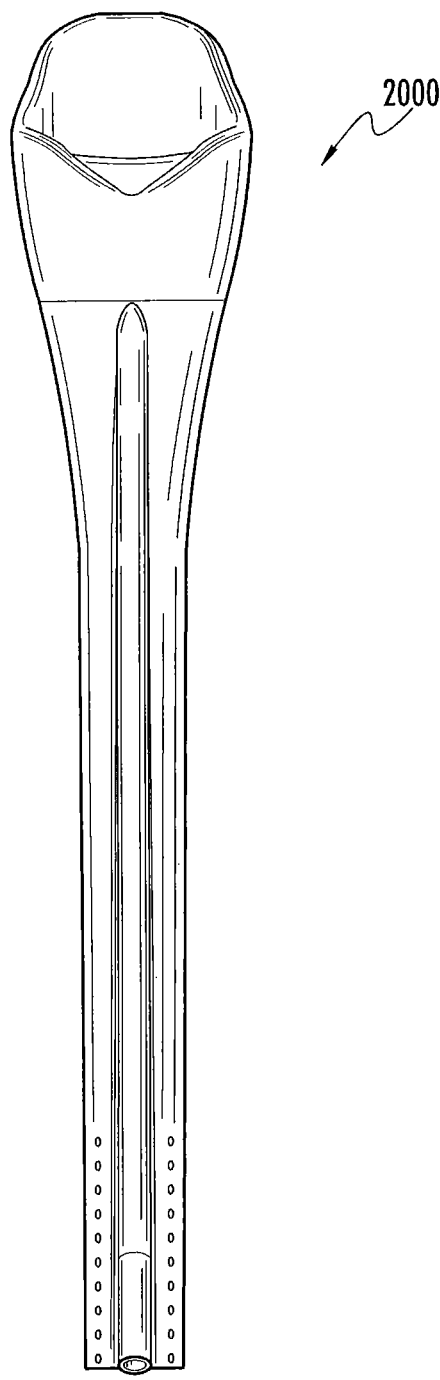
Figure 21:
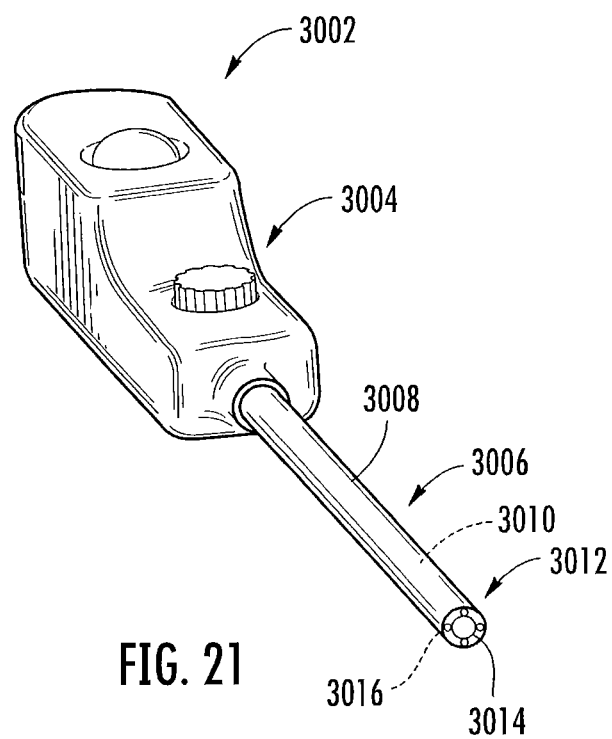
FIGS. 21-24 illustrate various views of a colposcope including the inserter of FIGS. 17-20.
Figure 22:
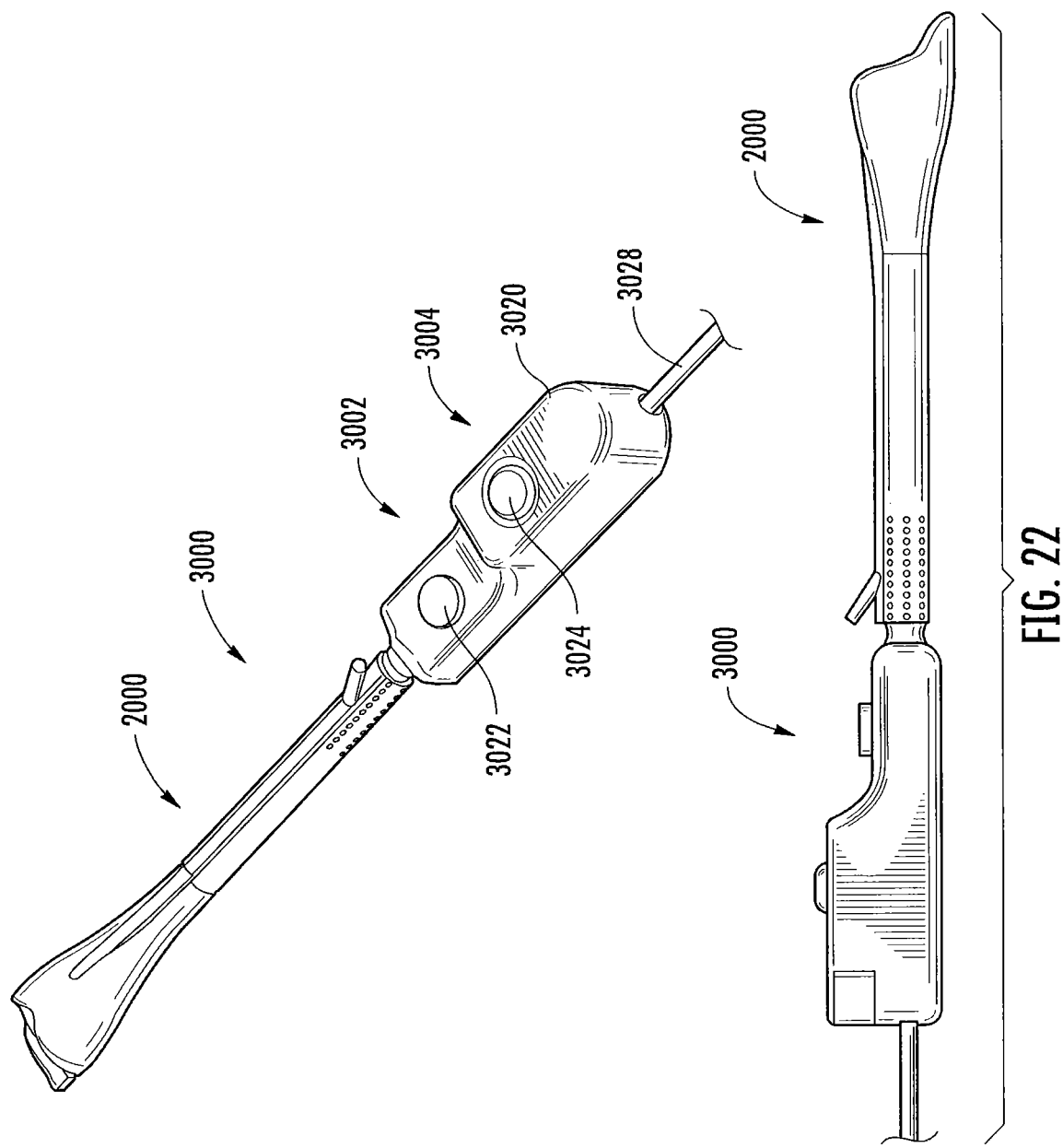

An algorithm or process for use of inserters described herein may be provided to users or health professionals for image capture. The algorithm includes the sterilization, storage and use of the inserter to visualize cervix or vaginal walls. FIGS. 16A and 16B describe the stages for the use of the inserter in a flowchart format.

An inserter 2000 according to some other embodiments is illustrated in FIGS. 17-23. The inserter 2000 includes an elongate body 2002 defining an interior space 2004 and having a distal end portion 2006 and a proximal end portion 2008. The distal end portion 2008 is substantially funnel shaped and includes first and second portions 2012, 2014 (e.g., first and second diametrically opposed portions). The first portion 2012 includes a base 2016 at a first edge of a distal end 2031 of the body 2002 and the second portion 2014 includes a lip 2018 at a second edge of the distal end 2031 that is diametrically opposed to the first edge. The lip 2018 is positioned further from the proximal end portion 2008 than is the base 2016. An image capture device is positioned within the interior space 2004 as described herein.

The body 2002 may include a transition portion 2022 between the proximal end portion 2008 and the distal end portion 2006. The proximal end portion 2008 of the body 2002 may have a constant diameter section. The distal end portion 2006 of the body 2002 may have a circular cross section that increases in diameter from the transition portion 2022 to the distal end 2010 of the body 2002.

The body 2002 may define a longitudinal axis L. An angle β may be defined between the base 2016 and the lip 2018 relative to a plane P that is orthogonal to the longitudinal axis L. The angle β may be between 30 and 50 degrees or between 35 and 45 degrees in various embodiments.

The lip 2018 may have a height H. For example, a distance between the base 2016 and the lip 2018 in a direction parallel to the longitudinal axis may be between 10 and 30 mm or between 15 and 25 mm in various embodiments.

A spray nozzle 2024 may be defined in an inner surface or wall 2026 of the inserter 2000. The nozzle 2024 may include a plurality of holes 2026 defined in an inner surface or wall 2028 of the body 2002. Some of the holes 2026 may be elongated and/or angled with respect to the longitudinal axis L to help disperse contrast media. Some of the holes 2026 may be provided on a shelf 2027 that extends inwardly from the inner surface 2028 toward the longitudinal axis L. The nozzle 2024 is in fluid communication with a channel 2030 that extends from a proximal end 2032 of the inserter body 2002 to the nozzle 2024. A tube and/or connector (e.g., luer lock) 2034 is at the proximal end 2032 of the body 2002.

As described herein, contrast media may be injected (e.g., by a syringe) into the tube and/or connector 2034, through the channel 2030, and out of the nozzle 2024 to spray contrast media onto an object of interest such as the cervix.

The present inventors have discovered that it is advantageous to position the nozzle 2024 at the inner surface 2028 and spaced apart from the base 2016 and the lip 2018 (e.g., as opposed to having the nozzle positioned on the base 2016). Specifically, the present inventors have discovered that such positioning helps prevent the nozzle 2024 from being blocked by mucous or other fluids during use.

As described above, the inserter 2000 includes a tubular body and a funnel shaped tip that serves to part the vaginal walls for visualization of the cervix. Since cervices can be tilted away from the center, it was important to create a lip that protruded from the funnel-shaped tip. An iterative process of testing multiple prototypes on phantoms was used to optimize the lip to simplify manipulation of the cervix. To enhance image quality, a reflective surface was designed for the inner wall of the inserter. The reflector spanned the wall from the tip of the camera to the end of the lip. Use of the colposcope including the inserter 2000 for cervical cancer screening may require the use of contrast agents such as acetic acid or Lugol's iodine. Thus, a channel for contrast agent application was added to the inserter 2000. The proximal end (the end farthest from the cervix) of the contrast agent application channel has a Luer lock connector, which couples to a Luer lock syringe for contrast application. The distal end (the end closest to the cervix) has a nozzle, which sprays the contrast over the surface of the cervix.

A colposcope 3000 according to some embodiments is illustrated in FIGS. 21-24. The colposcope 3000 includes the inserter 2000 and a handle and camera assembly 3002 (also referred to herein as an imaging device). The handle and camera assembly 3002 includes a handle 3004 and a probe 3006 extending from the handle 3004. The probe 3006 may have rigid body 3008 (the body 3008 may be formed of a metal such as aluminum). Inside the body 3008 is a camera 3010. At a distal end 3012 of the probe 3006 there may be a (anti-reflective) hydrophobic window 3014 in front of the camera lens and a plurality of LEDs 3016 surrounding the camera lens (e.g., four to six white LEDs that are equally spaced apart circumferentially and/or radially around the camera lens).

The handle 3004 includes a body 3020 which may be a rigid plastic such as ABS or polypropylene. An LED (brightness) adjust button or dial 3022 and an image capture button 3024 are on the body 3020. Inside the probe 3006 and/or the handle 3004 is a microprocessor that may cooperate with an USB board to send image data to an electronic device (e.g., laptop, tablet, smartphone) via a USB cable 3028. Additionally or alternatively, the microprocessor may cooperate with a wireless module and/or transmitter to wirelessly transmit the image data to the electronic device (e.g., via Bluetooth).

Figure 23:
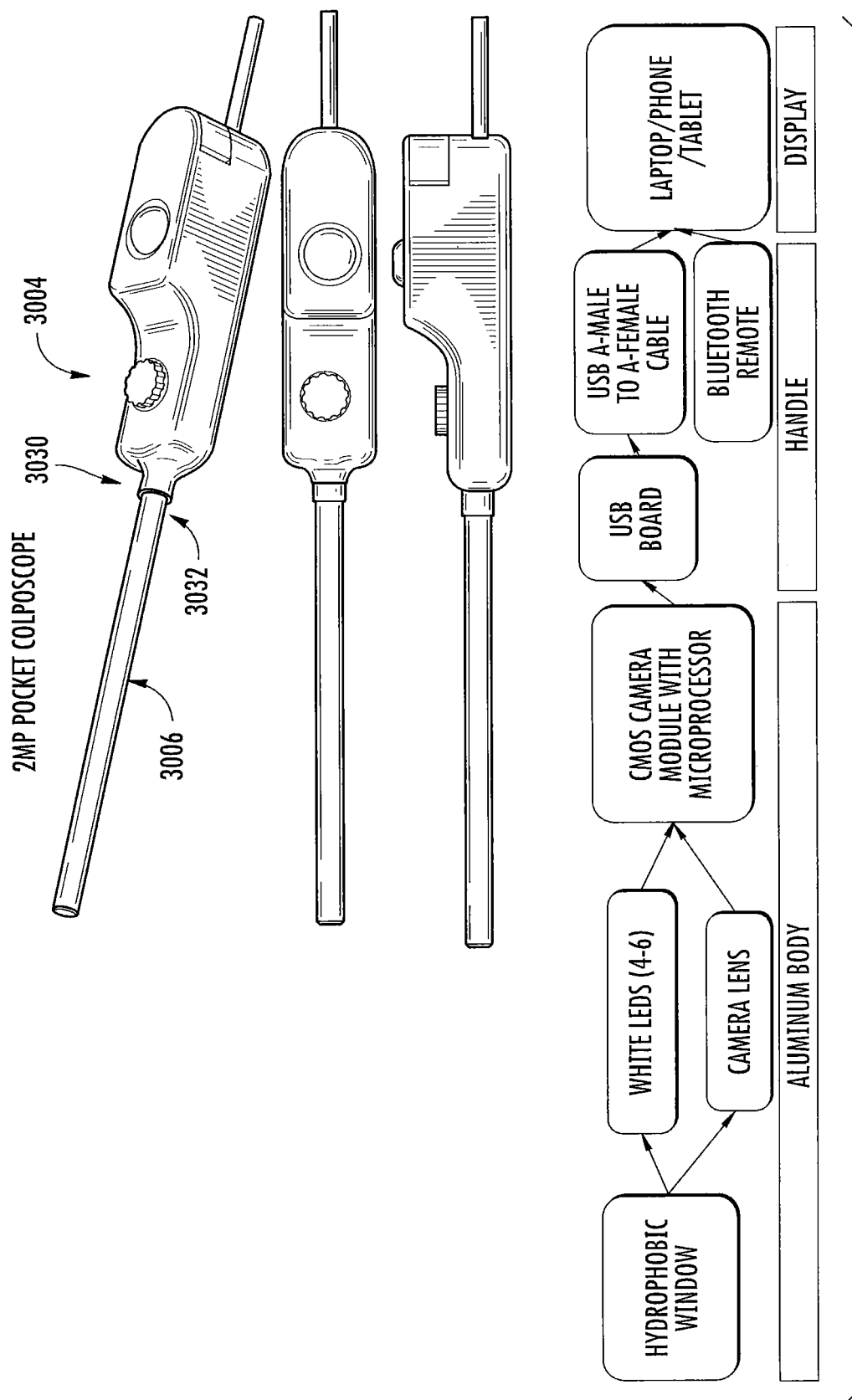
Figure 24:
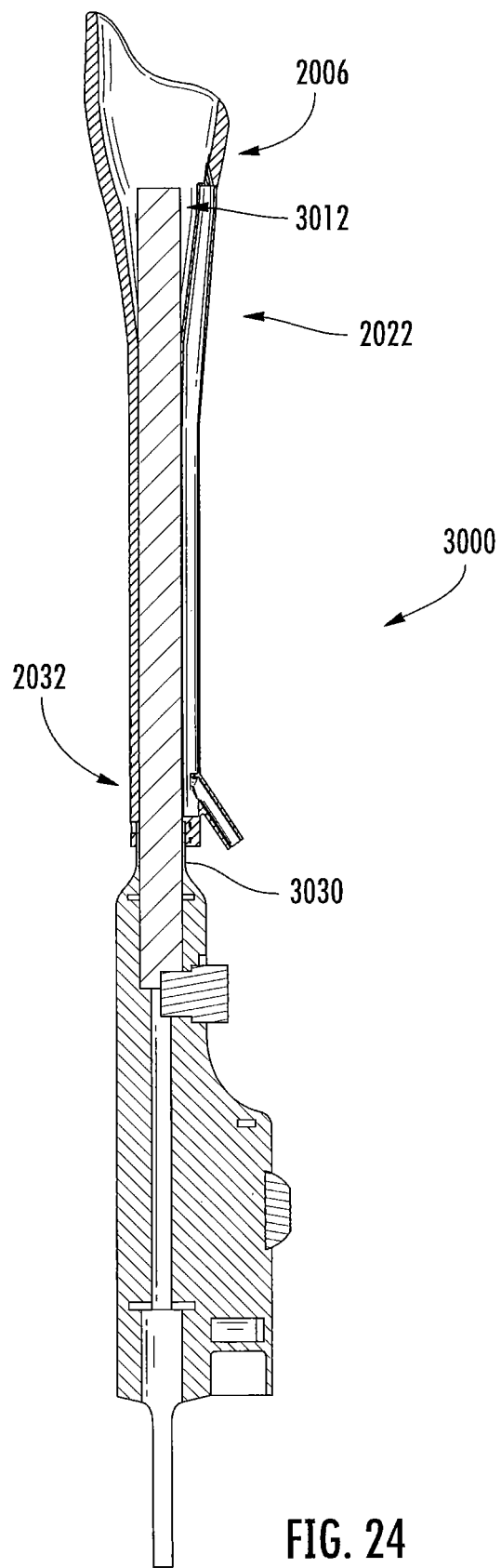

Referring to FIGS. 23 and 24, the handle 3004 may include a collar or extension 3030 that surrounds a proximal end portion 3032 of the probe 3006. In position, and as shown in FIG. 24, the handle extension may be held within the proximal end 2032 of the inserter 2000 with a friction fit (e.g., to hold the camera and handle assembly 3002 in the inserter 2000 in an installed position). Also as shown in FIG. 24, the distal end 3012 of the probe 3006 may be held in the distal end portion 2006 or the transition portion 2022 of the inserter 2000 in the installed position.

Referring to FIGS. 25A-25D, a hydrophobic window 2100 is attached to or integrated with the inserter 2000. Specifically, the hydrophobic window 2100 is in the interior space 2004. The window 2100 may be adhered or ultrasonically welded to the inner surface 2028 of the inserter 2000, for example. The window 2100 may completely block the interior space 2004 such that the window 2100 acts as a barrier for the image capture device 3000. In this way, the image capture device never comes into contact with tissue or bodily fluids. The inserter 2000 can thus act as a disposable sleeve and the colposcope or image capture device can be reused between patients without the need for sterilization (the image capture device could simply be wiped down between patients).

The colposcope 3000 allows for self-examination or physician-based examination of the cervix. It includes an imaging device and an inserter; the latter obviates the need for a speculum.

Any patents or publications mentioned in this specification are indicative of the levels of those skilled in the art to which the present subject matter pertains. These patents and publications are herein incorporated by reference to the same extent as if each individual publication was specifically and individually indicated to be incorporated by reference.

One skilled in the art will readily appreciate that the present subject matter is well adapted to carry out the objects and obtain the ends and advantages mentioned, as well as those inherent therein. The present examples along with the methods described herein are presently representative of various embodiments, are exemplary, and are not intended as limitations on the scope of the present subject matter. Changes therein and other uses will occur to those skilled in the art which are encompassed within the spirit of the present subject matter as defined by the scope of the claims.

The invention claimed is:

1. A colposcope comprising:
   an inserter comprising an elongated body defining an interior space and having a distal end portion and a proximal end portion, the distal end portion being substantially funnel shaped and having a distal end that includes first and second portions, the first portion including a base at a first edge of the distal end, the second portion including a lip at a second edge of the distal end that is diametrically opposed from the first edge, the lip being positioned further from the proximal end portion than the base; and
   an image capture device within the interior space of the elongated body,
   wherein the entirety of the body defines a straight central longitudinal axis,
   an edge of the distal end extending between the base and the lip defines an S-shaped curve,
   the body comprises a stem defining the proximal end portion and a tip defining the distal end portion,
   the stem comprises: a first end portion defining the proximal end portion of the body; and an opposite second end portion between the proximal end portion of the body and the distal end portion of the body,
   the second end portion of the stem has a circular cross section that increases in diameter from the proximal end portion of the body to the distal end portion of the body,
   the tip is releasably attached to the stem, and
   the stem has increased rigidity relative to the tip.

2. The colposcope of claim 1 wherein the proximal end portion of the body has a constant diameter circular cross section.

3. The colposcope of claim 1 wherein the image capture device comprises a handle and an elongated probe extending from the handle.

4. The colposcope of claim 3 wherein:
a plurality of LEDs surround a lens of the image capture device at a distal end of the probe;
the handle comprises a body, a first button or dial on the body for adjusting the brightness of the plurality of LEDs, and a second button on the body for capturing an image.

5. The colposcope of claim 1 further comprising an anti-reflective, hydrophobic window in the interior space of the elongated body of the inserter and defining a barrier for the image capture device such that any fluid entering the interior space from the distal end does not reach the image capture device, wherein the inserter is single-use disposable.

6. The colposcope of claim 1 further comprising:
at least one channel that extends along the body from the proximal end portion to the distal end portion for fluid communication of contrast agent from the proximal end portion to the distal end portion; and
a spray mechanism in fluid communication with the at least one channel at the distal end portion, the spray mechanism configured to disperse the contrast agent at the distal end portion.

7. The colposcope of claim 6 wherein the spray mechanism comprises a spray nozzle comprising a plurality of holes defined in an inner surface of the body and spaced apart from the distal end of the body.

8. The colposcope of claim 6 further comprising a tube and/or connector in fluid communication with the at least one channel at a proximal end of the body, the tube and/or connector configured to receive a syringe for injection of the contrast agent.

9. The colposcope of claim 1 further comprising a reflective coating on an inner surface of the distal end portion of the body.

10. The colposcope of claim 1 wherein the elongated body has a fixed length and the proximal end portion has a fixed diameter for fitting to the image capture device.

11. The colposcope of claim 1 further comprising:
an electronic device; and
at least one cable configured to operatively connect the electronic device and the image capture device,
wherein the electronic device is configured to power and communicate with the image capture device, and wherein the electronic device includes a user interface to enable data storage and/or telemedicine.

12. The colposcope of claim 1 wherein the tip comprises a biocompatible material.

13. The colposcope of claim 12 wherein the biocompatible material comprises rubber or silicone.

14. The colposcope of claim 1 wherein:
an angle is defined between the base and the lip relative to a plane that is orthogonal to the longitudinal axis; and
the angle is between 30 and 50 degrees.

15. The colposcope of claim 1 wherein a distance between the base and the lip in a direction parallel to the longitudinal axis is between 10 and 30 mm.

16. The colposcope of claim 1 wherein the image capture device comprises an elongated probe extending from the proximal end portion to the distal end portion.

17. The colposcope of claim 16 wherein the image capture device comprises a plurality of LEDs surrounding a lens at a distal end of the probe that resides in the interior space of the elongated body at the distal end portion thereof.

18. A method comprising:
providing the colposcope of claim 1;
sterilizing the inserter;
connecting the image capture device to an electronic device;
adjusting the brightness, resolution, and/or focus of the image capture device;
applying lubrication on the funnel shaped distal end of the inserter;
placing the inserter into a vagina with the lip first;
navigating the inserter through the vaginal canal until the cervix is reached;
rotating the inserter until cervical os is centered and cervix is fully in view;
capturing an image or video of the cervix; and
viewing the image or video on an electronic device that is communicatively coupled to the image capture device.

* * * * *